(12) United States Patent
Jonczyk et al.

(10) Patent No.: US 8,987,301 B2
(45) Date of Patent: Mar. 24, 2015

(54) HETEROARYLAMINOQUINOLINES AS TGF-BETA RECEPTOR KINASE INHIBITORS

(75) Inventors: Alfred Jonczyk, Darmstadt (DE); Christiane Amendt, Muehltal/Trautheim (DE); Frank Zenke, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 12 days.

(21) Appl. No.: 13/508,090

(22) PCT Filed: Oct. 12, 2010

(86) PCT No.: PCT/EP2010/006239
§ 371 (c)(1),
(2), (4) Date: May 4, 2012

(87) PCT Pub. No.: WO2011/054433
PCT Pub. Date: May 12, 2011

(65) Prior Publication Data
US 2012/0225875 A1    Sep. 6, 2012

(30) Foreign Application Priority Data

Nov. 7, 2009  (EP) ...................................... 09013988

(51) Int. Cl.
*A01N 43/42* (2006.01)
*A61K 31/47* (2006.01)
*C07D 401/12* (2006.01)
*C07D 401/14* (2006.01)
*C07D 471/04* (2006.01)

(52) U.S. Cl.
CPC ............ *C07D 401/12* (2013.01); *C07D 401/14* (2013.01); *C07D 471/04* (2013.01)
USPC ............ 514/312; 514/311; 546/152; 546/153

(58) Field of Classification Search
USPC ........................... 546/152, 153; 514/311, 312
See application file for complete search history.

(56) References Cited

U.S. PATENT DOCUMENTS

| | | | |
|---|---|---|---|
| 4,694,000 | A | 9/1987 | Timmerman et al. |
| 5,506,235 | A | 4/1996 | Moyer et al. |
| 6,184,226 | B1 | 2/2001 | Chakravarty et al. |
| 6,476,031 | B1 | 11/2002 | Chakravarty et al. |
| 6,740,649 | B2 | 5/2004 | Ott et al. |
| 7,189,714 | B2 | 3/2007 | Chapdelaine et al. |
| 7,348,340 | B2 | 3/2008 | Chapdelaine et al. |
| 2003/0139388 | A1 | 7/2003 | Ott et al. |
| 2004/0077644 | A1 | 4/2004 | Chapdelaine et al. |
| 2005/0032835 | A1* | 2/2005 | Pandey et al. ................. 514/313 |
| 2006/0217377 | A1 | 9/2006 | Gonzalez et al. |
| 2007/0129363 | A1 | 6/2007 | Chapdelaine et al. |
| 2009/0209536 | A1 | 8/2009 | Gahman et al. |
| 2010/0331293 | A1 | 12/2010 | Cushing et al. |
| 2013/0203750 | A1 | 8/2013 | Kurimura et al. |
| 2014/0288065 | A1 | 9/2014 | Kurimura et al. |

FOREIGN PATENT DOCUMENTS

| | | |
|---|---|---|
| GB | 1158868 A | 7/1969 |
| WO | 8501501 A1 | 4/1985 |
| WO | 9303030 | 2/1993 |
| WO | 00/12497 A2 | 3/2000 |
| WO | WO 00/12497 * | 3/2000 |
| WO | 0112608 A1 | 2/2001 |
| WO | 0236567 A1 | 5/2002 |
| WO | 03024899 A2 | 3/2003 |
| WO | 03097615 A1 | 11/2003 |
| WO | 2004/065392 A1 | 8/2004 |
| WO | 2004067513 A1 | 8/2004 |
| WO | WO 2004/065392 * | 8/2004 |
| WO | 2004/081009 A1 | 9/2004 |
| WO | 2006121218 A1 | 5/2006 |
| WO | 2006058201 A1 | 6/2006 |
| WO | 2008157500 A1 | 12/2008 |
| WO | 2010151791 | 12/2010 |

OTHER PUBLICATIONS

Gellibert et al., BioOrganic & Med. Chem. Letters, vol. 19,8,pp. 2277-2281 (2009).*
Strekowski et al., J'nal of Organic Chem. ACS, vol. 62, No. 12, pp. 4193-4196 (1997).*
Pinedo et al (2000).*
McMahon et al (2000).*
Gellibert, F. et al., "Design of novel quinazoline derivatives and related analogues as potent and selective ALK5 inhibitors," Bioorganic & Medicinal Chemistry Letters, Apr. 15, 2009, vol. 19, No. 8, pp. 2277-2281; Cited in International Search Report issued in corresponding PCT/EP2010/006239 on Dec. 22, 2010.
Strekowski, L. et al., Synthesis of Bis(2-arylquinolin-4-yl) amines by Lithium Bis(trimethylsilyl) amide-mediated Cyclization of Ketimines Derviced from 2-(Trifluoromethyl) anilines and Aryl Methyl Ketones; Cited in International Search Report issued in corresponding PCT/EP2010/006239 on Dec. 22, 2010.

(Continued)

Primary Examiner — Paul V. Ward
(74) Attorney, Agent, or Firm — Millen, White, Zelano & Branigan, P.C.

(57) ABSTRACT

Novel hetarylaminoquinoline derivatives of formula (I)

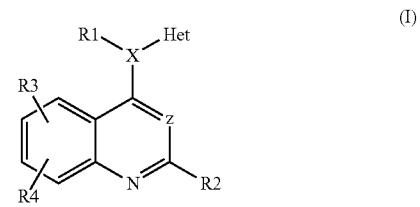

wherein X, Z, Het, R1, R2, R3 and R4 have the meaning according to claim 1, are inhibitors of ATP consuming proteins, and can be employed, inter alia, for the treatment of tumors.

19 Claims, No Drawings

(56) References Cited

OTHER PUBLICATIONS

International Search Report, dated Dec. 22, 2010, issued in corresponding PCT/EP2010/006239.
Office Action for related Japanese Patent Application No. 2012-537312 dated Oct. 7, 2014.
English Translation of Office Action for related Japanese Patent Application No. 2012-537312 dated Oct. 7, 2014.
Registry (STN) [online], Apr. 16, 2009, CAS Registration No. 1135234-24-0.
Registry (STN) [online], Apr. 16, 2009, CAS Registration No. 1135231-85-4.
Registry (STN) [online], Apr. 16, 2009, CAS Registration No. 1135231-35-4.
Registry (SIN) [online], Apr. 16, 2009, CAS Registration No. 1135222-62-6.
Registry (STN) [online], Nov. 11, 2008, CAS Registration No. 1071659-23-8.
Registry (STN) [online], Jun. 6, 2008, CAS Registration No. 1027311-25-6.
Registry (SIN) [online], Jun. 6, 2008, CAS Registration No. 1027061-81-9.
Registry (STN) [online], Jun. 6, 2008, CAS Registration No. 1026869-73-7.
Registry (STN) [online], Dec. 21, 2007, CAS Registration No. 959322-54-4.
Registry (STN) [online], Oct. 29, 2004, CAS Registration No. 772310-85-7.
Registry (STN) [online], Oct. 5, 2004, CAS Registration No. 757159-25-4.
Registry (STN) [online], Aug. 29, 2004, CAS Registration No. 735240-68-3.
Registry (STN) [online], Feb. 27, 2002, CAS Registration No. 396099-60-8.
Registry (STN) [online], Oct. 26, 2005, CAS Registration No. 866155-25-1.
Registry (STN) [online], Jan. 7, 2002, CAS Registration No. 380642-21-7.
Registry (STN) [online], Jan. 2, 2005, CAS Registration No. 807288-16-0.
Bodajla, M. et al., "Azolylquinazolines, Synthesis and Biological Activity," Chem. Papers, 1994, vol. 48, No. 6, pp. 432-436.
English Abstract of WO0112608, Publication Date: Feb. 22, 2001.
Andersen, K. E. et al, "Oxadiazoles as bioisosteric transformations of carboxylic functionalities. II," Eur. J. Med. Chem., 1996, vol. 31, pp. 417-425.
Jantova, S. et al., "Relationship between the Structure, cytotoxicity and hydrophobicity of quinazoline derivatives by quantitative structure-activity relationship," Folia Biologien, 1997, vol. 43, pp. 83-89.
Crawforth, C. E. et al., "Organolithium Chemistry of N-Heterocycles. Part IV. Formation of 1,2,4,5-Tetrahydro-4,4-diphenyl-2,5-methano-3,1-benzoxazepines from quinolines," J.C.S. Perkin Transactions 1: Organic and Bioorganic Chemistry, 1972, vol. 9-10, pp. 1176-1179.

* cited by examiner

HETEROARYLAMINOQUINOLINES AS TGF-BETA RECEPTOR KINASE INHIBITORS

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by ATP consuming proteins like kinases plays a role, particularly to inhibitors of TGF-beta receptor kinases. Objects of the invention are also pharmaceutical compositions that comprise these compounds, and to the use of the compounds for the treatment of kinase-induced diseases.

Transforming growth factor beta is the prototype of the TGF-beta superfamily, a family of highly preserved, pleiotrophic growth factors, which carry out important functions both during embryo development and also in the adult organism. In mammals, three isoforms of TGF-beta (TGF-beta 1, 2 and 3) have been identified, TGF-beta 1 being the commonest isoform (Kingsley (1994) Genes Dev 8:133-146). TGF-beta 3 is expressed, for example, only in mesenchymal cells, whereas TGF-beta 1 is found in mesenchymal and epithelial cells. TGF-beta is synthesized as pre-proprotein and is released in inactive form into the extracellular matrix (Derynck (1985) Nature 316: 701-705; Bottinger (1996) PNAS 93: 5877-5882). Besides the prosequence being cleaved off, which is also known as latency associated peptide (LAP) and remaining associated with the mature region, one of the 4 isoforms of the latent TGF-beta binding proteins (LTBP 1-4) may also be bound to TGF-beta (Gentry (1988) Mol Cell Biol 8: 4162-4168, Munger (1997) Kindey Int 51: 1376-1382). The activation of the inactive complex that is necessary for the development of the biological action of TGF-beta has not yet been clarified in full. However, proteolytic processing, for example by plasmin, plasma transglutaminase or thrombospondin, is certainly necessary (Munger (1997) Kindey Int 51: 1376-1382). The activated ligand TGF-beta mediates its biological action via three TGF-beta receptors on the membrane, the ubiquitously expressed type I and type II receptors and the type III receptors betaglycan and endoglin, the latter only being expressed in endothelial cells (Gougos (1990) J Biol Chem 264: 8361-8364, Loeps-Casillas (1994) J Cell Biol 124:557-568). Both type III TGF-beta receptors lack an intracellular kinase domain which facilitates signal transmission into the cell. Since the type III TGF-beta receptors bind all three TGF-beta isoforms with high affinity and type II TGF-beta receptor also has higher affinity for ligands bonded to type III receptor, the biological function is thought to consist in regulation of the availability of the ligands for type I and type II TGF-beta receptors (Lastres (1996) J Cell Biol 133:1109-1121; Lopes-Casillas (1993) Cell 73: 1435-1344). The structurally closely related type I and type II receptors have a serine/threonine kinase domain, which is responsible for signal transmission, in the cytoplasmatic region. Type II TGF-beta receptor binds TGF-beta, after which the type I TGF-beta receptor is recruited to this signal-transmitting complex. The serine/threonine kinase domain of the type II receptor is constitutively active and is able to phosphorylate seryl radicals in this complex in the so-called GS domain of the type I receptor. This phosphorylation activates the kinase of the type I receptor, which is now itself able to phosphorylate intracellular signal mediators, the SMAD proteins, and thus initiates intracellular signal transmission (summarized in Derynck (1997) Biochim Biophys Acta 1333: F105-F150).

The proteins of the SMAD family serve as substrates for all TGF-beta family receptor kinases. To date, 8 SMAD proteins have been identified, which can be divided into 3 groups: (1) receptor-associated SMADs (R-SMADs) are direct substrates of the TGF-β receptor kinases (SMAD1, 2, 3, 5, 8); (2) co-SMADs, which associate with the R-Smads during the signal cascade (SMAD4); and (3) inhibitory SMADs (SMAD6, 7), which inhibit the activity of the above-mentioned SMAD proteins. Of the various R-SMADs, SMAD2 and SMAD3 are the TGF-beta-specific signal mediators. In the TGF-beta signal cascade, SMAD2/SMAD3 are thus phosphorylated by the type I TGF-beta receptor, enabling them to associate with SMAD4. The resultant complex of SMAD2/SMAD3 and SMAD4 can now be translocated into the cell nucleus, where it can initiate the transcription of the TGF-beta-regulated genes directly or via other proteins (summarized in Itoh (2000) Eur J Biochem 267: 6954-6967; Shi (2003) Cell 113: 685-700).

The spectrum of the functions of TGF-beta is wide-ranging and dependent on cell type and differentiation status (Roberts (1990) Handbook of Experimental Pharmacology: 419-472). The cellular functions which are influenced by TGF-beta include: apoptosis, proliferation, differentiation, mobility and cell adhesion. Accordingly, TGF-beta plays an important role in a very wide variety of biological processes. During embryo development, it is expressed at sites of morphogenesis and in particular in areas with epithelial-mesenchymal interaction, where it induces important differentiation processes (Pelton (1991) J Cell Biol 115:1091-1105). TGF-beta also carries out a key function in the self-renewal and maintenance of an undifferentiated state of stem cells (Mishra (2005) Science 310: 68-71). In addition, TGF-beta also fulfils important functions in the regulation of the immune system. It generally has an immunosuppressive action, since it inhibits, inter alia, the proliferation of lymphocytes and restricts the activity of tissue macrophages. TGF-beta thus allows inflammatory reactions to subside again and thus helps to prevent excessive immune reactions (Bogdan (1993) Ann NY Acad Sci 685: 713-739, summarized in Letterio (1998) Annu Rev Immunol 16: 137-161). Another function of TGF-beta is regulation of cell proliferation. TGF-beta inhibits the growth of cells of endothelial, epithelial and haematopoietic origin, but promotes the growth of cells of mesenchymal origin (Tucker (1984) Science 226:705-707, Shipley (1986) Cancer Res 46:2068-2071, Shipley (1985) PNAS 82: 4147-4151). A further important function of TGF-beta is regulation of cellular adhesion and cell-cell interactions. TGF-beta promotes the build-up of the extracellular matrix by induction of proteins of the extracellular matrix, such as, for example, fibronectin and collagen. In addition, TGF-beta reduces the expression of matrix-degrading metalloproteases and inhibitors of metalloproteases (Roberts (1990) Ann NY Acad Sci 580: 225-232; Ignotz (1986) J Biol Chem 261: 4337-4345; Overall (1989) J Biol Chem 264: 1860-1869); Edwards (1987) EMBO J 6: 1899-1904).

The broad spectrum of action of TGF-beta implies that TGF-beta plays an important role in many physiological situations, such as wound healing, and in pathological processes, such as cancer and fibrosis.

TGF-beta is one of the key growth factors in wound healing (summarized in O'Kane (1997) Int J Biochem Cell Biol 29: 79-89). During the granulation phase, TGF-beta is released from blood platelets at the site of injury. TGF-beta then regulates its own production in macrophages and induces the secretion of other growth factors, for example by monocytes. The most important functions during wound healing include stimulation of chemotaxis of inflammatory cells, the synthesis of extracellular matrix and regulation of the proliferation, differentiation and gene expression of all important cell types involved in the wound-healing process.

Under pathological conditions, these TGF-beta-mediated effects, in particular the regulation of the production of extracellular matrix (ECM), can result in fibrosis or scars in the skin (Border (1994) N Engl J Med 331:1286-1292).

For the fibrotic diseases, diabetic nephropathy and glomeronephritis, it has been shown that TGF-beta promotes renal cell hypertrophy and pathogenic accumulation of the extracellular matrix. Interruption of the TGF-beta signaling pathway by treatment with anti-TGF-beta antibodies prevents expansion of the mesangial matrix, progressive reduction in kidney function and reduces established lesions of diabetic glomerulopathy in diabetic animals (Border (1990) 346: 371-374, Yu (2004) Kindney Int 66: 1774-1784, Fukasawah (2004) Kindney Int 65: 63-74, Sharma (1996) Diabetes 45: 522-530).

TGF-beta also plays an important role in liver fibrosis. The activation, essential for the development of liver fibrosis, of the hepatic stellate cells to give myofibroblasts, the main producer of the extracellular matrix in the course of the development of liver cirrhosis, is stimulated by TGF-beta. It has likewise been shown here that interruption of the TGF-beta signaling pathway reduces fibrosis in experimental models (Yata (2002) Hepatology 35:1022-1030; Arias (2003) BMC Gastroenterol 3:29).

TGF-beta also takes on a key function in the formation of cancer (summarized in Derynck (2001) Nature Genetics: 29: 117-129; Elliott (2005) J Clin One 23: 2078-2093). At early stages of the development of cancer, TGF-beta counters the formation of cancer. This tumor-suppressant action is based principally on the ability of TGF-beta to inhibit the division of epithelial cells. By contrast, TGF-beta promotes cancer growth and the formation of metastases at late tumor stages. This can be attributed to the fact that most epithelial tumors develop a resistance to the growth-inhibiting action of TGF-beta, and TGF-beta simultaneously supports growth of the cancer cells via other mechanisms. These mechanisms include promotion of angiogenesis, the immunosuppressant action, which supports tumor cells in avoiding the control function of the immune system (immunosurveillance), and promotion of invasiveness and the formation of metastases. The formation of an invasive phenotype of the tumor cells is a principal prerequisite for the formation of metastases. TGF-beta promotes this process through its ability to regulate cellular adhesion, motility and the formation of the extracellular matrix. Furthermore, TGF-beta induces the transition from an epithelial phenotype of the cell to the invasive mesenchymal phenotype (epithelial mesenchymal transition=EMT). The important role played by TGF-beta in the promotion of cancer growth is also demonstrated by investigations which show a correlation between strong TGF-beta expression and a poor prognosis. Increased TGF-beta level has been found, inter alia, in patients with prostate, breast, intestinal and lung cancer (Wikstrom (1998) Prostate 37: 19-29; Hasegawa (2001) Cancer 91: 964-971; Friedman (1995), Cancer Epidemiol Biomarkers Prev. 4:549-54).

Owing to the cancer-promoting actions of TGF-beta described above, inhibition of the TGF-beta signaling pathway, for example via inhibition of the TGF-beta type I receptor, is a possible therapeutic concept. It has been shown in numerous preclinical trials that interruption of the TGF-beta signaling pathway does indeed inhibit cancer growth. Thus, treatment with soluble TGF-beta type II receptor reduces the formation of metastases in transgenic mice, which develop invasive breast cancer in the course of time (Muraoka (2002) J Clin Invest 109: 1551-1559, Yang (2002) J Clin Invest 109: 1607-1615).

Tumor cell lines which express a defective TGF-beta type II receptor exhibit reduced tumor and metastatic growth (Oft (1998) Curr Biol 8: 1243-1252, McEachern (2001) Int J Cancer 91:76-82, Yin (1999) J Clin Invest 103: 197-206).

Conditions "characterized by enhanced TGF-$\beta$ activity" include those in which TGF-$\beta$ synthesis is stimulated so that TGF-$\beta$ is present at increased levels or in which TGF-$\beta$ latent protein is undesirably activated or converted to active TGF-$\beta$ protein or in which TGF-$\beta$ receptors are upregulated or in which the TGF-$\beta$ protein shows enhanced binding to cells or extracellular matrix in the location of the disease. Thus, in either case "enhanced activity" refers to any condition in which the biological activity of TGF-$\beta$ is undesirably high, regardless of the cause.

A number of diseases have been associated with TGF-$\beta$ overproduction.

Inhibitors of TGF-$\beta$ intracellular signaling pathway are useful treatments for fibroproliferative diseases. Specifically, fibroproliferative diseases include kidney disorders associated with unregulated TGF-$\beta$ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, sclerorma, dermatomyositis, eosinophilic fascitis, morphea, or those associated with the occurrence of Raynaud's syndrome. Lung fibroses resulting from excessive TGF-$\beta$ activity include adult respiratory distress syndrome, idiopathic pulmonary fibrosis, and interstitial pulmonary fibrosis often associated with autoimmune disorders, such as systemic lupus erythematosus and sclerorma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post-glaucoma drainage surgery are associated with TGF-$\beta$1 overproduction.

Fibrotic diseases associated with TGF-$\beta$1 overproduction can be divided into chronic conditions, such as fibrosis of the kidney, lung and liver, and more acute conditions, such as dermal scarring and restenosis (Chamberlain, J. Cardiovascular Drug Reviews, 19 (4): 329-344). Synthesis and secretion of TGF-$\beta$1 by tumor cells can also lead to immune suppression, as seen in patients with aggressive brain or breast tumors (Arteaga, et al. (1993) J. Clin. Invest. 92: 2569-2576). The course of Leishmanial infection in mice is drastically altered by TGF-$\beta$1 (Barral-Netto, et al. (1992) Science 257: 545-547). TGF-$\beta$1 exacerbated the disease, whereas TGF-$\beta$1 antibodies halted the progression of the disease in genetically susceptible mice. Genetically resistant mice became susceptible to Leishmanial infection upon administration of TGF-$\beta$1.

The profound effects of TGF-$\beta$1 on extracellular matrix deposition have been reviewed (Rocco and Ziyadeh (1991) in Contemporary Issues in Nephrology v. 23, Hormones, autocoids and the kidney. ed. Jay Stein, Churchill Livingston, N.Y. pp. 391-410; Roberts, et al. (1988) Rec. Prog. Hormone Res. 44: 157-197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGF-β1 has profound effects on the kidney. The accumulation of mesangial matrix in proliferative glomerulonephritis (Border, et al. (1990) Kidney Int. 37: 689-695) and diabetic nephropathy (Mauer et al. (1984) J. Clin. Invest. 74: 1143-1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90: 1814-1818). TGF-β1 is an important mediator in the genesis of renal fibrosis in a number of animal models (Phan, et al. (1990) Kidney Int. 37: 426; Okuda, et al. (1990) J. Clin. Invest. 86: 453). Suppression of experimentally induced glomerulonephritis in rats has been demonstrated by antiserum against TGF-β1 (Border, et al. (1990) Nature 346: 371) and by an extracellular matrix protein, decorin, which can bind TGF-β1 (Border, et al. (1992) Nature 360: 361-363).

Excessive TGF-β1 leads to dermal scar-tissue formation. Neutralizing TGF-β1 antibodies injected into the margins of healing wounds in rats have been shown to inhibit scarring without interfering with the rate of wound healing or the tensile strength of the wound (Shah, et al. (1992) Lancet 339: 213-214). At the same time there was reduced angiogenesis, a reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced by 90% by this thickening, and since most of the reduction in diameter is due to extracellular matrix rather than smooth muscle cell bodies, it may be possible to open these vessels to 50% simply by reducing extensive extracellular matrix deposition. In undamaged pig arteries transfected in vivo with a TGF-β1 gene, TGF-β1 gene expression was associated with both extracellular matrix synthesis and hyperplasia (Nebel, et al. (1993) Proc. Natl. Acad. Sci. USA 90: 10759-10763). The TGF-β1 induced hyperplasia was not as extensive as that induced with PDGF-BB, but the extracellular matrix was more extensive with TGF-β1 transfectants. No extracellular matrix deposition was associated with hyperplasia induced by FGF-1 (a secreted form of FGF) in this gene transfer pig model (Nebel (1993) Nature 362: 844-846).

There are several types of cancer where TGF-β1 produced by the tumor may be deleterious. MATLyLu rat prostate cancer cells (Steiner and Barrack (1992) Mol. Endocrinol. 6: 15-25) and MCF-7 human breast cancer cells (Arteaga, et al. (1993) Cell Growth and Differ. 4: 193-201) became more tumorigenic and metastatic after transfection with a vector expressing the mouse TGF-β1. TGF-β1 has been associated with angiogenesis, metastasis and poor prognosis in human prostate and advanced gastric cancer (Wikstrom et al. (1998) Prostate 37: 19-29; Saito et al. (1999) Cancer 86: 1455-1462). In breast cancer, poor prognosis is associated with elevated TGF-β (Dickson, et al. (1987) Proc. Natl. Acad. Sci. USA 84: 837-841; Kasid, et al. (1987) Cancer Res. 47: 5733-5738; Daly, et al. (1990) J. Cell Biochem. 43: 199-211; Barrett-Lee, et al. (1990) Br. J. Cancer 61: 612-617; King, et al. (1989) J. Steroid Biochem. 34: 133-138; Welch, et al. (1990) Proc. Natl. Acad. Sci. USA 87: 7678-7682; Walker, et al. (1992) Eur. J. Cancer 238: 641-644) and induction of TGF-β1 by tamoxifen treatment (Butta, et al. (1992) Cancer Res. 52: 4261-4264) has been associated with failure of tamoxifen treatment for breast cancer (Thompson, et al. (1991) Br. J. Cancer 63: 609-614). Anti-TGF-β1 antibodies inhibit the growth of MDA-231 human breast cancer cells in athymic mice (Arteaga, et al. (1993) J. Clin. Invest. 92: 2569-2576); the treatment is correlated with an increase in spleen natural killer cell activity. CHO cells transfected with latent TGF-β1 also showed decreased NK activity and increased tumor growth in nude mice (Wallick, et al. (1990) J. Exp. Med. 172: 1777-1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328: 1592-1598). Patients with high circulating TGF-β before high dose chemotherapy and autologous bone marrow transplantation are at high risk of hepatic veno-occlusive disease (15-50% of all patients with a mortality rate up to 50%) and idiopathic interstitial pneumonitis (40-60% of all patients). The implication of these findings is 1) that elevated plasma levels of TGF-β1 can be used to identify at-risk patients and 2) that reduction of TGF-β1 could decrease morbidity and mortality of common treatments for breast cancer patients.

Many malignant cells secrete transforming growth factor β (TGF-β), a potent immunosuppressant, suggesting that TGF-β production may represent a significant tumor escape mechanism from host immunosurveillance. Establishment of a leukocyte subpopulation with disrupted TGF-β signaling in the tumor-bearing host offers a potential means for immunotherapy of cancer. A transgenic animal model with disrupted TGF-β signaling in T cells is capable of eradicating a normally lethal TGF-β overexpressing lymphoma tumor, EL4 (Gorelik and Flavell, (2001) Nature Medicine 7 (10): 1118-1122).

Downregulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerated host. The immunosuppressive effects of TGF-β have also been implicated in a subpopulation of HIV patients with lower than predicted immune response based on their CD4/CD8 T cell counts (Garba, et al. J. Immunology (2002) 168: 2247-2254). A TGF-β neutralizing antibody was capable of reversing the effect in culture, indicating that TGF-β signaling inhibitors may have utility in reversing the immune suppression present in this subset of HIV patients.

During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. The dual tumor suppression/tumor promotion roles of TGF-β have been most clearly elucidated in a transgenic system overexpressing TGF-β in keratinocytes. While the transgenics were more resistant to formation of benign skin lesions, the rate of metastatic conversion in the transgenics was dramatically increased (Cui, et al (1996) Cell 86 (4): 531-42). The production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β1 on cell/cell and cell/stroma interactions result in a greater propensity for invasion and metastasis.

Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities, such as radiation therapy and chemotherapy, induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β-mediated signal transduction might be a very effective therapeutic strategy. The resistance of tumor cells to TGF-β has been shown to negate many of the cytotoxic effects of radiation therapy and chemotherapy, and the treatment-dependent activation of TGF-β in the stroma may even be detrimental as it can make the microenvironment more conducive to tumor progression and contributes to tissue damage leading to fibrosis. The development of a TGF-β signal transduction inhibitors is likely to benefit the treatment of progressed cancer alone and in combination with other therapies.

The compounds are suitable for the treatment of cancer and other disease states influenced by TGF-β by inhibiting TGF-β in a patient in need thereof by administration of said compound(s) to said patient. TGF-β would also be useful against atherosclerosis (T. A. McCaffrey: TGF-ps and TGF-β Receptors in Atherosclerosis: Cytokine and Growth Factor Reviews 2000, 11, 103-114) and Alzheimer's (Masliah, E.; Ho, G.; Wyss-Coray, T.: Functional Role of TGF-β in Alzheimer's Disease Microvascular Injury: Lessons from Transgenic Mice Neurochemistry International 2001, 39, 393-400) diseases.

Another key biochemical mechanism of signal transduction involves the reversible phosphorylation of tyrosine residues on proteins. The phosphorylation state of a protein may affect its conformation and/or enzymatic activity as well as its cellular location. The phosphorylation state of a protein is modified through the reciprocal actions of protein tyrosine kinases (PTKs) and protein tyrosine phosphatases (PTPs) at various specific tyrosine residues.

Protein tyrosine kinases comprise a large family of transmembrane receptor and intracellular enzymes with multiple functional domains. The binding of ligand allosterically transduces a signal across the cell membrane where the cytoplasmic portion of the PTKs initiates a cascade of molecular interactions that disseminate the signal throughout the cell and into the nucleus. Many receptor protein tyrosine kinase (RPTKs), such as epidermal growth factor receptor (EGFR) and platelet-derived growth factor receptor (PDGFR) undergo oligomerization upon ligand binding, and the receptors self-phosphorylate (via autophosphorylation or transphosphorylation) on specific tyrosine residues in the cytoplasmic portions of the receptor. Cytoplasmic protein tyrosine kinases (CPTKs), such as Janus kinases (e.g. JAK1, JAK2, TYK2) and Src kinases (e.g. src, lck, fyn), are associated with receptors for cytokines (e.g. IL-2, IL-3, IL-6, erythropoietin) and interferons, and antigen receptors. These receptors also undergo oligomerization and have tyrosine residues that become phosphorylated during activation, but the receptor polypeptides themselves do not possess kinase activity.

Like the PTKs, the protein tyrosine phosphatases (PTPs) comprise a family of transmembrane and cytoplasmic enzymes, possessing at least an approximately 230 amino acid catalytic domain containing a highly conserved active site with a consensus motif. The substrates of PTPs may be PTKs which possess phosphotyrosine residues or the substrates of PTKs.

The levels of tyrosine phosphorylation required for normal cell growth and differentiation at any time are achieved through the coordinated action of PTKs and PTPS. Depending on the cellular context, these two types of enzymes may either antagonize or cooperate with each other during signal transduction. An imbalance between these enzymes may impair normal cell functions leading to metabolic disorders and cellular transformation.

It is also well known, for example, that the overexpression of PTKs, such as HER2, can play a decisive role in the development of cancer and that antibodies capable of blocking the activity of this enzyme can abrogate tumor growth. Blocking the signal transduction capability of tyrosine kinases such as Flk-1 and the PDGF receptor have been shown to block tumor growth in animal models.

Proteins which bind ATP and utilize its energy to change conformation, to phosphorylate substrates, and to initiate signaling cascades are known from many classes, like kinases, phosphatases, chaperones or isomerases. With specific tools and techniques ATP-binding proteins can be enriched.

From the large family of protein kinases, split into subfamilies of tyrosine kinases and serine threonine kinases, a partial list includes cAbl, Akt, ALK, ALK1 and its family members like ALK1 and ALK5, Axl, Aurora A and B, Btk, Dyrk2, EGFR, Erk, Ephrin receptors like EphA2, FAK, FGF receptors like FGFR3, insulin receptor IR and insulin like growth factor receptor IGF1R, IKK2, Jak2, JNK3, cKit, LimK, VEGF receptors 1, 2, and 3, Mek1, Met, P70s6K, PDGFR, PDK1, PI3K, Plk1, PKD1, bRaf, RSK1, Src and its family members, TAK1, Trk A, B, C, Zap70. The different kinases can be described under several synonyms, well known to the one skilled in the art and accessible in data bases like Kinweb to find a gene and protein report with alternative names, classification, gene annotation, sequence and gene structure, and links to the pdb 3D structure information. Similarly, proteomics server will give access to a lot of information and analysis and prediction tools for genes and proteins, including kinases.

As a mechanistic part of the hallmarks of cancer, Ser/Thr kinases and receptor tyrosine kinases (RTK) are phosphorylating enzymes essential in cellular signaling. Cell cycle, survival, proliferation and cell death are cellular processes, regulated by cell signaling, to permit tissue to grow, to regenerate and to be in homeostasis, or to regress. Some kinases are therefore exquisite targets for mammalian therapy.

Of the different families of kinases, which are part of the human kinome the receptor tyrosine kinase KDR, also called VEGF receptor 2, can stimulate endothelial cell survival and proliferation if ligated extra cellular by VEGF. Ligand binding can then lead to intracellular phosphorylation events, a signaling cascade and ultimately to proliferation. Inhibition of this KDR signaling is attempted by various therapies.

Other kinases and ligands important for function of endothelial cells are TIE2 kinase and the angiopoietins, PDGF receptor and PDGF as well as PIGF. Ephrin receptor kinase and ephrins, especially EphB4 and ephrin-B2. In addition, the ligand TGFβ and its receptors TGFβR, i.e. Alk1/Alk5 play an important role in maintenance of vascular integrity. By binding to the TGFβ type II receptor TGFβ can activate 2 distinct type I receptors in endothelial cells, i.e. the EC-restricted ALK1 and the broadly expressed ALK5 with opposite effects on EC behaviour. ALK1 stimulates EC proliferation and migration via Smad1/5 transcription factors, ALK5 inhibits thoses functions via Smad2/3 transcription factors. One example for an Alk5 kinase inhibitor that facilitates EC proliferation and sheet formation is SB-431542. Ligand binding inhibition might be an additional approach to modulate TGFβ receptor signalling also in angiogenesis. This was shown with 2 peptides and also discussed for soluble TGFβ receptor sTβR-Fc. Use of anti-TGFβ antibodies, even a TGFβ trap, would be another strategy to inhibit TGFβ signaling.

The TGFβ proteins comprise a family of conserved dimeric proteins with a molecular weight of ~25 kDa, which are ubiquitously expressed and secreted in an inactive form. Local proteolysis in response to appropriate stimuli leads to active TGFβ ligands. TGFβ signaling is implicated in numerous conditions and diseases, including cancer, cardiovascular, bone, CNS, PNS, inflammatory and neurodegenerative disorders.

In epithelial cells, TGFβ inhibits cell proliferation. The transition of normal epithelial cell into carcinoma cells is accompanied by down-regulation of the growth-inhibition response to TGFβ, allowing the cells to escape the autocrine tumor suppressor activities of TGFβ signaling. The increased production of TGFβ by carcinoma cells contributes to the invasive and metastatic behavior of the cancer cells. TGFβ can induce an epithelial-to-mesenchymal transition (EMT) that allows the cells to become invasive and migratory. In addition, the increased TGFβ production exerts effects on stromal and immune cells to provide a favourable microenvironment for cancer progression. TGFβ proteins signal through TβR-I/II receptor kinases and their Smad substrates, but can also signal independent of Smads, such as ERK MAP kinases, PI3 kinase, Rho-like GTPases, protein phosphatase 2A, and Par6. Activated type I TβR kinases enhance survival of cells and can accelerate pathological cell progression.

TGFβ receptor type I and II (TβR I, TβR II) are single-pass transmembrane-spanning intracellular serine/threonine kinases presenting extracellular ligand (TGFβ) binding receptors. Intra-cellular signaling proceeds via auto-phosphorylation, trans-phosphorylation and substrate phosphorylation, leading to modulation of target gene expression. Cloning and genomic organization of TβR proteins is well-known. TβR sequences are deposited in www.uniprot.org as TGFR1_human with accession number P36897, and as TGFβR2_human with accession number P37173. On protein level, type I TβR is described to contain a region rich in Gly and Ser (GS domain) preceeding the receptor kinase domain. TβR II is in its auto/phosphorylated state a constitutively active kinase which binds to the type I receptor and phosphorylates it in the GS domain.

TβReceptor, a ligand TGFβ-bound (activated) tetrameric complex of 2 TβR I and 2 TβR II units, is able to phosphorylate Smads (Smad 2 and Smad 3) in their C-terminal SSXS motifs as substrates which in turn are bound to/by Smad4 to be translocated to the cell nucleus, where they modulate TGFβ responsive genes. The different domains which regulate homomeric and heteromeric complex formation among type I and type II TβRs are known. Mutations in the GS domain of TβR I can be constitutively activating. Kinase inactivating mutation were found with K232R for type I and K277R for type II TβR. Inactivating or attenuating mutations in the genes for Type I and Type II TβR genes are found in a variety of cancers. In addition, signaling of TβRs is regulated by phosphorylation and dephosphorylation mechanisms, ubiquitinylation and sumoylation, and by endocytosis and by TACE-mediated ectodomain shedding of type I, but not type II receptors TACE, aka ADAM-17, which mediates shedding of cytokines, GF receptors, and adhesion proteins and is highly expressed in cancers.

The X-ray co-crystal structure of TβR I and FKBP12 has been described, and the kinase activation process was discussed. Meanwhile, several crystal structures can be found in the PDB data base: 1B6C, 1IAS, 1PY5, 1RW8, 1VJY, 2PJY, and a model 1TBI. For TβR II only X-ray studies for the extracellular ligand binding domain are known to the public: 1 KTZ, 1M9Z, and 1PLO (NMR), but none of the kinase domain.

TGFβ signal transduction involves Smads, the only substrates for TβR type I receptor kinases. The human genome encodes eight Smads from 3 subfamilies (R-, Co-, I-Smads), which are ubiquitously expressed throughout development and in adult tissue. Smads not only are phosphorylated by Type I TGFβ receptor kinases but they are also regulated by oligomerisation, ubiquitinylation and degradation, and nucleoplasmatic shuttling.

It was shown that VEGF release is regulated by ALK1 and ALK5, whereas TGFβ enhanced and BMP-9 suppressed expression of VEGF.

Studies with truncated ALK4 isoforms suggest involvement of this type I kinase in growth and development of pituitary tumors, by a dominant negative inhibition of activin signalling. Studies of the spatiotemporal window of roles of ALK4 in embryonic development, regulation of the mesoderm induction, primitive streak formation, gastrulation, primary axis formation and left-right axis determination are still not clarifying the role of ALK4 in adult.

In a large scale human candidate screen it was found that dominant-negative ALK2 alleles are associated with congenital heart disease, like improper atrioventrikular septum development.

ALK1 binds TβR-II and Endoglin/CD105/TβR-III and phosphorylates SMAD-1 and -5. The role of endoglin and especially the differential modulation of TGFβ signaling by two variants, L- and S-endoglin, has been shown. ALK1 functions in vascular remodelling and is found with ALK5 in balancing the activation state of endothelium in inflamed tissue, wounds and tumor. ALK1 is expressed in lung, placenta, and other highly vascularized tissue, and is selectively found on ECs. In addition, ALK1 was detected on neurons.

Loss of expression of type II TβR correlates with high tumor grade in human breast carcinomas, indicating a contribution to beast cancer progression. Tumor growth can be characterized by deregulated i.e. autonomous cell growth due to perturbation of RTK signaling by mutations or other genetic alterations. Of the 32000 human coding genes which are involved in signal transduction, more than 520 protein kinases and 130 protein phosphatases exert tight and reversible control on protein phosphorylation. Selectivity is found for tyrosine and for serine/threonine phosphorylation. There are more than 90 known PTK genes in the human genome, more than 50 encode transmembrane RPTKs distributed in 20 subfamilies, and 32 encode cytoplasmic, non-receptor PTKs in 10 subfamilies. For example Trk A has an important role in thyroid carcinomas and neuroblastomas, EphB2 and B4 are over-expressed in carcinomas, Axl and Lck are over-expressed in leukemia.

TGFβ inhibitors for the treatment of cancer were reviewed. There are further indications and pathologies, indirect targeting cancer, wound healing and inflammation via anti-angiogenesis, blood vessel formation, stabilization, maintenance and regression.

Angiogenesis, the development of new vessels from pre-existing vessels, is critical in vascular development in embryogenesis, organogenesis, and wound healing. In addition to those physiological processes, angiogenesis is important for tumor growth, metastasis and inflammation, resulting in diseases like tumors of the breast, uterine cervix, uterine corpus (endometrium), ovary, lung, bronchus, liver, kidney, skin, oral cavity and pharynx, prostate, pancreas, urinary bladder, blood cells, colon, rectum, bone, brain, central and peripheral nervous system, exemplified as breast cancer, colorectal cancer, gliomas, lymphomas, and so on, and of inflammatory diseases like rheumatoid arthritis and psoriasis, or diseases of the eye, like macula degeneration, and diabetic retinopathy. Molecular mechanisms of blood vessel formation and the angiogenic switch in tumorigenesis were recently discussed. Vascular patterning is regulated by Eph receptor tyrosine kinases and ephrin ligands, e.g. ephrin-B2 signaling via Eph B4 and Eph B1. EphB4 controls vascular morphogenesis during postnatal angiogenesis. The maturation of nascent vasculature, formed by angiogenesis or vasculogenesis, requires mural cells (pericytes, smooth muscle cells), generation of extracellular matrix and specialization of the vessel wall for structural support and regulation of vessel function. Regulation of those processes and interaction between endothelial cells and their mural cells involves several ligand kinase pairs, like VEGF/VEGFR1, VEGFR2, EphrinB2/EphB4, PDGFR/PDGFRβ, Angiopoietins/TIE2, TGFβ/TGFβR-ALK1/ALK5. Vessel assembly, capillary formation, sprouting, stabilization and destabilization, even regression, is regulated by a functional balance of those kinases and ligands. Lymphangiogenesis is regulated via VEGF receptor 3 and its ligands VEGF C, and D, as well as TIE2 and its ligands angiopoietins 1, 2. Inhibition of VEGFR3 and/or TIE2 signaling and therefore inhibition of formation of lymphatic vessels can be a mean to stop metastasis of tumor cells. The whole body of information about pathological vascularisation leads to the assumption for inhibition of angiogenesis being a promising strategy for treatment of cancer and other disorders.

The importance of TGFβ receptors for angiogenic processes is shown by Alk1, endoglin, Alk5 and TβRII KO mice all exhibiting an embryonic lethal phenotype due to vascular defects. In addition, in ECs TGFβ ligands are able to stimulate two pathways, with Smad 1/5/8 posphorylation downstream of Alk1 and Smad2/3 phosphorylation downstream of Alk5. Both pathways an cross-talk with each other. Alk5 knock-in mice with L45 loop mutations show defective Smad activation. TGFβ/Alk5 signaling is antagonized by ALK1 in ECs.

TGFβ exists in at least five isoforms (TGFβ1-5), which are not related to TGFa, with TGFβ1 as the prevalent form. TGFβ is a ubiquitous and essential regulator of cellular and physiological processes including proliferation, differentiation, migration, cell survival, angiogenesis and immunosurveillance.

Since cancer cells express tumor-specific antigens they normally would be recognized by the immune system and would be destroyed. During tumorigenesis cancer cells acquire the ability to evade this immunosurveillance by multiple mechanisms. A major mechanism is cancer cell mediated immunosuppression by secretion of TGFβ, a potent immunosuppressive cytokine. TGFβ has the potential to switch from being a tumor suppressor to a tumor promoter and prometastatic factor.

TGFβ function is transmitted by a tetrameric receptor complex, consisting of two groups of transmembrane serine-threonine kinase receptors, called type I and type II receptors, which are activated following engagement of members of the TGFβ superfamily of ligands, which is divided in 2 groups, the TGFβ/Activin and BMP/GDF branches. TGFβ1, 2, and 3 belong to the TGFβ/Activin branch of ligands. These binding events specify downstream responses that are differentially regulated in different cell types.

Importance of fibroblasts in mesenchymal-epithelial interaction in skin during wound repair was described in an inducible postnatal deletion of TGFβ RII in skin fibroblasts. During wound repair, expression of the ligand TGFβ and its receptor types RI and RII are timely and spatially regulated. CD109, a GPI linked cell surface antigen, expressed by CD34+ acute myeloid leukemia cell lines, ECs, activated platelets and T-cells are part of the TβR system in human keratinocytes. Follicle Stem Cells (FSCs) in the bulge region of hair follicle can give rise to multiple lineages during hair cycle and wound healing. Smad4, a common mediator of TGFβ signaling is part of FSCs maintenance. Smad4 KO studies in mouse skin showed hair follicle defects and squamous cell carcinoma formation. The potential suppression of TGFβ delayed catagen progression in hair follicles. The well described role of TGFβ in keratinocyte apoptosis during catagen phase is likely to involve anagen-specific hair follicle components also involving colocalized TβRI and TβRII.

Abnormal activity of TGFβ in fibrosis of several organs, such as skin, kidney, heart and liver, is known, being a rational for use of TβR inhibitors in fibrotic diseases. Systemic sclerosis (scleroderma), a complex disorder of connective tissue leading to fibrosis of the skin and inner organs, was shown to be TGFβ/receptor RI dependent. Pulmonary arterial hypertension (PAH) is a condition potentially treatable with ALK5 inhibitors because abnormal proliferation of peripheral arterial smooth muscle cells is driven by activated TGFβ receptors. Treatment in rats was successful with SB525334. Benefit in rat was also shown with IN-1233. Renal fibrosis can lead to diabetes.

Beneficial side effects of TβR kinase inhibitor derivatives and a connection between TGFβ signaling and hepatitis C virus (HCV) replication is known. TGFβ signaling is discussed as an emerging stem cell target in metastatic breast cancer. TGFβ1, 2, 3 and their receptors are expressed in neurons, astrocytes and microglia. Improvement of pathological outcome with TGFβ signaling modulators can be expected. The TGFβ superfamily in cardiovascular disease, like atherosclerosis, myocardial ischemia and cardiac remodeling is focus of an issue of cardiovascular research.

It has been found that the compounds according to the invention and salts thereof have very valuable pharmacological properties while being well tolerated. In particular, they exhibit TGF-β receptor I kinase-inhibiting properties.

The compounds according to the invention preferably exhibit an advantageous biological activity, which is easily demonstrated in enzyme-based assays, for example assays as described herein. In such enzyme-based assays, the compounds according to the invention preferably exhibit and cause an inhibiting effect, which is usually documented by IC50 values in a suitable range, preferably in the micromolar range and more preferably in the nanomolar range.

As discussed herein, these signaling pathways are relevant for various diseases. Accordingly, the compounds according to the invention are useful in the prophylaxis and/or treatment of diseases that are dependent on the said signaling pathways by interaction with one or more of the said signaling pathways. The present invention therefore relates to compounds according to the invention as promoters or inhibitors, preferably as inhibitors, of the signaling pathways described herein. The invention therefore preferably relates to compounds according to the invention as promoters or inhibitors, preferably as inhibitors, of the TGF-β☐ signaling pathway.

The present invention furthermore relates to the use of one or more compounds according to the invention in the treatment and/or prophylaxis of diseases, preferably the diseases described herein, that are caused, mediated and/or propagated by an increased TGF-β☐activity. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases as well as to a method for the treatment of the said diseases comprising the administration of one or more compounds according to the invention to a patient in need of such an administration.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilized in order to modulate the signal (e.g. Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintilla-tion proximity assay (Sorg et al., J. of. Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence reso-nance energy transfer (HTR-FRET) and fluorescence polarisation (FP) technologies are suitable as assay methods (Sills et al., J. of Biomolecular Screening, 2002, 191-214). Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody.

Several prior references relate to the synthesis of quinoline derivatives. WO 06/058201 A2 describes 2-aryl-4-arylamino quinolines (and quinazoline and isoquinolines), but does not teach the synthesis and use of a 4-pyridyl-amino(4) substitution. WO 04/081009 A1 describes several quinazolines and 3-F quinolines all substituted with a bicyclic aza indoline or tetrahydro naphthyridine system in position 4, but does not teach the synthesis and use of a quinoline system with unmodified position 3. WO 03/018561 A1 describes the use of quinolines for calcium channel blockers. WO 05/030129 A2 is directed to potassium channel inhibitors. The 4-amino quinolines of WO 00/076982 A1 are applied in immune modulation. None of the latter 3 citations describes the pharmacophoric decoration of a quinoline optimized for TβR inhibition.

The invention relates to compounds of formula (I)

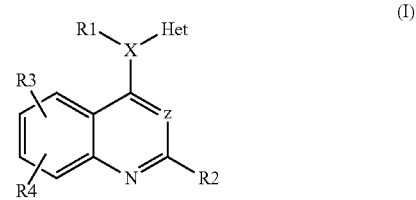

wherein
X denotes N, —N(CO)—, S, O, Alk or —N(Alk)-;
Z denotes CH or N;
Het denotes

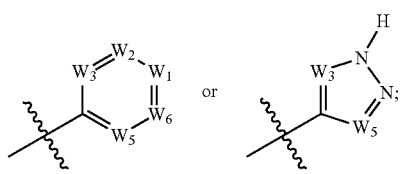

W1 denotes N or CR7;
W2 denotes N or CR6;
W3 denotes N or CR5;
W5 denotes N or CR9;
W6 denotes N or CR8;
R1 denotes H, A, Het$^1$, Het$^2$; Het$^3$, Ar, —COA, —CO-Het$^3$, Alk-COOY or Cyc;
R5 denotes H, A, Hal, OY, CN, -Alk-OY, COOY, —CO—NYY, SA, SO$_2$A, NYY, —OAlk-OYY, NO$_2$, —NH-Alk-COOY, —NH—CO-Alk-OY, —NH—CO-Alk-OCOY, —NH—CO-Alk-NYY, —NH—CO—NYY, —NH—CO-Het$^3$, —NH—SO$_2$—NYY, —NH—SO$_2$—(NYY)$_2$, —NH—SO$_3$H, —NH—SO$_2$-Alk-Y, —NH-Het$^2$, —NH—R2, —CO—NH-Alk-NYY, —CO—R2, —CO—NY—R2, —OCO—R2, —SO$_2$—R2, —SO$_2$—NY—R2 or Het$^3$;
R1, R5 together also denote —CH=CH—, —C(Y)=N—, —C(Alk-NYY)=N—, —C(Alk-OY)=N—, —C(Het$^3$)=N—, —CO—N(COOY)—, —C(CO—R2)=N—, —CH(CO-Het$^2$)-, —(CO)$_2$—N(Y)—, —CO—NH—, —NH—CO—, —NH—COA-, —SO$_2$—NH—, —NH—SO$_2$— or —NH—SO$_2$—N(SO$_2$)—;

R6 denotes H, A, Hal, OY, CN, -Alk-OY, COOY, —CO—NYY, NYY, —NH-Alk-NYY, —NH—COA, —NH—CO-Alk-NYY, —NH—CO-Alk-NH—COOA, —NH—SO$_2$—NYY, —NH-Het$^2$ or Het$^3$;

R5, R6 together also denote =CH—C(Y)=C(Y)—CH=, —CH=CH—NH— or —N=CH—CH=CH—;

R7, R8, R9 denotes independently from one another H, A, Hal, OY, NYY, —NH—CO-Alk-NYY, —NH-Het$^2$ or Het$^3$;

R2 denotes Cyc, a monocyclic carboaryl having 5-8 C atoms or a monocyclic heteroaryl having 2-7 C atoms and 1-4 N, O and/or S atoms, each of which can be substituted by at least one substituent selected from the group of A, Hal, CN, NYY, OY, =O, Cyc, Alk-Ar;

R3, R4 denotes independently from one another H, A, Hal, CN, NYY, OY, —OAlk-NYY, —OAlk-OY, Het$^3$, or together —OAlk-O—;

Y denotes H, A, Hal or OA;

A denotes unbranched or branched alkyl having 1-10 C atoms, in which 1-7 H atoms can be replaced by Hal;

Cyc denotes cycloalkyl having 3-7 C atoms,
in which 1-4 H atoms can be replaced independently from one another by A, Hal and/or OY;

Alk denotes alkylene having 1-6 C atoms,
in which 1-4 H atoms can be replaced independently of one another by Hal and/or CN;

Ar denotes a saturated, unsaturated or aromatic, mono- or bicyclic
carbocycle having 6-10 C atoms,
which can be substituted by at least one substituent selected from the group of A, Hal, OY, COOY, -Alk-OY, -Alk-SO$_2$, -Alk-Het$^1$, —OAlk-Het$^1$, NYY, —CO—NYY, —SO$_2$NYY, CN;

Het$^1$ denotes a monocyclic heteroaryl having 2-7 C atoms and 1-4 N atoms, which can be substituted by at least one substituent selected from the group of —NH-Het$^3$, A, Hal, OY, COOY, -Alk-OY, -Alk-SO$_2$, NYY, —CO—NYY, —SO$_2$NYY, CN;

Het$^2$ denotes a bicyclic heteroaryl having 2-9 C atoms and 1-4 N atoms,
which can be substituted by at least one substituent selected from the group of R2, A, Hal, OY, COOY, -Alk-OY, -Alk-SO$_2$, NYY, —CO—NYY, —SO$_2$NYY, CN;

Het$^3$ denotes an saturated monocyclic heterocycle having 2-7 C atoms and 1-4 N, O and/or S atoms,
which can be substituted by at least one substituent selected from the group of A, Hal, OY, COOY, -Alk-OY, -Alk-SO$_2$, NYY, —CO—NYY, —SO$_2$NYY, CN;
and
Hal denotes F, Cl, Br or I;
and/or physiologically acceptable salts thereof.

For the sake of clarity, R1; R5; R6; R1, R5 together; R5, R6 together have the indicated meaning under the proviso that (i) R1; R5 together and R5, R6 together are absent if R1; R5 and R6 have the indicated meaning, (ii) R1; R5 and R5, R6 together are absent if R1, R5 together and R6 have the indicated meaning, and (iii) R1, R5 together; R5 and R6 are absent if R1 and R5, R6 together have the indicated meaning;

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as "pure" E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. YY) the expression of such substituent may differ from each other (e.g. methyl and ethyl). It shall be understood accordingly that a multiple substitution of any radical of the invention may involve identical or different radicals. Hence, if individual radicals occur a number of times within a compound, the radicals adopt the meanings indicated, independently of one another.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, "A" denotes unbranched or branched alkyl having 1-10 C atoms, in which 1-7 H atoms may be replaced by Hal. A more preferred "A" denotes unbranched or branched alkyl having 1-4 C atoms, in which 1-5 atoms may be replaced by F and/or Cl. Most preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl or trifluoromethyl. It is a highly preferred embodiment of the invention that "A" denotes methyl. It shall be understood that the respective denotation of "A" is independently of one another in the radicals R1 to R9, Y, Cyc, Ar, Het$^1$, Het$^2$ and Het$^3$.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, "Cyc" denotes cycloalkyl having 3-7 C atoms, in which 1-4 H atoms may be replaced independently of one another by A, Hal and/or OY. More preferred is $C_5$-$C_7$-cycloalkyl, in which one H atom may be replaced by A, Hal, OH or OA. A highly preferred $C_5$-$C_7$-cycloalkyl radical is unsubstituted, i.e. cyclopentyl, cyclohexyl or cycloheptyl, preferably cyclohexyl. It shall be understood that the respective denotation of "Cyc" is independently of one another in the radicals R1 and R2.

The term "Alk" refers to unbranched or branched alkylene, alkenyl or alkynyl having 1, 2, 3, 4, 5 or 6 C atoms, i.e. $C_1$-$C_6$-alkylenes, $C_2$-$C_6$-alkenyls and $C_2$-$C_6$-alkynyls. Alkenyls have at least one C—C double bond and alkynyls at least one C—C triple bond. Alkynyls may additionally also have at least one C—C double bond. Example of suitable alkylene radicals are methylene, ethylene, propylene, butylene, pentylene, hexylene, isopropylene, isobutylene, sec-butylene, 1-2- or 3-methylbutylene, 1,1-, 1,2- or 2,2-dimethylpropylene, 1-ethylpropylene, 1-, 2-, 3- or 4-methylpentylene, 1,1-, 1,2-, 1,3-, 2,2-, 2,3- or 3,3-dimethyl-butylene, 1- or 2-ethylbutylene, 1-ethyl-1-methylpropylene, 1-ethyl-2-methylpropylene, 1,1,2- or 1,2,2-trimethylpropylene. Example of suitable alkenyls are allyl, vinyl, propenyl (—$CH_2CH$=$CH_2$; —CH=CH—$CH_3$; —C(=$CH_2$)—$CH_3$), 1-, 2- or 3-butenyl, isobutenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl and hexenyl. Example of suitable alkynyls are ethynyl, propynyl (—$CH_2$—C≡CH; —C≡C—$CH_3$), 1-, 2- or 3-butynyl, pentynyl, hexynyl and or pent-3-en-1-in-yl, particularly propynyl.

In a preferred embodiment of the invention, "Alk" denotes unbranched or branched alkylene having 1-6 C atoms, in which 1-4 H atoms may be replaced independently of one another by Hal and/or CN. A more preferred "Alk" denotes unbranched alkylene having 1-6 C atoms, i.e. methylene, ethylene, propylene, butylene, pentylene or hexylene, in which 1-2 H atoms may be replaced by F and/or Cl. Most preferred is $C_{1-3}$-alkylene; particular examples of which are methylene, ethylene and propylene. It is a highly preferred embodiment of the invention that "Alk" denotes methylene or ethylene. It shall be understood that the respective denotation of "Alk" is independently of one another in the radicals X, R1 to R9, Ar, Het$^1$, Het$^2$ and Het$^3$.

The term "aryl" or "carboaryl" for the purposes of this invention refers to a mono- or polycyclic aromatic hydrocarbon systems having 3 to 14, preferably 4 to 10, more preferably 5 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula (I) can be effected via any possible ring member of the aryl radical. Examples of suitable "aryl" radicals are phenyl, biphenyl, naphthyl, 1-naphthyl, 2-naphthyl and anthracenyl, but likewise in-danyl, indenyl or 1,2,3,4-tetrahydronaphthyl.

Preferred "carboaryls" of the invention are optionally substituted phenyl, naphthyl and biphenyl, more preferably optionally substituted monocylic carboaryl having 5-8 C atoms, most preferably optionally substituted phenyl, highly preferably optionally substituted phenyl if defined in terms of R2 radical. The preferred carboaryls of the invention can be substituted by at least one substituent selected from the group of A, Hal, CN, NYY, OY, =O, Cyc, Alk-Ar.

The term "heteroaryl" for the purposes of this invention refers to a 2-15, preferably 2-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, 3 or 4, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula (I) can be effected via any possible ring member of the heteroaryl radical. Examples of suitable "heteroaryl" are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that "heteroaryl" in the realms of R2 radical represents a monocyclic heteroaryl having 2-7 C atoms and 1 to 4 N, O and/or S atoms, which can be substituted by at least one substituent selected from the group of A, Hal, CN, NYY, OY, =O, Cyc, Alk-Ar. It is also preferred that "carboaryl" in the realms of R2 radical represents a monocyclic carboaryl having 5-8 C atoms, which can be monosubstituted by at least one substituent selected from the group of A, Hal, CN, NYY, OY, =O, Cyc, Alk-Ar. It is additionally preferred that R2 denotes Cyc, which is unsubstituted or can be substituted by at least one substituent selected from the group of A, Hal, CN, NYY, OY, =O, Cyc, Alk-Ar. Hence, the aforementioned heteroaryl, carboaryl and Cyc shall represent the preferred Markush group for the radical R2.

In a more preferred embodiment of the invention, the R2 radical denotes phenyl or a monocyclic 5-6 membered heteroaryl having 1-3 N atoms, each of which can be substituted by at least one substituent selected from the group of Hal, A, NAA, CN, OA. Herein, particular preference is given to the heteroaryls thiophenyl, furanyl, thiazolyl, imidazolyl, pyridyl, pyrazinyl or pyrazolyl, each of which can be substituted by as defined above. Subject to other substitutions, R2 denotes most preferably phenyl or pyridin-2-, 3-, 4- or 5-yl, each of which can be mono- or disubstituted by at least one substituent selected from the group of F, Cl, Br, $CH_3$, $CF_3$, CN, $OCH_3$. It is highly preferred that R2 is phenyl, pyridin-2-yl, 2-fluoro-phenyl, 2-fluoro-5-fluoro-phenyl, 2-fluoro-5-chloro-phenyl, 2-fluoro-5-bromo-phenyl, 2-fluoro-5-trifluoromethyl-phenyl, 2-chloro-phenyl, 2-chloro-5-chloro-phenyl, 3-chloro-phenyl, 3-trifluoromethyl-phenyl or 6-methyl-pyridin-2-yl.

It shall be understood that the respective denotation of "R2" is independently of one another in the radicals R2 itself, $Het^2$, R5 and R1, R5 together.

It is preferred that "heteroaryl" in the realms of "$Het^1$" represents a monocyclic heteroaryl having 2-7 C atoms and 1-4 N atoms, which can be substituted by at least one substituent selected from the group of —NH-$Het^3$, A, Hal, OY, COOY, -Alk-OY, -Alk-$SO_2$, NYY, —CO—NYY, —$SO_2$NYY, CN. In a more preferred embodiment of the invention, $Het^1$ denotes a monocyclic heteroaryl having 2-7 C atoms and 1-4 N atoms, which can be substituted by —NH-$Het^3$, A and/or Hal. In a most preferred embodiment of the invention, $Het^1$ denotes pyridine-4-amine, which is monosubstituted by $Het^2$. A highly preferred embodiment of the $Het^1$ radical is ([2-fluoro-5-chloro-phenyl]-quinolin-4-yl)-pyridin-2-yl-4-amine. It shall be understood that the respective denotation of "$Het^1$" is independently of one another in the radicals R1 and Ar.

It is preferred that "heteroaryl" in the realms of "$Het^2$" represents a bicyclic heteroaryl having 2-9 C atoms and 1-4 N atoms, which can be substituted by at least one substituent selected from the group of R2, A, Hal, OY, COOY, -Alk-OY, -Alk-$SO_2$, NYY, —CO—NYY, —$SO_2$NYY, CN. In a more preferred embodiment of the invention, $Het^2$ denotes a bicyclic heteroaryl having 2-9 C atoms and 1-4 N atoms, which can be substituted by R2, A and/or Hal. In a most preferred embodiment of the invention, $Het^2$ denotes quinoline, which is monosubstituted by R2. A highly preferred embodiment of the $Het^2$ radical is (2-fluoro-5-chloro-phenyl)-quinolin-4-yl. It shall be understood that the respective denotation of "$Het^2$" is independently of one another in the radicals R1, R5 to R9, $Het^1$ and R1, R5 together.

The terms "heterocycle" or "heterocyclyl" for the purposes of this invention refers to a mono- or polycyclic system of 3 to 20 ring atoms, preferably 3 to 14 ring atoms, more preferably 3 to 10 ring atoms, comprising carbon atoms and 1, 2, 3, 4 or 5 heteroatoms, which are identical or different, in particular nitrogen, oxygen and/or sulfur. The cyclic system may be saturated or mono- or poly-unsaturated. In the case of a cyclic system consisting of at least two rings the rings may be fused or spiro or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocyclyl radical. The bonding to the compounds of the general formula (I) can be effected via any possible ring member of the heterocyclyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In an aspect of the invention, "$Het^3$" denotes a saturated monocyclic heterocycle having 2-7 C atoms and 1-4 N, O and/or S atoms, which can be substituted by at least one substituent selected from the group of A, Hal, OY, COOY, -Alk-OY, -Alk-$SO_2$, NYY, —CO—NYY, —$SO_2$NYY, CN. In a preferred embodiment of the invention, $Het^3$ denotes a saturated monocyclic heterocycle having 2-7 C atoms and 1-4 N, O and/or S atoms, which can be substituted by by A, Hal, COOY and/or NYY. In a more preferred embodiment of the invention, $Het^3$ denotes piperazine, piperidine, morpholine, pyrrolidine, piperidone, morpholinone or pyrrolidone, which can be monosubstituted by A, Hal, COOY or NYY. Herein, "A" is especially methyl, ethyl, propyl, butyl, pentyl, hexyl, isopropyl or trifluoromethyl, and Hal is especially F, Cl or Br. It shall be understood that the respective denotation of "$Het^3$" is independently of one another in the radicals R1, R3 to R9, $Het^1$ and R1, R5 together.

In another embodiment of the invention, a "carbocycle", including, but not limited to, carboaryl, is defined as "Ar", which denotes a saturated, unsaturated or aromatic, mono- or bicyclic carbocycle having 3-10 C atoms, which can be mono-, di- or trisubstituted by at least one substituent selected from the group of A, Hal, COOY, OY, -Alk-OY, -Alk-$SO_2$, -Alk-$Het^{1/2/3}$, —OAlk-$Het^{1/2/3}$, NYY, —CO—NYY, —$SO_2$—NYY, CN, -Alk-NYY. Examples of suitable "Ar" radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)phenyl, o-, m- or p-(N-ethyl-N-methyl-sulfonamido)phenyl, o-, m- or p-(N,N-diethyl-sulfonamido)phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

In another preferred embodiment of the invention, the "Ar" radical denotes a saturated, unsaturated or aromatic, mono- or bicyclic carbocycle having 6-10 C atoms, which can be substituted by at least one substituent selected from the group of A, Hal, OY, COOY, -Alk-OY, -Alk-SO$_2$, -Alk-Het$^1$, —OAlk-Het$^1$, NYY, —CO—NYY, —SO$_2$NYY, CN. It shall be understood that the respective denotation of "Ar" is independently of one another in the radicals R1 and R2.

For the purposes of the present invention, the terms "alkylcycloalkyl", "cycloalkylalkyl", "alkylheterocyclyl", "heterocyclylalkyl", "alkylaryl", "arylalkyl", "alkylheteroaryl" and "heteroarylalkyl" mean that alkyl, cycloalkyl, heterocycl, aryl and heteroaryl are each as defined above, and the cycloalkyl, heterocyclyl, aryl or heteroaryl radical is bonded to the compounds of the general formula (I) via an alkyl radical, preferably $C_1$-$C_6$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula (I) is via the oxygen atom. Examples are methoxy, ethoxy, and n-propyloxy, propoxy and isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula (I) is via the oxygen atom. Examples are cyclopropyloxy, cyclobutyloxy, cyclopentyloxy, cyclohexyloxy and cycloheptyloxy. Preferred is "$C_3$-$C_7$-cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formula (I) is via the oxygen atom. Examples are pyrrolidinyloxy, thiapyrrolidinyloxy, piperidinyloxy and piperazinyloxy.

The term "aryloxy" for the purposes of this invention refers to an aryl radical according to above definition that is attached to an oxygen atom. The attachment to the compounds of the general formula (I) is via the oxygen atom. Examples are phenyloxy, 2-naphthyloxy, 1-naphthyloxy, biphenyloxy and indanyloxy. Preferred is phenyloxy.

The term "heteroaryloxy" for the purposes of this invention refers to a heteroaryl radical according to above definition that is attached to an oxygen atom. The attachment to the compounds of the general formula (I) is via the oxygen atom. Examples are pyrrolyloxy, thienyloxy, furyloxy, imidazolyloxy and thiazolyloxy.

The term "acyl" for the purposes of this invention refers to radicals that are formed by cleaving a hydroxyl group from acids. The attachment to the compounds of the general formula (I) is via the carbonyl C atom. Preferred examples are —CO-A, —SO$_2$-A and —PO(OA)$_2$, more preferably —SO$_2$-A.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine and chlorine are more preferred, when the halogens are substituted on an alkyl (haloalkyl) or alkoxy group (e.g. $CF_3$ and $CF_3O$).

The term "hydroxyl" means an —OH group.

It is a preferred embodiment of the X radical according to the present invention to be N.

It is a preferred embodiment of the Z radical according to the present invention to be CH.

It is a preferred embodiment of the Het radical according to the present invention to be

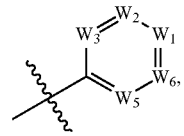

wherein at least one of W1, W2, W3, W5 or W6 denotes N. It goes without saying that R7, R6, R5, R9, R8 is independently from one another absent if W1, W2, W3, W5, W6 denotes independently from one another N. In a more preferred embodiment of the invention, Het denotes pyridyl, pyrimidinyl, triazinyl, pyridazinyl or pyrazyl, each of which can be substituted by R7, R6, R5, R9 and/or R8. For the sake of clarity and under the proviso that W1, W2, W3, W5, W6 does not denote independently from one another N, R7 is bond to the C atom of W1 (i.e. substituent in position 1), R6 is bond to the C atom of W2 (i.e. substituent in position 2), R5 is bond to the C atom of W3 (i.e. substituent in position 3), R9 is bond to the C atom of W5 (i.e. substituent in position 5) and R8 is bond to the C atom of W6 (i.e. substituent in position 6). The denotation of W1, W2, W3, W5 and W6 can be easily assigned by the skilled artisan to each N-heteroaryl in the meaning of the invention. In a particular embodiment of the invention, for example, W1 is N, W2 is CR6, W3 is CR5, W5 is CR9 and W6 is CR8, which corresponds to pyridin-4-yl with the N atom in position 1, which can be optionally substituted by R6 in position 2, R5 in position 3, R9 in position 5 and/or R8 in position 6. More particularly, 1-pyridin-4-yl can be mono- or disubstituted by R6 in position 2 and/or R5 in position 3.

In another particular embodiment of the invention, W1 is N, W2 is CR6, W3 is N, W5 is CR9 and W6 is CR8, which corresponds to 1,3-pyrimidin-4-yl, which can be optionally substituted by R6 in position 2, R9 in position 5 and/or R8 in position 6. More particularly, 1,3-pyrimidin-4-yl can be monosubstituted by R6 in position 2 or R8 in position 6. Most particularly, 1,3-pyrimidin-4-yl can be monosubstituted by R8 in position 6. It is considered to be equivalent to 1,5-pyrimidin-4-yl, which can be monosubstituted by R6 in position 2.

In still another particular embodiment of the invention, W1 is N, W2 is CR6, W3 is N, W5 is CR9 and W6 is N, which corresponds to 1,3,5-triazin-4-yl, which can be optionally mono- or disubstituted by R6 in position 2 and/or R8 in position 6. More particularly, 1,3,5-triazin-4-yl can be monosubstituted by R6 in position 2.

It is more preferred that 1-pyridin-4-yl, 1,3-pyrimidin-4-yl, 1,3,5-triazin-4-yl can be monosubstituted by R6 in position 2, R5 in position 3 and/or R8 in position 6. In a highly preferred embodiment of the invention, 1-pyridin-4-yl can be monosubstituted by R6 in position 2 and/or R5 in position 3.

It is a preferred embodiment of the R1 radical according to the present invention to be H or A, more preferably H.

It is a preferred embodiment of the R5 radical according to the present invention to be H, A, Hal, OY, CN, -Alk-OY, —CO—NYY, SA, SO$_2$A, NYY, —OAlk-OYY, NO$_2$, —NH-Alk-COOY, —NH—CO-Alk-OY, —NH—CO-Alk-OCOY, —NH—CO-Alk-NYY, —NH—CO—NYY, —NH—CO-Het$^3$, —NH—SO$_2$—NYY, —NH—SO$_2$—(NYY)$_2$, —NH—SO$_3$H, —NH—SO$_2$-Alk-Y, —NH-Het$^2$, —NH—R2, —CO—NH-Alk-NYY or Het$^3$. More preferably, R5 denotes H, A, OA, CN, -Alk-OY, —CO—NYY, SA, NYY, —NH—CO-Alk-OY, —NH—CO-Alk-OCOY, —NH—CO-Alk-NYY, —NH—CO—NYY, —NH—CO-Het$^3$, —NH—SO$_2$—NYY, —CO—NH-Alk-NYY or Het$^3$. Most preferably, R5 denotes H, A, OA, SA, NYY, —NH—CO-Alk-OY, —NH—CO-Alk-OCOY, —NH—CO-Alk-NYY, —NH—CO—NYY, —NH—CO-Het$^3$ or —NH—SO$_2$—NYY. Highly preferably, R5 denotes H, A, OA, NH$_2$ or —NH—SO$_2$—NH$_2$.

It is a preferred embodiment according to the present invention that R1 and R5 together also denote —CH═CH—, —C(Y)═N—, —C(Alk-NYY)═N—, —C(Alk-OY)═N—, —C(Het$^3$)═N—, —CO—N(COOY)—, —(CO)$_2$—N(Y)—, —CO—NH—, —NH—CO—, —NH—COA-, —SO$_2$—NH—, —NH—SO$_2$— or —NH—SO$_2$—N(SO$_2$)—. More preferably, R1 and R5 denote together —CH═CH—, —C(Y)═N—, —C(Alk-OY)═N—, —CO—N(COOY)—, —CO—NH— or —SO$_2$—NH—. Most preferably, R1 and R5 denote together —CO—NH—.

It is a preferred embodiment of the R6 radical according to the present invention to be H, A, Hal, OY, NYY, —NH-Alk-NYY, —NH—COA, —NH—CO-Alk-NYY, —NH-Het$^2$ or Het$^3$. More preferably, R6 denotes H, A, OA, NYY, —NH-Alk-NYY, —NH—COA or —NH—CO-Alk-NYY. Most preferably, R6 denotes H, A, OA, NYY, —NH—COA or —NH—CO-Alk-NYY. Highly preferably, R6 denotes H, A or NH$_2$.

It is a preferred embodiment according to the present invention that R5, R6 together also denote ═CH—CH═C(Y)—CH═, ═CH—C(Y)═CH—CH═ or —CH═CH—NH— or —N═CH—CH═CH—. More preferably, R1 and R5 denote together ═CH—CH═C(Y)—CH═ or —N═CH—CH═CH—.

It is a preferred embodiment of the R3 radical according to the present invention to be H.

It is a preferred embodiment of the R4 radical according to the present invention to be H.

It is a preferred embodiment of the R7 radical according to the present invention to be H.

It is a preferred embodiment of the R8 radical according to the present invention to be H.

It is a preferred embodiment of the R9 radical according to the present invention to be H.

It is a preferred embodiment of the Y radical according to the present invention to be H, A or OA.

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means, the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In another embodiment of the present invention, quinoline derivatives of formula (I) are provided,
wherein
X denotes N;
Het denotes pyridinyl, pyrimidinyl, triazinyl, pyridazinyl or pyrazyl, each of which can be substituted by R5, R6, R7, R8 and/or R9;
R1 denotes H or A,
R5 denotes H, A, Hal, OY, CN, -Alk-OY, —CO—NYY, SA, SO$_2$A, NYY, —OAlk-OYY, NO$_2$, —NH-Alk-COOY, —NH—CO-Alk-OY, —NH—CO-Alk-OCOY, —NH—CO-Alk-NYY, —NH—CO—NYY, —NH—CO-Het$^3$, —NH—SO$_2$—NYY, —NH—SO$_2$—(NYY)$_2$, —NH—SO$_3$H, —NH—SO$_2$-Alk-Y, —NH-Het$^2$, —NH—R2, —CO—NH-Alk-NYY or Het$^3$;
R1, R5 together also denote —CH═CH—, —C(Y)═N—, —C(Alk-NYY)═N—, —C(Alk-OY)═N—, —C(Het$^3$)═N—, —CO—N(COOY)—, —(CO)$_2$—N(Y)—, —CO—NH—, —NH—CO—, —NH—COA-, —SO$_2$—NH—, —NH—SO$_2$— or —NH—SO$_2$—N(SO$_2$)—;
R6 denotes H, A, Hal, OY, NYY, —NH-Alk-NYY, —NH—COA, —NH—CO-Alk-NYY, —NH-Het$^2$ or Het$^3$;
R5, R6 together also denote ═CH—CH═C(Y)—CH═, ═CH—C(Y)═CH—CH═, —CH═CH—NH— or —N═CH—CH═CH—;
R2 denotes phenyl or pyridyl,
each of which can be mono- or disubstituted by at least one substituent selected from the group of Hal, A, NAA, CN, OA;
Het$^1$ denotes a monocyclic heteroaryl having 2-7 C atoms and 1-4 N atoms, which can be substituted by —NH-Het$^3$, A and/or Hal.
Het$^2$ denotes a bicyclic heteroaryl having 2-9 C atoms and 1-4 N atoms, which can be substituted by R2, A and/or Hal.
Het$^3$ denotes an saturated monocyclic heterocycle having 2-7 C atoms and 1-4 N, O and/or S atoms, which can be substituted by A, Hal, COOY and/or NYY;
and
Z, R3, R4, R7; R8, R9, Y, A, Cyc, Alk, Hal have the meaning indicated above;
and/or physiologically acceptable salts thereof.

In a preferred embodiment of the present invention, quinoline derivatives of sub-formula (II) are provided,

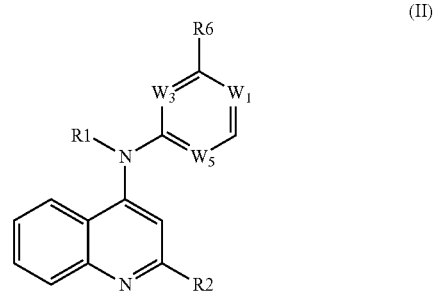

wherein

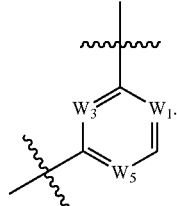

denotes pyridyl, which can be substituted by R5 if W3 is CR5, pyrimidinyl or triazinyl;

R1 denotes H;

R5 denotes H, A, OA, CN, -Alk-OY, —CO—NYY, SA, NYY, —NH—CO-Alk-OY, —NH—CO-Alk-OCOY, —NH—CO-Alk-NYY, —NH—CO—NYY, —NH—CO-Het³, —NH—SO₂—NYY, —CO—NH-Alk-NYY or Het³;

R1, R5 together also denote —CH=CH—, —C(Y)=N—, —C(Alk-OY)=N—, —CO—N(COOY)—, —CO—NH— or —SO₂—NH—;

R6 denotes H, A, OA, NYY, —NH-Alk-NYY, —NH—COA or —NH—CO-Alk-NYY;

R5, R6 together also denote =CH—CH=C(Y)—CH= or —N=CH—CH=CH—;

R7, R9 denotes independently from one another H if W1 is CR7 or W5 is CR9;

R2 denotes phenyl or pyridyl, each of which can be mono- or disubstituted by at least one substituent selected from the group of F, Cl, Br, CH₃, CF₃, CN, OCH₃;

Y denotes H, A or OA;

A denotes unbranched or branched alkyl having 1-4 C atoms, in which 1-5 H atoms can be replaced by F and/or Cl;

Alk denotes alkylene having 1-3 C atoms;

Het³ denotes piperazine, piperidine, morpholine, pyrrolidine, piperidone, morpholinone or pyrrolidone, which can be monosubstituted by A, Hal, COOY or NYY;

and

Hal denotes F, Cl or Br;

and/or physiologically acceptable salts thereof.

For the sake of clarity, the following sub-structure within formula (II)

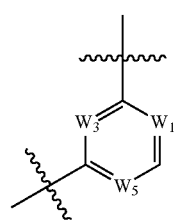

may comprise any combination of W1, W3 and W5 provided that the scaffold is pyridyl, pyrimidinyl or triazinyl, each of which can be optionally substituted as indicated above. Particularly, said sub-structure denotes the following scaffolds within the preferred embodiment according to sub-formula (II):

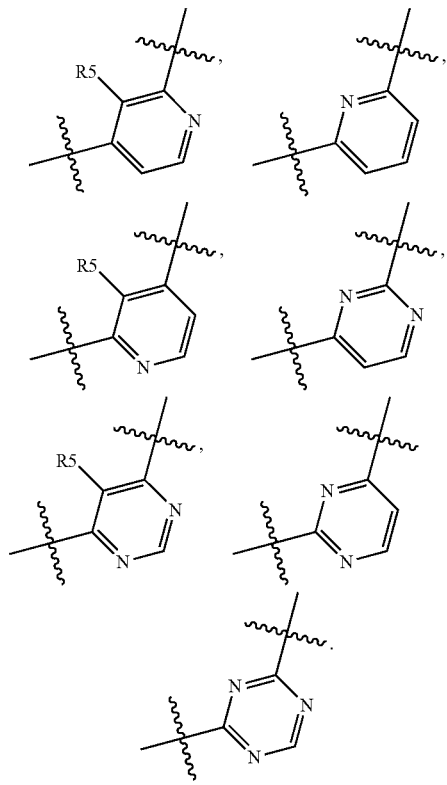

In a more preferred embodiment of the present invention, quinoline derivatives of sub-formula (III) are provided,

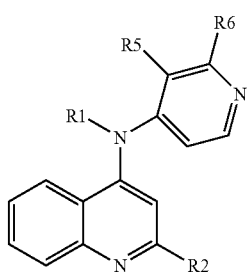

(III)

wherein

R1 denotes H;

R5 denotes H, A, OA, NH₂ or —NH—SO₂—NH₂;

R1, R5 together also denote —CO—NH—;

R6 denotes H, A or NH₂;

R5, R6 together also denote =CH—CH=C(Y)—CH= or —N=CH—CH=CH—;

R2 denotes phenyl, pyridin-2-yl, 2-fluoro-phenyl, 2-fluoro-5-fluoro-phenyl, 2-fluoro-5-chloro-phenyl, 2-fluoro-5-bromo-phenyl, 2-fluoro-5-trifluoromethyl-phenyl, 2-chloro-phenyl, 2-chloro-5-chloro-phenyl, 3-chloro-phenyl, 3-trifluoromethyl-phenyl, 6-methyl-pyridin-2-yl;

Y denotes H, A or OA;

and

A denotes methyl, ethyl or trifluoromethyl;

and/or physiologically acceptable salts thereof.

Most preferred embodiments are those compounds of formulae (I), (II) and (III) as listed in Table 1.

TABLE 1

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 003 | 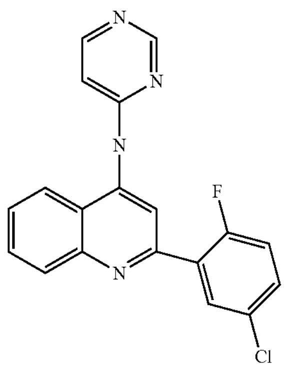 [SMILES: Fc1ccc(Cl)cc1-c1cc(Nc2ccncn2)c2ccccc2n1] | 350.8 | 351 | 1.68 method A | +++ |
| 004 | 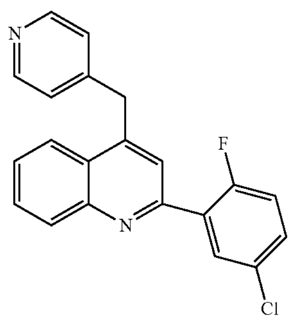 [SMILES: Fc1ccc(Cl)cc1-c1cc(Cc2ccncc2)c2ccccc2n1] | 348.8 | 349 | 1.91 method A | 0 |
| 005 | 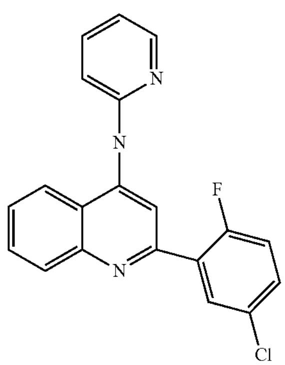 [SMILES: Fc1ccc(Cl)cc1-c1cc(Nc2ccccn2)c2ccccc2n1] | 349.8 | 350 | 2.03 method A | 0 |
| 006 | 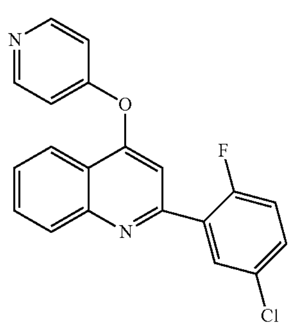 [SMILES: Fc1ccc(Cl)cc1-c1cc(Oc2ccncc2)c2ccccc2n1] | 350.8 | 351 | 2.28 method A | 0 |

TABLE 1-continued

Compounds of formulae (I), (II), (III)

| # | Structure | Mass calculated | M + H+ found | R_t [min] LC-MS method A/B | TβR activity 0 >10 uM + 1-10 uM ++ 0.5-1 uM +++ <0.5 uM |
|---|---|---|---|---|---|
| 007 | 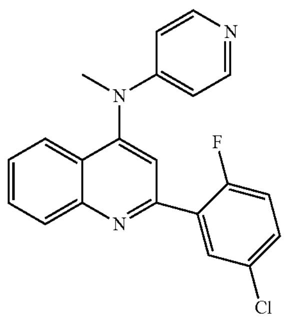 [SMILES: CN(c1ccncc1)c1cc(-c2cc(Cl)ccc2F)nc2ccccc12] | 363.8 | 364 | 2.17 method A | ++ |
| 008 | 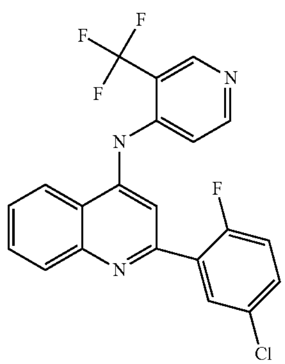 [SMILES: Fc1ccc(Cl)cc1-c1cc(Nc2ccncc2C(F)(F)F)c2ccccc2n1] | 417.8 | 418 | 2.18 | +++ |
| 009 | 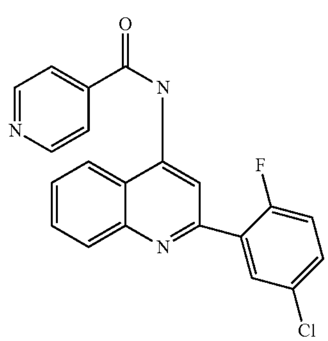 [SMILES: O=C(Nc1cc(-c2cc(Cl)ccc2F)nc2ccccc12)c1ccncc1] | 377.8 | 378 | 2.06 method A | + |
| 010 | 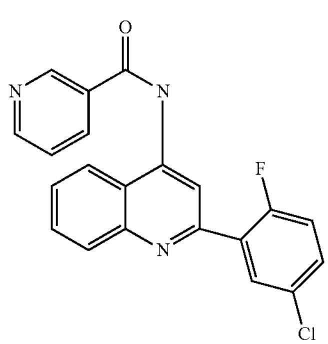 [SMILES: O=C(Nc1cc(-c2cc(Cl)ccc2F)nc2ccccc12)c1cccnc1] | 377.8 | 378 | 1.81 method A | + |

TABLE 1-continued
Compounds of formulae (I), (II), (III)
| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 011 | 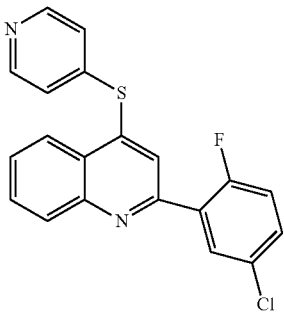 | 366.8 | 367 | 2.12 method A | + |
| 012 | 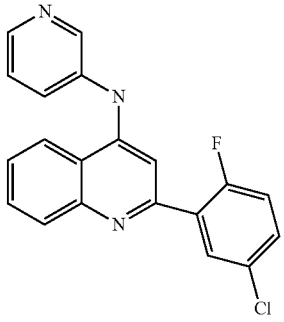 [SMILES: Fc1ccc(Cl)cc1-c1cc(Nc2cccnc2)c2ccccc2n1] | 349.8 | 350 | 1.47 method A | 0 |
| 013 | 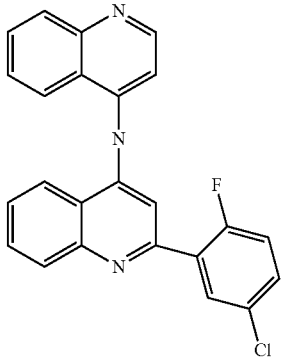 [SMILES: Fc1ccc(Cl)cc1-c1cc(Nc2ccnc3ccccc23)c2ccccc2n1] | 399.9 | 400 | 1.90 method A | +++ |
| 014 | 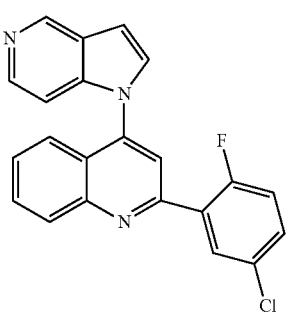 [SMILES: Fc1ccc(Cl)cc1-c1cc(-n2ccc3cnccc32)c2ccccc2n1] | 373.8 | 374 | 2.03 method A | +++ |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 015 | *structure* | 448.9 | 449 | 1.50 method A | 0 |
| 016 | *structure* | 338.8 | 339 | 1.57 method A | +++ |
| 017 | *structure* | 606.5 | 606 | 2.80 method A | + |

TABLE 1-continued

Compounds of formulae (I), (II), (III)

| # | Structure | Mass calculated | M + H+ found | R_t [min] LC-MS method A/B | TβR activity 0 >10 uM + 1-10 uM ++ 0.5-1 uM +++ <0.5 uM |
|---|---|---|---|---|---|
| 018 | 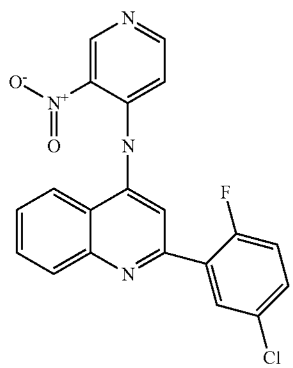 [SMILES: O=[N+]([O-])c1cnccc1Nc1cc(-c2cc(Cl)ccc2F)nc2ccccc12] | 394.8 | 395 | 2.07 method A | + |
| 019 | 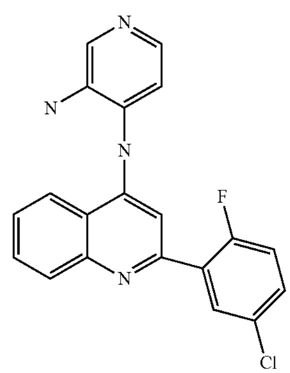 [SMILES: Nc1cnccc1Nc1cc(-c2cc(Cl)ccc2F)nc2ccccc12] | 364.8 | 365 | 1.52 | +++ |
| 020 | 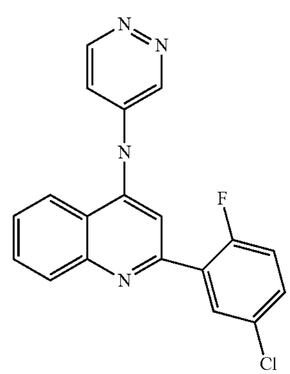 [SMILES: Fc1ccc(Cl)cc1-c1cc(Nc2ccnnc2)c2ccccc2n1] | 350.8 | 351 | 1.74 method A | +++ |
| 021 | 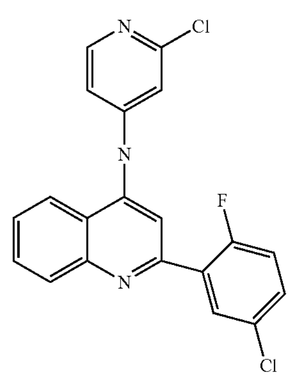 | 384.2 | 384 | 1.81 method A | + |

TABLE 1-continued

Compounds of formulae (I), (II), (III)

| # | Structure | Mass calculated | M + H+ found | R_t [min] LC-MS method A/B | TβR activity 0 >10 uM + 1-10 uM ++ 0.5-1 uM +++ <0.5 uM |
|---|---|---|---|---|---|
| 022 | 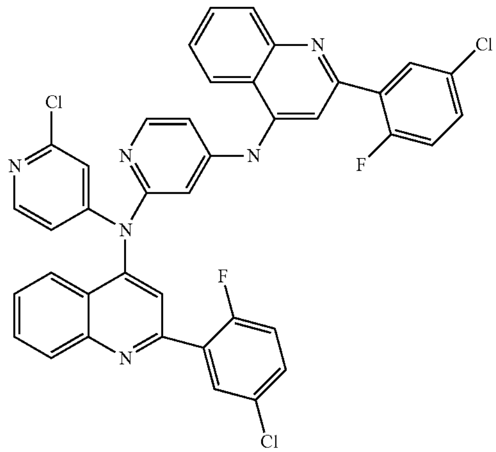 [SMILES: Fc1ccc(Cl)cc1-c1cc(Nc2ccnc(N(c3ccnc(Cl)c3)c3cc(-c4cc(Cl)ccc4F)nc4ccccc34)c2)c2ccccc2n1] | 732.0 | 731 | 2.35 method A | + |
| 023 | 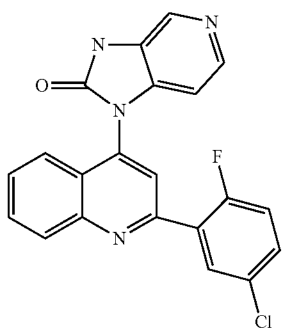 [SMILES: O=c1[nH]c2cnccc2n1-c1cc(-c2cc(Cl)ccc2F)nc2ccccc12] | 390.8 | 391 | 1.78 | +++ |
| 024 | 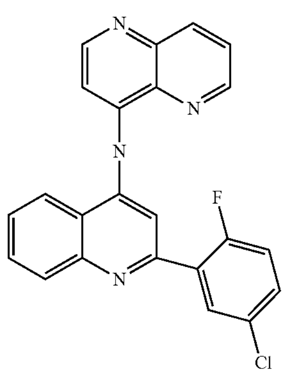 [SMILES: Fc1ccc(Cl)cc1-c1cc(Nc2ccnc3cccnc23)c2ccccc2n1] | 400.8 | 401 | 2.00 | +++ |
| 025 | 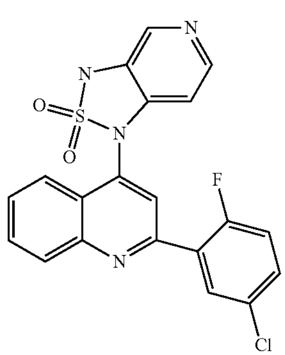 [SMILES: O=S1(=O)Nc2cnccc2N1c1cc(-c2cc(Cl)ccc2F)nc2ccccc12] | 426.9 | 427 | 2.11 | +++ |

TABLE 1-continued

Compounds of formulae (I), (II), (III)

| # | Structure | Mass calculated | M + H+ found | R_t [min] LC-MS method A/B | TβR activity 0 >10 uM + 1-10 uM ++ 0.5-1 uM +++ <0.5 uM |
|---|---|---|---|---|---|
| 026 | 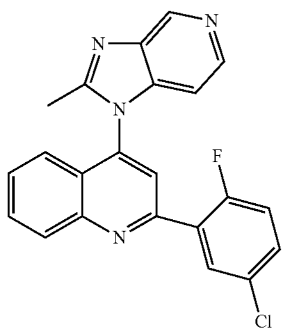 [SMILES: Cc1nc2cnccc2n1-c1cc(-c2cc(Cl)ccc2F)nc2ccccc12] | 388.8 | 389 | 1.83 | ++ |
| 027 | 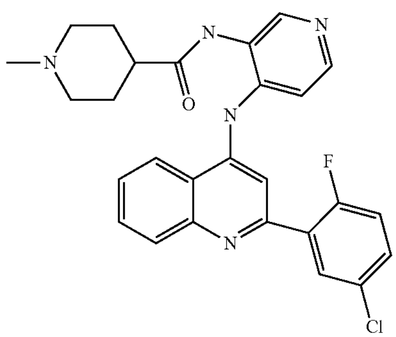 [SMILES: CN1CCC(C(=O)Nc2cnccc2Nc2cc(-c3cc(Cl)ccc3F)nc3ccccc23)CC1] | 490.0 | 490 | 1.50 | +++ |
| 028 | 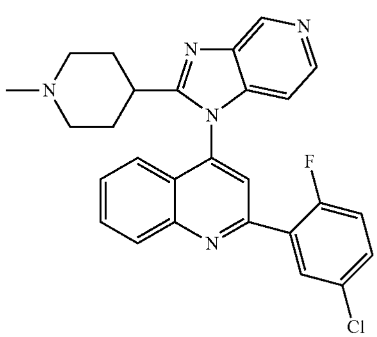 [SMILES: CN1CCC(c2nc3cnccc3n2-c2cc(-c3cc(Cl)ccc3F)nc3ccccc23)CC1] | 472.0 | 472 | 1.43 | 0 |
| 029 | 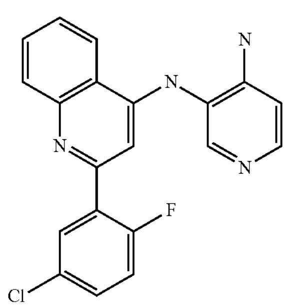 [SMILES: Nc1ccncc1Nc1cc(-c2cc(Cl)ccc2F)nc2ccccc12] | 364.8 | 365 | 1.11 method B | 0 |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 030 | 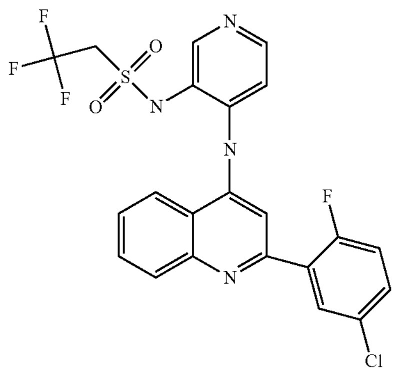 [SMILES: O=S(=O)(CC(F)(F)F)Nc1cnccc1Nc1cc(-c2cc(Cl)ccc2F)nc2ccccc12] | 510.9 | 511 | 2.21 | + |
| 031 | 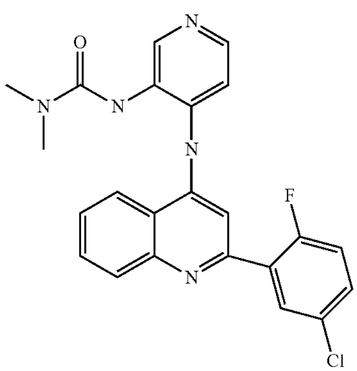 [SMILES: CN(C)C(=O)Nc1cnccc1Nc1cc(-c2cc(Cl)ccc2F)nc2ccccc12] | 435.9 | 436 | 1.80 | +++ |
| 032 | 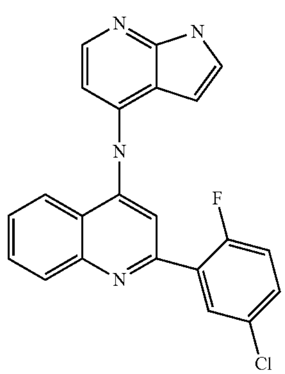 [SMILES: Fc1ccc(Cl)cc1-c1cc(Nc2ccnc3[nH]ccc23)c2ccccc2n1] | 388.8 | 389 | 1.66 | 0 |
| 033 | 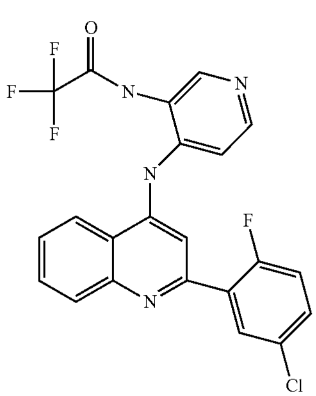 [SMILES: O=C(Nc1cnccc1Nc1cc(-c2cc(Cl)ccc2F)nc2ccccc12)C(F)(F)F] | 460.8 | 461 | 1.90 | + |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 034 | 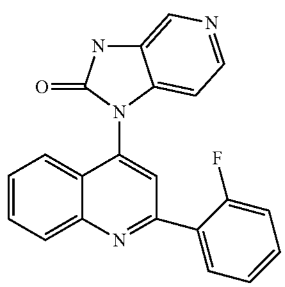 [SMILES: O=c1[nH]c2cnccc2n1-c1cc(-c2ccccc2F)nc2ccccc12] | 356.4 | 357 | 1.58 | ++ |
| 035 | 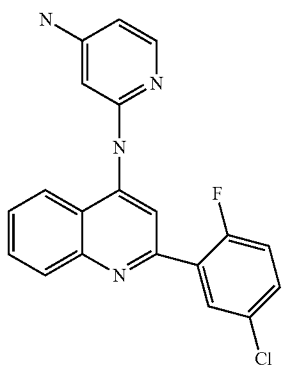 [SMILES: Nc1ccnc(Nc2cc(-c3cc(Cl)ccc3F)nc3ccccc23)c1] | 364.8 | 365 | 1.58 method B | 0 |
| 036 | 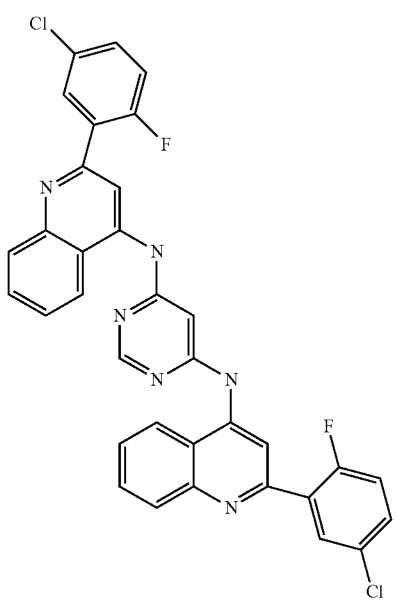 [SMILES: Fc1ccc(Cl)cc1-c1cc(Nc2cc(Nc3cc(-c4cc(Cl)ccc4F)nc4ccccc34)ncn2)c2ccccc2n1] | 621.5 | 621 | 2.69 | 0 |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 037 | 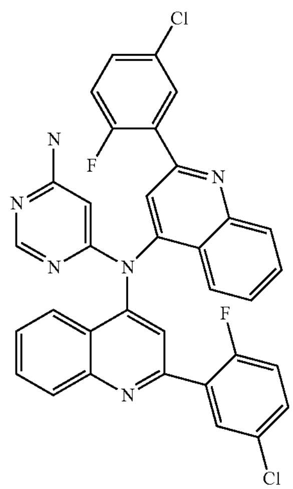 [SMILES: Nc1cc(N(c2cc(-c3cc(Cl)ccc3F)nc3ccccc23)c2cc(-c3cc(Cl)ccc3F)nc3ccccc23)ncn1] | 621.5 | 621 | 3.01 | + |
| 038 | 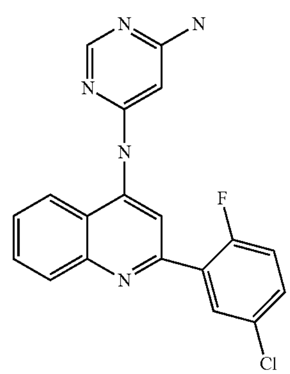 [SMILES: Nc1cc(Nc2cc(-c3cc(Cl)ccc3F)nc3ccccc23)ncn1] | 365.8 | 366 | 1.63 | +++ |
| 039 | 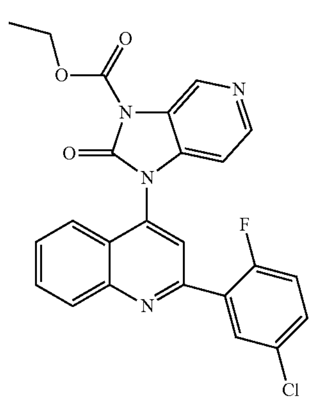 [SMILES: CCOC(=O)n1c(=O)n(-c2cc(-c3cc(Cl)ccc3F)nc3ccccc23)c2ccncc21] | 462.9 | 463 | 2.30 | +++ |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 040 | 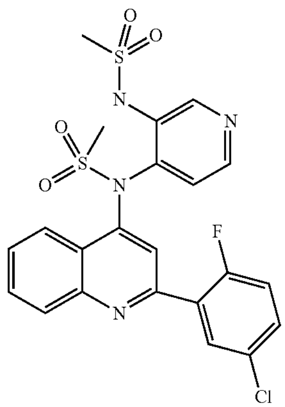 [SMILES: CS(=O)(=O)Nc1cnccc1N(c1cc(-c2cc(Cl)ccc2F)nc2ccccc12)S(C)(=O)=O] | 521.0 | 521 | 1.96 | + |
| 041 | 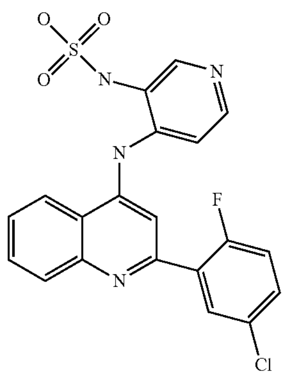 [SMILES: O=S(=O)(O)Nc1cnccc1Nc1cc(-c2cc(Cl)ccc2F)nc2ccccc12] | 444.9 (466.9) | 445 | 1.75 | + |
| 042 | 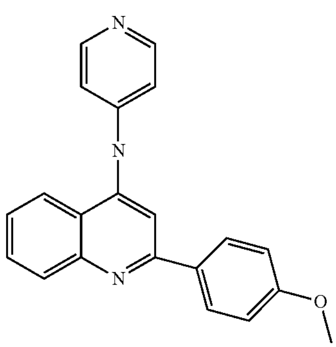 [SMILES: COc1ccc(-c2cc(Nc3ccncc3)c3ccccc3n2)cc1] | 327.4 | 328 | 1.27 | ++ |
| 043 | 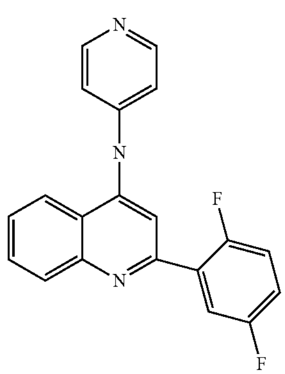 | 333.3 | 334 | 1.59 | +++ |

TABLE 1-continued
Compounds of formulae (I), (II), (III)
| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 044 | 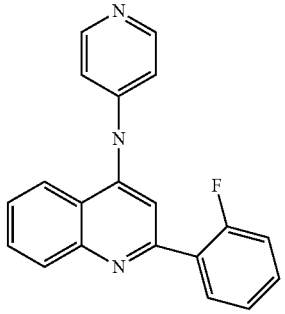 | 315.3 | 316 | 1.48 | +++ |
| 045 | 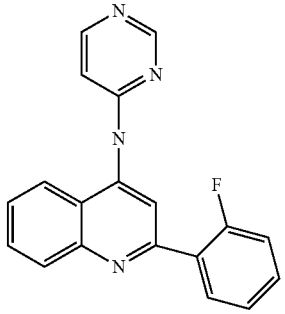 [SMILES: Fc1ccccc1-c1cc(Nc2ccncn2)c2ccccc2n1] | 316.3 | 317 | 1.50 | +++ |
| 046 | 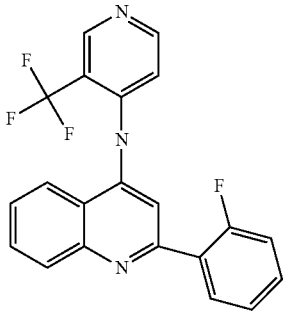 [SMILES: Fc1ccccc1-c1cc(Nc2ccncc2C(F)(F)F)c2ccccc2n1] | 383.3 | 384 | 1.76 | +++ |
| 047 | 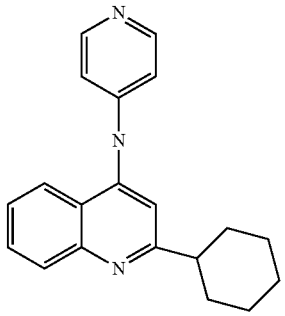 [SMILES: c1ccc2c(Nc3ccncc3)cc(C3CCCCC3)nc2c1] | 303.4 | 304 | 1.15 method B | + |

TABLE 1-continued
Compounds of formulae (I), (II), (III)
| # | Structure | Mass calculated | M + H+ found | $R_t$ [min] LC-MS method A/B | TβR activity<br>0 >10 uM<br>+ 1-10 uM<br>++ 0.5-1 uM<br>+++ <0.5 uM |
|---|---|---|---|---|---|
| 048 | 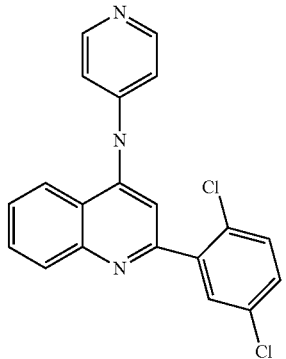 | 366.2 | 366 | 1.69 | +++ |
| 049 | 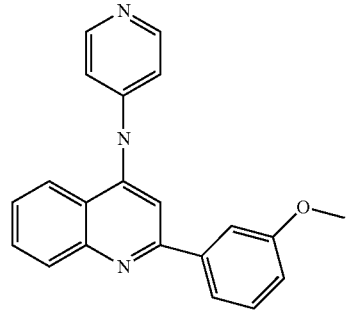 [SMILES: COc1cccc(-c2cc(Nc3ccncc3)c3ccccc3n2)c1] | 327.4 | 328 | 1.41 | ++ |
| 050 | 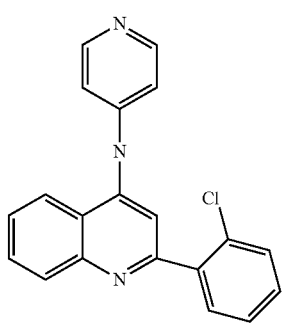 | 331.8 | 332 | 1.45 | +++ |
| 051 | 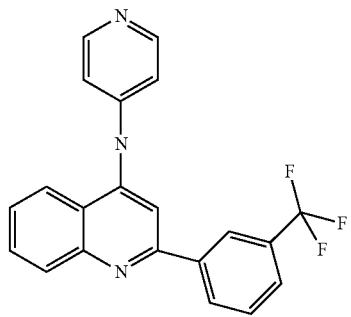 [SMILES: FC(F)(F)c1cccc(-c2cc(Nc3ccncc3)c3ccccc3n2)c1] | 365.4 | 366 | 1.83 | +++ |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 052 | 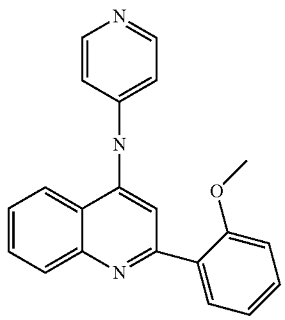 [SMILES: COc1ccccc1-c1cc(Nc2ccncc2)c2ccccc2n1] | 327.4 | 328 | 1.22 | + |
| 053 | 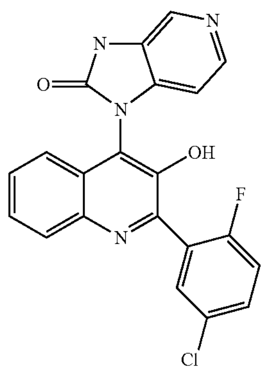 [SMILES: O=c1[nH]c2cnccc2n1-c1c(O)c(-c2cc(Cl)ccc2F)nc2ccccc12] | 406.8 | 407 | 2.04 | + |
| 054 | 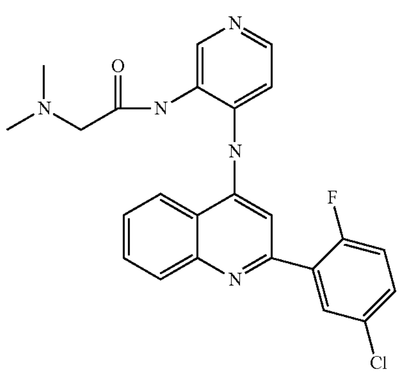 [SMILES: CN(C)CC(=O)Nc1cnccc1Nc1cc(-c2cc(Cl)ccc2F)nc2ccccc12] | 449.9 | 450 | 1.43 | +++ |
| 055 | 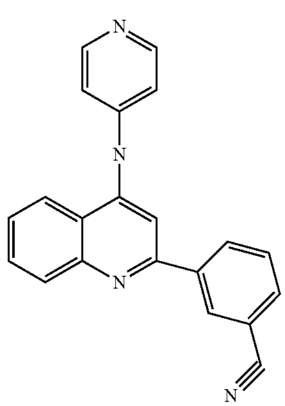 [SMILES: N#Cc1cccc(-c2cc(Nc3ccncc3)c3ccccc3n2)c1] | 322.4 | 323 | 1.53 | + |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 056 | 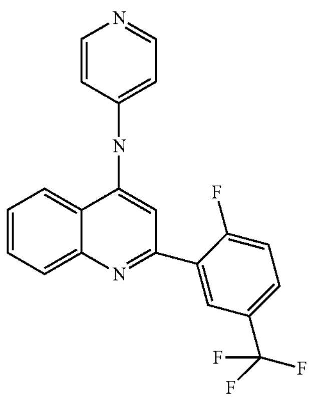 [SMILES: Fc1ccc(C(F)(F)F)cc1-c1cc(Nc2ccncc2)c2ccccc2n1] | 383.3 | 384 | 1.76 | +++ |
| 057 | 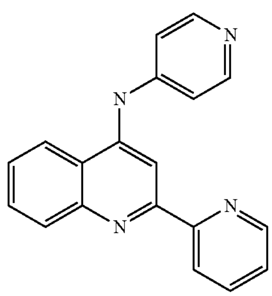 [SMILES: c1ccc(-c2cc(Nc3ccncc3)c3ccccc3n2)nc1] | 298.3 | 299 | 1.29 | +++ |
| 058 | 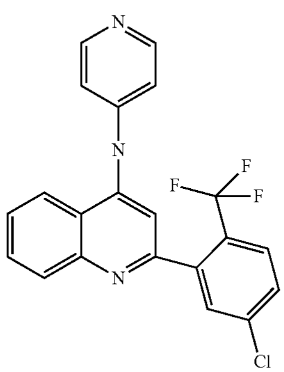 [SMILES: FC(F)(F)c1ccc(Cl)cc1-c1cc(Nc2ccncc2)c2ccccc2n1] | 399.8 | 400 | 1.80 | 0 |
| 059 | 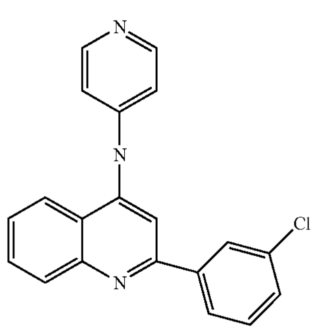 [SMILES: Clc1cccc(-c2cc(Nc3ccncc3)c3ccccc3n2)c1] | 331.8 | 332 | 1.71 | +++ |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 060 | 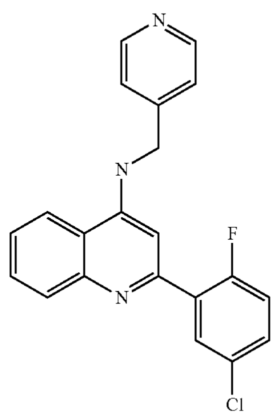 [SMILES: Fc1ccc(Cl)cc1-c1cc(NCc2ccncc2)c2ccccc2n1] | 363.8 | 364 | 1.18 method B | 0 |
| 061 | 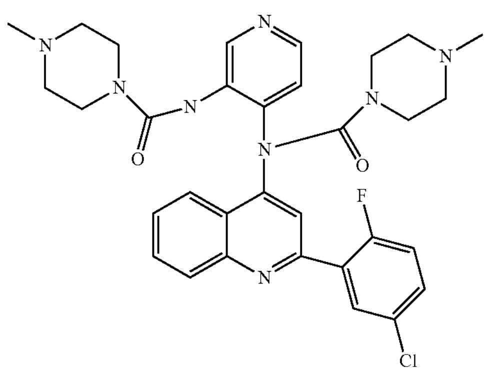 | 617.1 | 617 | 1.24 | 0 |
| 062 | 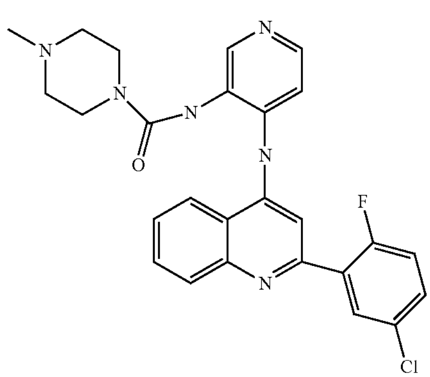 [SMILES: CN1CCN(C(=O)Nc2cnccc2Nc2cc(-c3cc(Cl)ccc3F)nc3ccccc23)CC1] | 491.0 | 491 | 1.39 | ++ |

TABLE 1-continued
Compounds of formulae (I), (II), (III)
| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 063 | 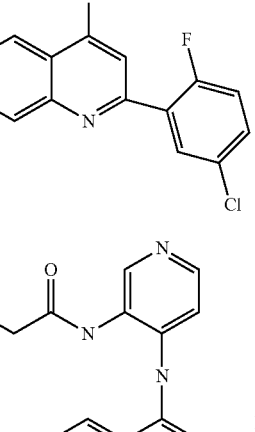 | 350.8 | 351 | 2.83 method B | 0 |
| 064 | 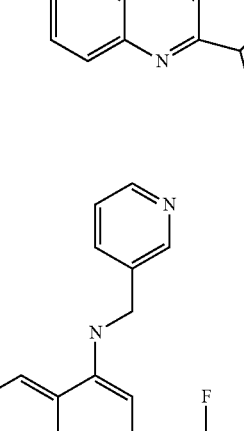 | 463.9 | 464 | 1.41 | +++ |
| 065 | 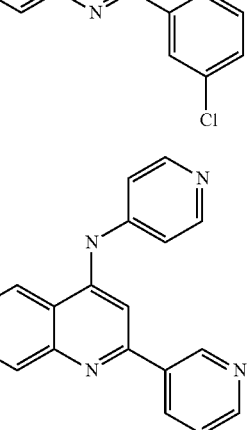 | 363.8 | 364 | 1.29 method B | 0 |
| 066 | 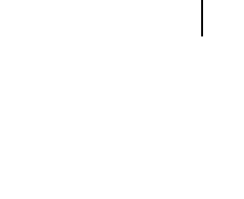 | 312.4 | 313 | 1.20 method B | 0 |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 067 | 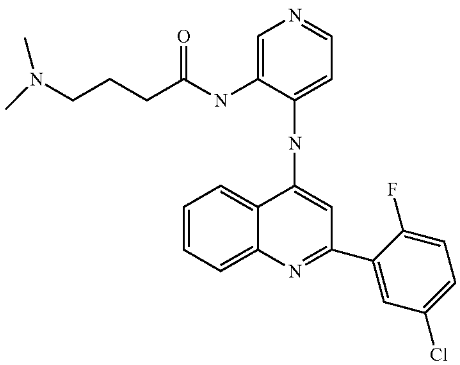 [SMILES: CN(C)CCCC(=O)Nc1cnccc1Nc1cc(-c2cc(Cl)ccc2F)nc2ccccc12] | 478.0 | 478 | 1.47 | ++ |
| 068 | 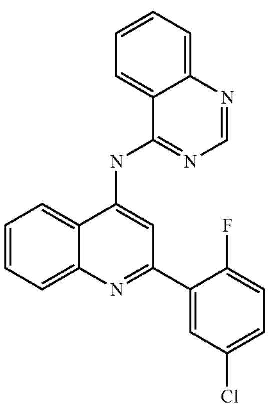 [SMILES: Fc1ccc(Cl)cc1-c1cc(Nc2ncnc3ccccc23)c2ccccc2n1] | 400.8 | 401 | 1.94 | +++ |
| 069 | 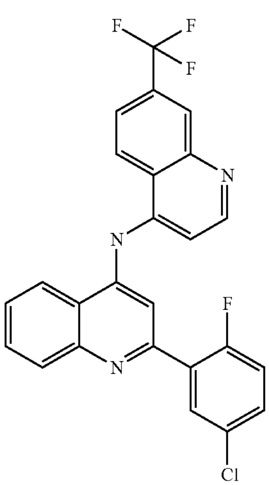 [SMILES: Fc1ccc(Cl)cc1-c1cc(Nc2ccnc3cc(C(F)(F)F)ccc23)c2ccccc2n1] | 467.9 | 468 | 2.00 | +++ |

TABLE 1-continued
Compounds of formulae (I), (II), (III)
| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 070 | 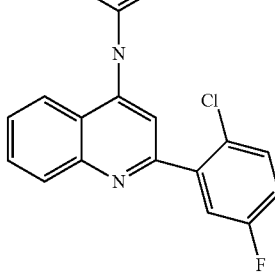 | 349.8 | 350 | 1.60 | + |
| 071 | 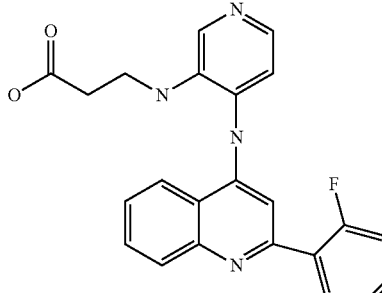 | 436.9 | 437 | 1.19 | 0 |
| 072 | 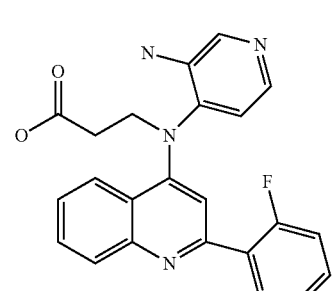 | 436.9 | 437 | 1.60 | 0 |
| 073 | 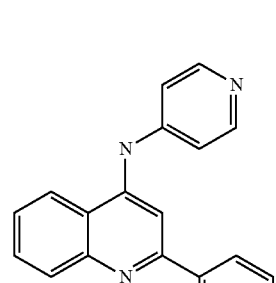 | 297.4 | 298 | 1.38 | +++ |

TABLE 1-continued
Compounds of formulae (I), (II), (III)
| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 074 | 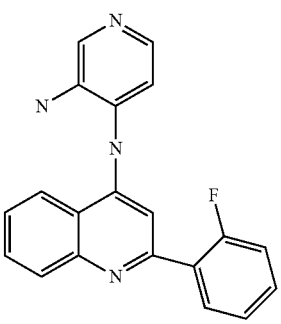 [SMILES: Nc1cnccc1Nc1cc(-c2ccccc2F)nc2ccccc12] | 330.4 | 331 | 1.23 | + |
| 075 | 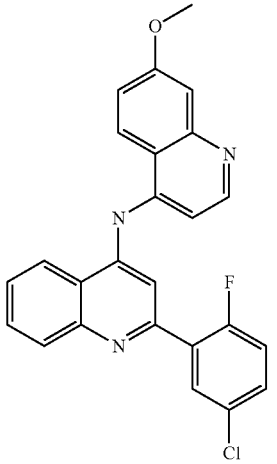 [SMILES: COc1ccc2c(Nc3cc(-c4cc(Cl)ccc4F)nc4ccccc34)ccnc2c1] | 429.9 | 430 | 1.81 | +++ |
| 076 | 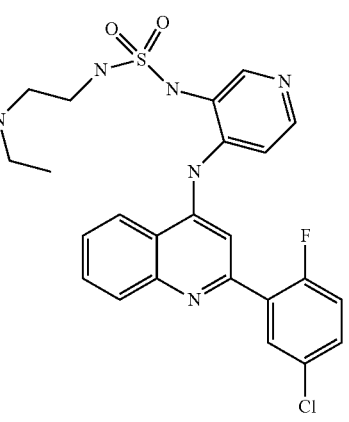 | 543.1 | 543 | 1.54 | + |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 077 | 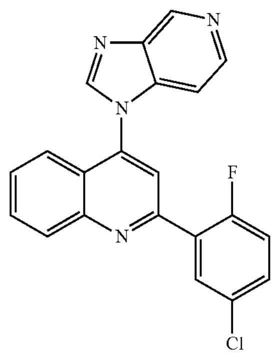 [SMILES: Fc1ccc(Cl)cc1-c1cc(-n2cnc3cnccc32)c2ccccc2n1] | 374.8 | 375 | 1.95 | +++ |
| 078 | 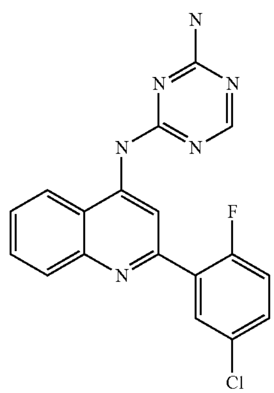 [SMILES: Nc1ncnc(Nc2cc(-c3cc(Cl)ccc3F)nc3ccccc23)n1] | 366.8 | 367 | 1.82 | +++ |
| 079 | 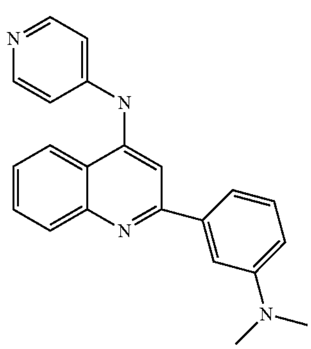 [SMILES: CN(C)c1cccc(-c2cc(Nc3ccncc3)c3ccccc3n2)c1] | 340.4 | 341 | 1.37 | + |
| 080 | 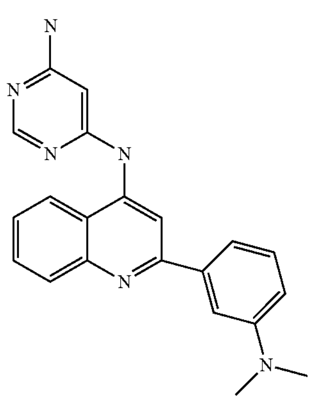 [SMILES: CN(C)c1cccc(-c2cc(Nc3cc(N)ncn3)c3ccccc3n2)c1] | 356.4 | 357 | 1.58 | 0 |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 081 | 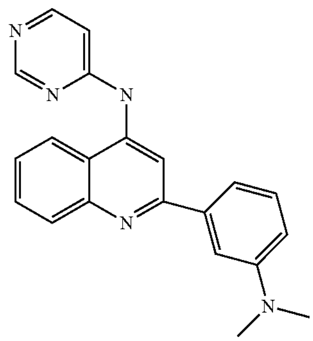 [SMILES: CN(C)c1cccc(-c2cc(Nc3ccncn3)c3ccccc3n2)c1] | 341.4 | 342 | 1.57 | 0 |
| 082 | 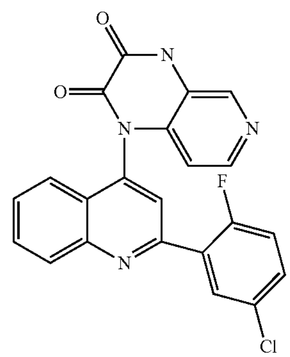 [SMILES: O=c1[nH]c2cnccc2n(-c2cc(-c3cc(Cl)ccc3F)nc3ccccc23)c1=O] | 418.8 | 419 | 2.12 | + |
| 083 | 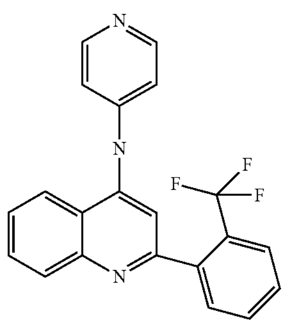 [SMILES: FC(F)(F)c1ccccc1-c1cc(Nc2ccncc2)c2ccccc2n1] | 365.4 | 366 | 1.57 | 0 |
| 084 | 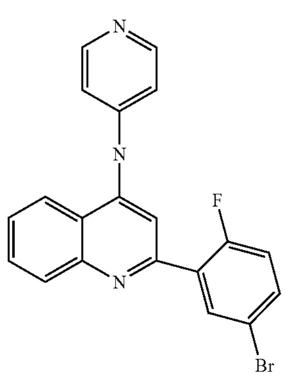 [SMILES: Fc1ccc(Br)cc1-c1cc(Nc2ccncc2)c2ccccc2n1] | 394.2 | 394 | 1.77 | +++ |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 085 | 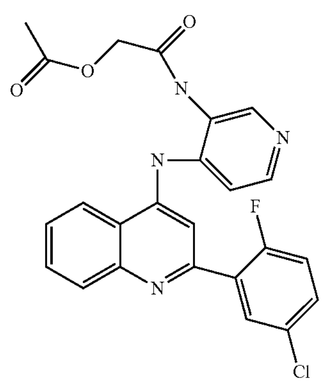 [SMILES: CC(=O)OCC(=O)Nc1cnccc1Nc1cc(-c2cc(Cl)ccc2F)nc2ccccc12] | 464.9 | 465 | 1.72 | +++ |
| 086 | 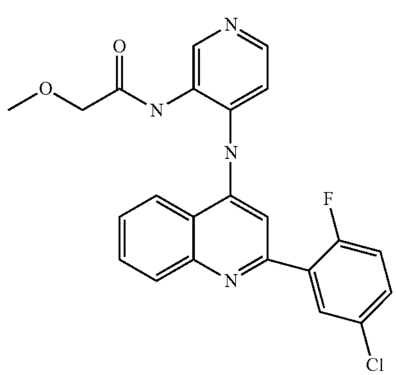 [SMILES: COCC(=O)Nc1cnccc1Nc1cc(-c2cc(Cl)ccc2F)nc2ccccc12] | 436.9 | 437 | 1.71 | +++ |
| 087 | 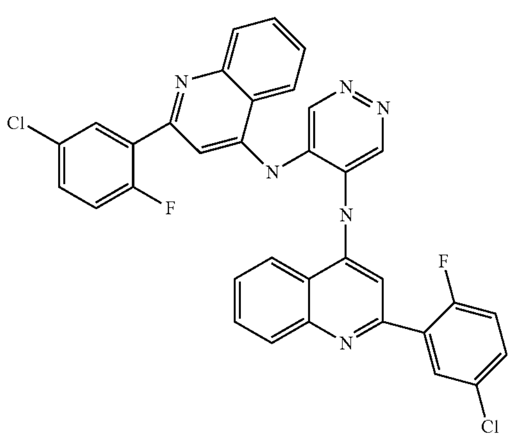 [SMILES: Fc1ccc(Cl)cc1-c1cc(Nc2cnncc2Nc2cc(-c3cc(Cl)ccc3F)nc3ccccc23)c2ccccc2n1] | 621.5 | 621 | 1.89 | 0 |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 088 | 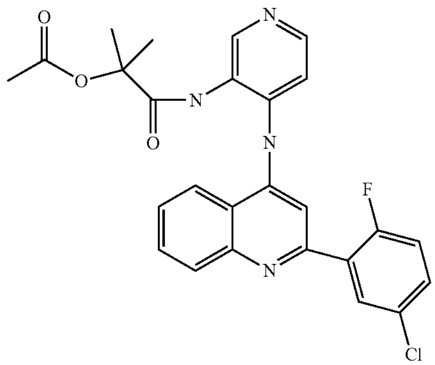 [SMILES: CC(=O)OC(C)(C)C(=O)Nc1cnccc1Nc1cc(-c2cc(Cl)ccc2F)nc2ccccc12] | 492.9 | 493 | 1.88 | + |
| 089 | 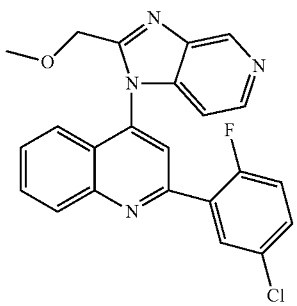 [SMILES: COCc1nc2cnccc2n1-c1cc(-c2cc(Cl)ccc2F)nc2ccccc12] | 418.9 | 419 | 1.93 | +++ |
| 090 | 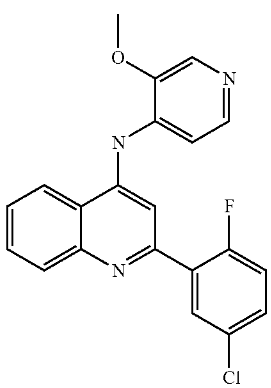 [SMILES: COc1cnccc1Nc1cc(-c2cc(Cl)ccc2F)nc2ccccc12] | 379.8 | 380 | 1.74 | +++ |
| 091 | 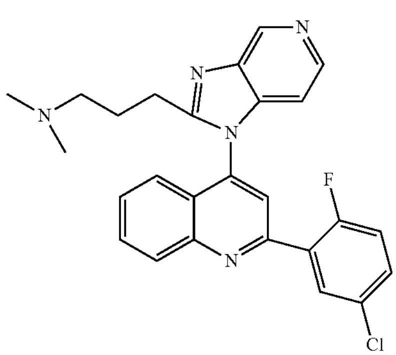 [SMILES: CN(C)CCCc1nc2cnccc2n1-c1cc(-c2cc(Cl)ccc2F)nc2ccccc12] | 460.0 | 460 | 1.48 | + |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 092 | 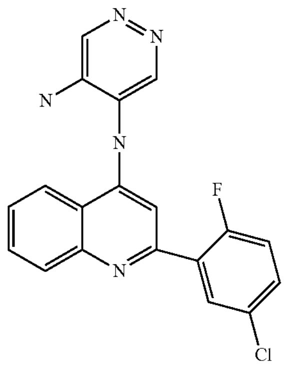 [SMILES: Nc1cnncc1Nc1cc(-c2cc(Cl)ccc2F)nc2ccccc12] | 365.8 | 367 | 1.34 | + |
| 093 | 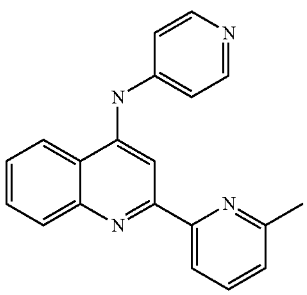 [SMILES: Cc1cccc(-c2cc(Nc3ccncc3)c3ccccc3n2)n1] | 312.4 | 313 | 1.27 | +++ |
| 094 | 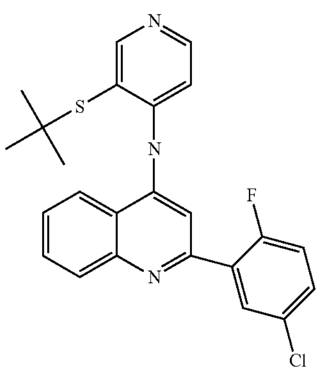 [SMILES: CC(C)(C)Sc1cnccc1Nc1cc(-c2cc(Cl)ccc2F)nc2ccccc12] | 438.0 | 438 | 2.18 | ++ |
| 095 | 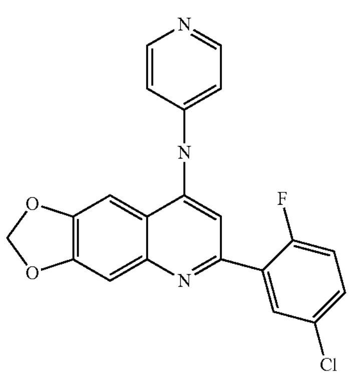 [SMILES: Fc1ccc(Cl)cc1-c1cc(Nc2ccncc2)c2cc3c(cc2n1)OCO3] | 393.8 | 394 | 1.85 | 0 |

TABLE 1-continued

Compounds of formulae (I), (II), (III)

| # | Structure | Mass calculated | M + H+ found | R_t [min] LC-MS method A/B | TβR activity<br>0 >10 uM<br>+ 1-10 uM<br>++ 0.5-1 uM<br>+++ <0.5 uM |
|---|---|---|---|---|---|
| 096 | 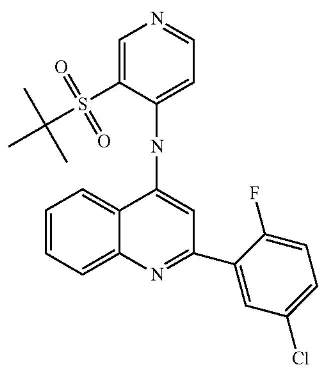 [SMILES: CC(C)(C)S(=O)(=O)c1cnccc1Nc1cc(-c2cc(Cl)ccc2F)nc2ccccc12] | 470.0 | 470 | 2.72 | 0 |
| 097 | 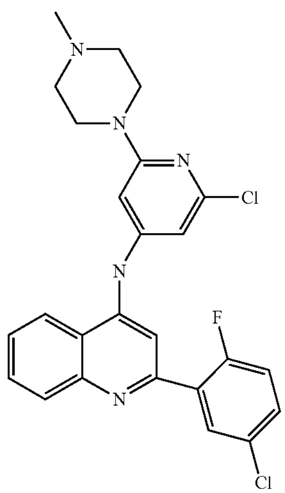 [SMILES: CN1CCN(c2cc(Nc3cc(-c4cc(Cl)ccc4F)nc4ccccc34)cc(Cl)n2)CC1] | 482.4 | 482 | 1.68 | 0 |
| 098 | 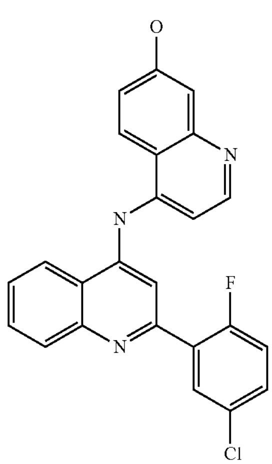 [SMILES: Oc1ccc2c(Nc3cc(-c4cc(Cl)ccc4F)nc4ccccc34)ccnc2c1] | 415.9 | 416 | 1.77 | ++ |

TABLE 1-continued
Compounds of formulae (I), (II), (III)
| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 099 | 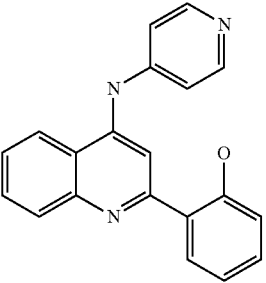 [SMILES: Oc1ccccc1-c1cc(Nc2ccncc2)c2ccccc2n1] | 313.4 | 314 | 1.56 | 0 |
| 100 | 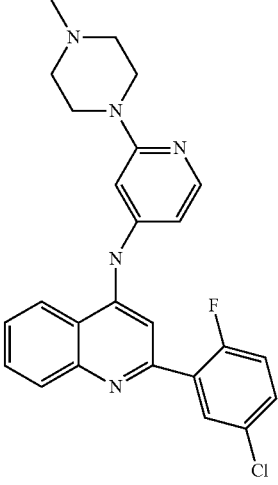 [SMILES: CN1CCN(c2cc(Nc3cc(-c4cc(Cl)ccc4F)nc4ccccc34)ccn2)CC1] | 447.9 | 448 | 1.34 | + |
| 101 | 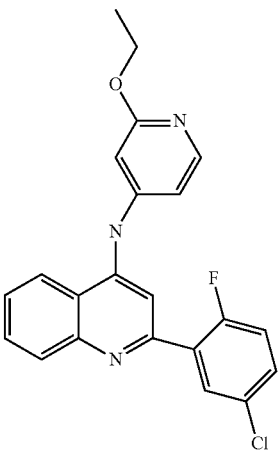 [SMILES: CCOc1cc(Nc2cc(-c3cc(Cl)ccc3F)nc3ccccc23)ccn1] | 393.8 | 394 | 1.93 | 0 |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 102 | 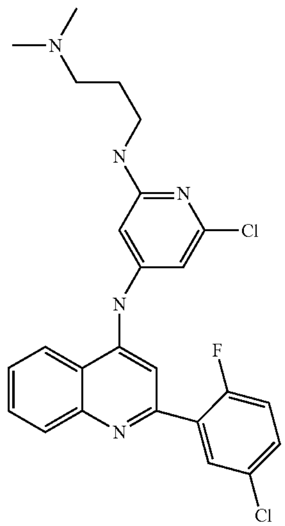 [SMILES: CN(C)CCCNc1cc(Nc2cc(-c3cc(Cl)ccc3F)nc3ccccc23)cc(Cl)n1] | 484.4 | 484 | 1.51 | + |
| 103 | 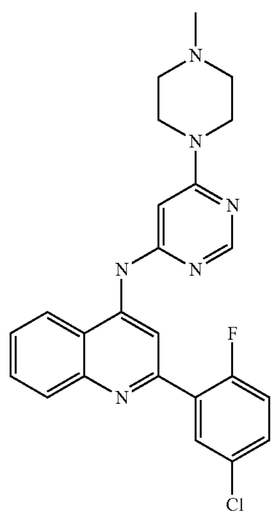 [SMILES: CN1CCN(c2cc(Nc3cc(-c4cc(Cl)ccc4F)nc4ccccc34)ncn2)CC1] | 448.9 | 449 | 1.37 | 0 |
| 104 | 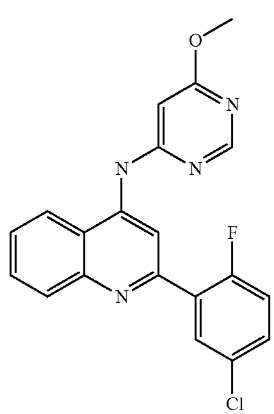 [SMILES: COc1cc(Nc2cc(-c3cc(Cl)ccc3F)nc3ccccc23)ncn1] | 380.8 | 381 | 2.01 | 0 |

TABLE 1-continued

Compounds of formulae (I), (II), (III)

| # | Structure | Mass calculated | M + H+ found | R_t [min] LC-MS method A/B | TβR activity<br>0 >10 uM<br>+ 1-10 uM<br>++ 0.5-1 uM<br>+++ <0.5 uM |
|---|---|---|---|---|---|
| 105 | 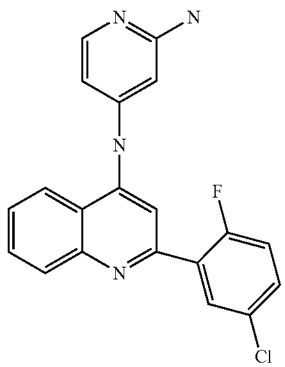 [SMILES: Nc1cc(Nc2cc(-c3cc(Cl)ccc3F)nc3ccccc23)ccn1] | 364.8 | 365 | 1.65 | +++ |
| 106 | 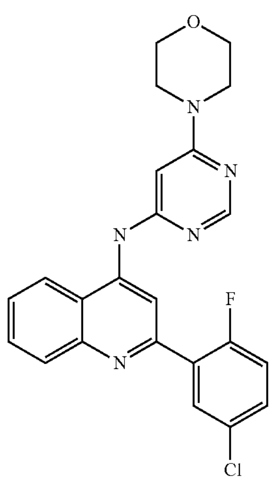 [SMILES: Fc1ccc(Cl)cc1-c1cc(Nc2cc(N3CCOCC3)ncn2)c2ccccc2n1] | 435.9 | 436 | 1.82 | 0 |
| 107 | 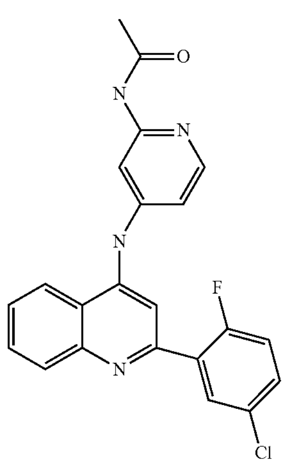 [SMILES: CC(=O)Nc1cc(Nc2cc(-c3cc(Cl)ccc3F)nc3ccccc23)ccn1] | 406.8 | 407 | 1.65 | +++ |

TABLE 1-continued

Compounds of formulae (I), (II), (III)

| # | Structure | Mass calculated | M + H+ found | R_t [min] LC-MS method A/B | TβR activity 0 >10 uM + 1-10 uM ++ 0.5-1 uM +++ <0.5 uM |
|---|---|---|---|---|---|
| 108 | 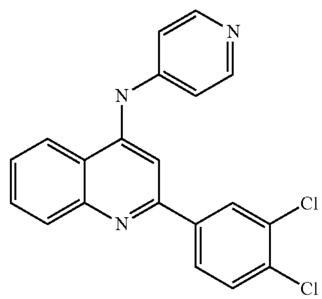 [SMILES: Clc1ccc(-c2cc(Nc3ccncc3)c3ccccc3n2)cc1Cl] | 366.2 | 366 | 1.77 | 0 |
| 109 | 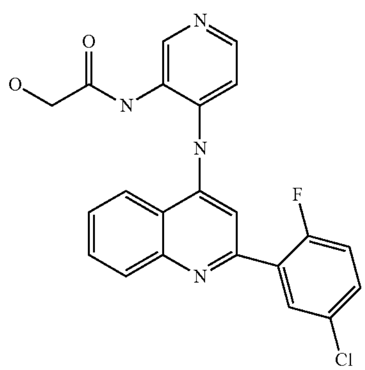 [SMILES: O=C(CO)Nc1cnccc1Nc1cc(-c2cc(Cl)ccc2F)nc2ccccc12] | 422.8 | 423 | 1.60 | ++ |
| 110 | 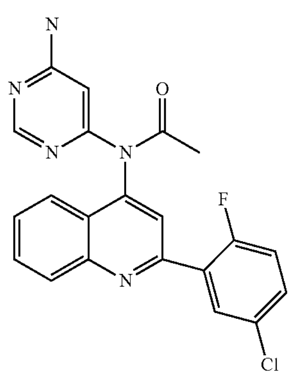 [SMILES: CC(=O)N(c1cc(N)ncn1)c1cc(-c2cc(Cl)ccc2F)nc2ccccc12] | 407.8 | 408 | 2.16 | + |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 111 | 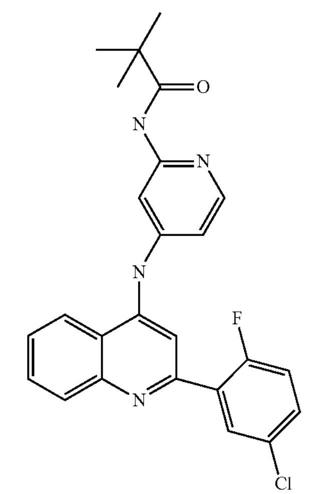 [SMILES: CC(C)(C)C(=O)Nc1cc(Nc2cc(-c3cc(Cl)ccc3F)nc3ccccc23)ccn1] | 448.9 | 449 | 1.95 | + |
| 112 | 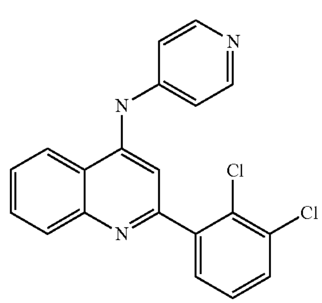 [SMILES: Clc1cccc(-c2cc(Nc3ccncc3)c3ccccc3n2)c1Cl] | 366.2 | 366 | 1.69 | 0 |
| 113 | 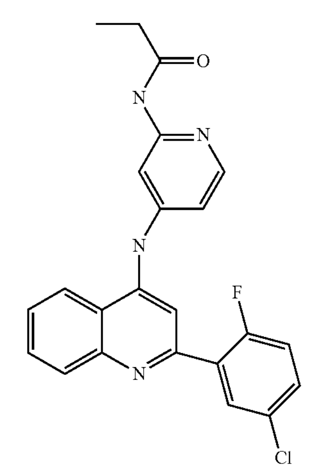 [SMILES: CCC(=O)Nc1cc(Nc2cc(-c3cc(Cl)ccc3F)nc3ccccc23)ccn1] | 420.9 | 421 | 1.76 | +++ |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 114 | 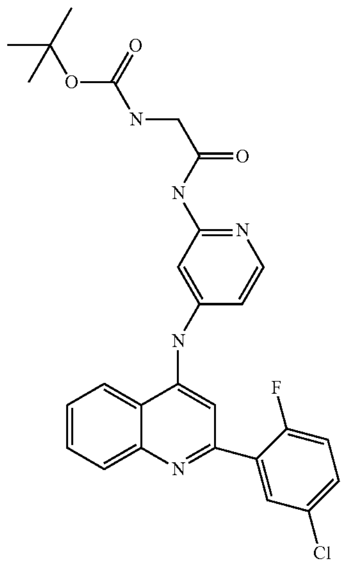 [SMILES: CC(C)(C)OC(=O)NCC(=O)Nc1cc(Nc2cc(-c3cc(Cl)ccc3F)nc3ccccc23)ccn1] | 522.0 | 522 | 1.87 | + |
| 115 | 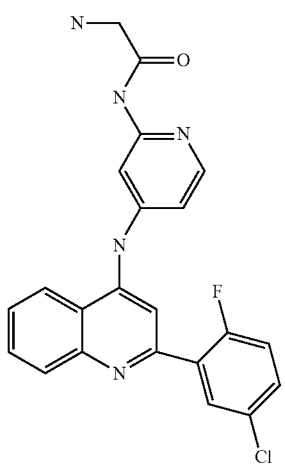 [SMILES: NCC(=O)Nc1cc(Nc2cc(-c3cc(Cl)ccc3F)nc3ccccc23)ccn1] | 421.9 | 422 | 1.12 method B | + |
| 116 | 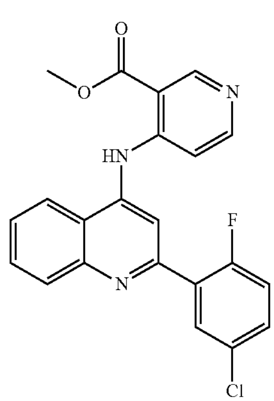 [SMILES: COC(=O)c1cnccc1Nc1cc(-c2cc(Cl)ccc2F)nc2ccccc12] | 407.8 | 408 | 1.99 method B | +++ |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 117 | 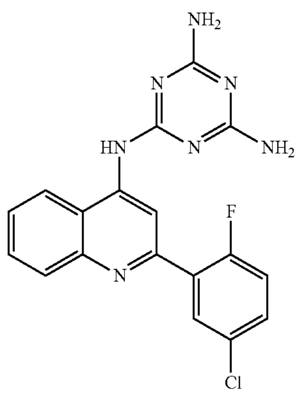 [SMILES: Nc1nc(N)nc(Nc2cc(-c3cc(Cl)ccc3F)nc3ccccc23)n1] | 381.8 | 382 | 1.58 method B | + |
| 118 | 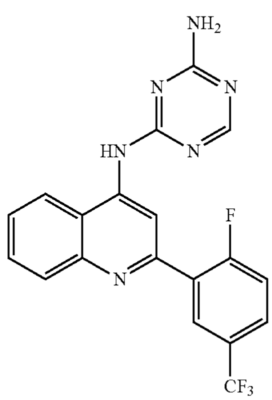 [SMILES: Nc1ncnc(Nc2cc(-c3cc(C(F)(F)F)ccc3F)nc3ccccc23)n1] | 399.4 | 400 | 1.68 method B | +++ |
| 119 | 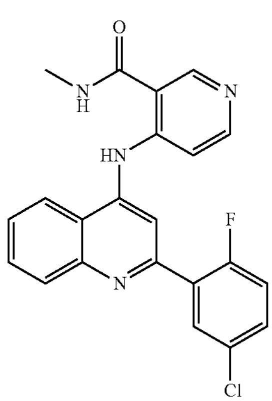 [SMILES: CNC(=O)c1cnccc1Nc1cc(-c2cc(Cl)ccc2F)nc2ccccc12] | 406.9 | 407 | 1.82 method B | +++ |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 120 | 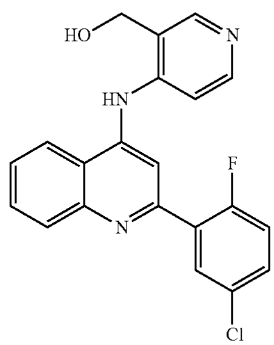 [SMILES: OCc1cnccc1Nc1cc(-c2cc(Cl)ccc2F)nc2ccccc12] | 379.8 | 380 | 1.71 method B | +++ |
| 121 | 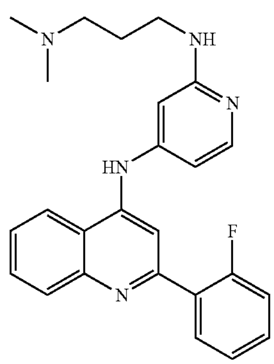 [SMILES: CN(C)CCCNc1cc(Nc2cc(-c3ccccc3F)nc3ccccc23)ccn1] | 415.5 | 416 | 1.11 method B | +++ |
| 122 | 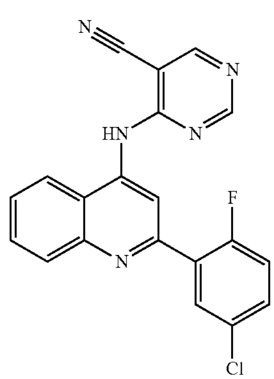 [SMILES: N#Cc1cncnc1Nc1cc(-c2cc(Cl)ccc2F)nc2ccccc12] | 375.8 | 376 | 2.38 method B | +++ |

TABLE 1-continued

Compounds of formulae (I), (II), (III)

| # | Structure | Mass calculated | M + H+ found | R$_t$ [min] LC-MS method A/B | TβR activity 0 >10 uM + 1-10 uM ++ 0.5-1 uM +++ <0.5 uM |
|---|---|---|---|---|---|
| 123 | 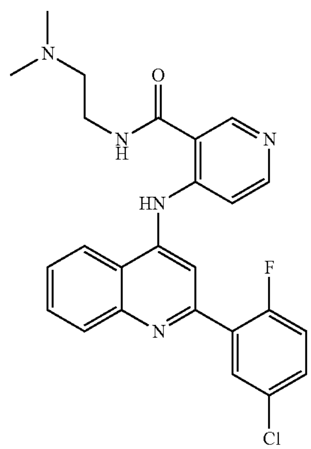 [SMILES: CN(C)CCNC(=O)c1cnccc1Nc1cc(-c2cc(Cl)ccc2F)nc2ccccc12] | 463.9 | 464 | 1.43 method B | +++ |
| 124 | 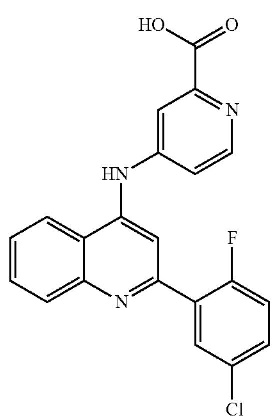 [SMILES: O=C(O)c1cc(Nc2cc(-c3cc(Cl)ccc3F)nc3ccccc23)ccn1] | 393.8 | 394 | 1.76 method B | + |
| 125 | 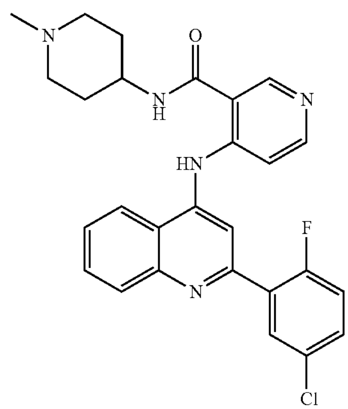 [SMILES: CN1CCC(NC(=O)c2cnccc2Nc2cc(-c3cc(Cl)ccc3F)nc3ccccc23)CC1] | 489.9 | 490 | 1.54 method B | +++ |

TABLE 1-continued

Compounds of formulae (I), (II), (III)

| # | Structure | Mass calculated | M + H+ found | R$_t$ [min] LC-MS method A/B | TβR activity<br>0 >10 uM<br>+ 1-10 uM<br>++ 0.5-1 uM<br>+++ <0.5 uM |
|---|---|---|---|---|---|
| 126 | 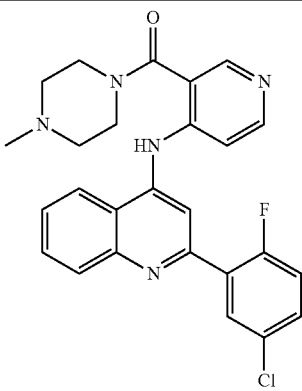 | 475.9 | 476 | 1.33 method B | + |
| 127 | 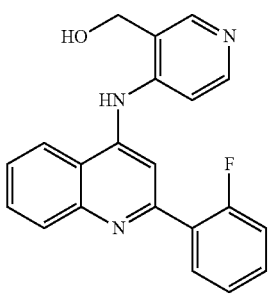 [SMILES: OCc1cnccc1Nc1cc(-c2ccccc2F)nc2ccccc12] | 345.4 | 346 | 1.42 method B | +++ |

LC-MS Method A

Mass spectrum: MH+; Agilent instrumentation series 1100; electrospray positive mode; scan 85-1000 m/z; fragmentation by voltage variable; gas temperature 300° C.; Solvents Lichrosolv quality Merck KGaA LC column: Chromolith Speed ROD RP18e, 50×4.6 mm$^2$ Eluent A: 0.1% trifluoroacetic acid in water;

Eluent B: 0.1% trifluoroacetic acid in acetonitrile

Gradient: 5% to 100% solvent B in 2.6 minutes

Flow: 2.4 ml/min

UV detection: 220 nm

LC-MS Method B

Mass spectrum: MH+; Agilent instrumentation series 1100; electrospray positive mode; scan 85-1000 m/z; fragmentation by voltage variable; gas temperature 300° C.; Solvents Lichrosolv quality Merck KGaA LC column: Chromolith Speed ROD RP18e, 50×4.6 mm$^2$ Eluent A: 0.05% formic acid in water;

Eluent B: 0.04% formic acid in acetonitrile

Gradient: 4% to 100% solvent B in 2.8 minutes plus 0.5 min post wash at 100% B

Flow: 2.4 ml/min

UV detection: 220 nm

In a highly preferred embodiment of the invention, hetarylaminoquinoline compounds of formulae (I), (II), (III) and the above embodiments are provided, which are selected from the group of compounds in Table 2.

TABLE 2

Highly preferred compounds of formulae (I), (II), (III)

| # | Structure |
|---|---|
| 003 | 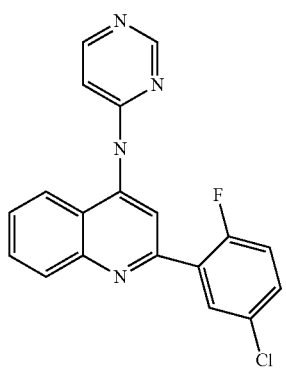 [SMILES: Fc1ccc(Cl)cc1-c1cc(Nc2ccncn2)c2ccccc2n1] |

TABLE 2-continued

Highly preferred compounds of formulae (I), (II), (III)

| # | Structure |
|---|---|
| 008 | 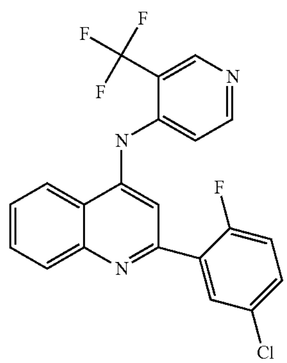 [SMILES: Fc1ccc(Cl)cc1-c1cc(Nc2ccncc2C(F)(F)F)c2ccccc2n1] |
| 019 | 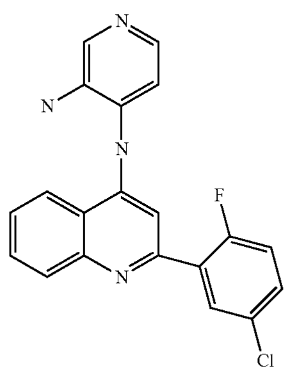 [SMILES: Nc1cnccc1Nc1cc(-c2cc(Cl)ccc2F)nc2ccccc12] |
| 023 | 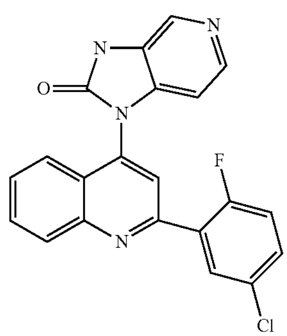 [SMILES: O=c1[nH]c2cnccc2n1-c1cc(-c2cc(Cl)ccc2F)nc2ccccc12] |
| 038 | 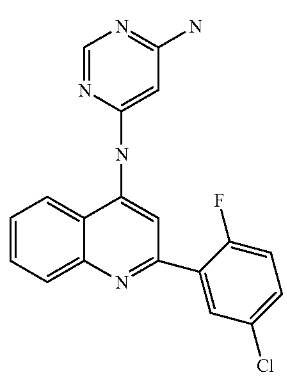 [SMILES: Nc1cc(Nc2cc(-c3cc(Cl)ccc3F)nc3ccccc23)ncn1] |
| 043 | 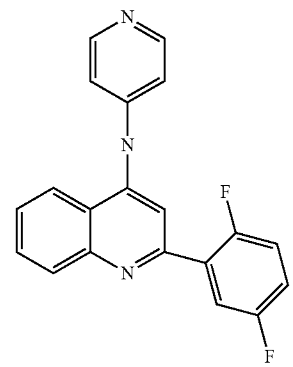 |
| 044 | 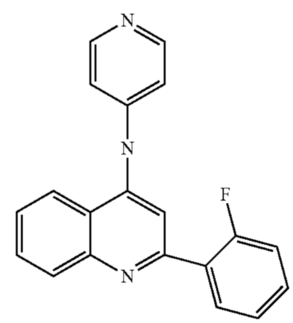 [SMILES: Fc1ccccc1-c1cc(Nc2ccncc2)c2ccccc2n1] |
| 045 | 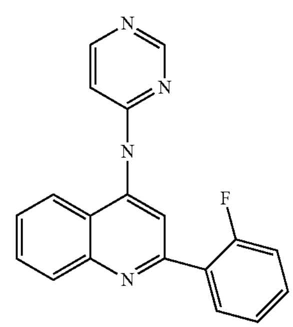 [SMILES: Fc1ccccc1-c1cc(Nc2ccncn2)c2ccccc2n1] |
| 056 | 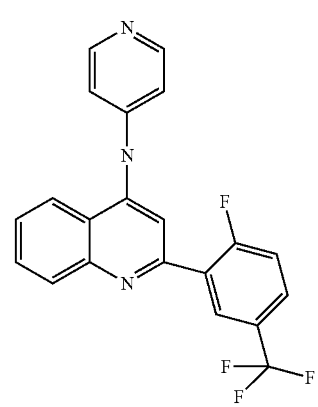 [SMILES: Fc1ccc(C(F)(F)F)cc1-c1cc(Nc2ccncc2)c2ccccc2n1] |

TABLE 2-continued

Highly preferred compounds of formulae (I), (II), (III)

| # | Structure |
|---|---|
| 057 | 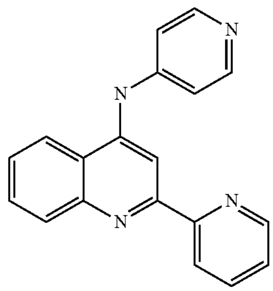 [SMILES: c1ccc(-c2cc(Nc3ccncc3)c3ccccc3n2)nc1] |
| 059 | 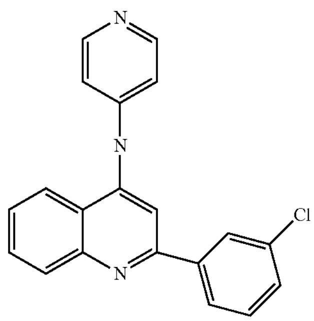 [SMILES: Clc1cccc(-c2cc(Nc3ccncc3)c3ccccc3n2)c1] |
| 068 | 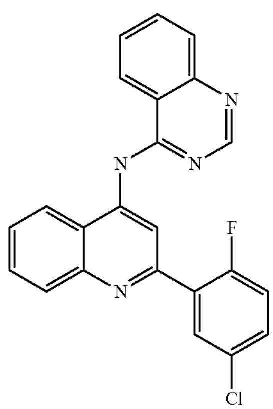 [SMILES: Fc1ccc(Cl)cc1-c1cc(Nc2ncnc3ccccc23)c2ccccc2n1] |
| 069 | 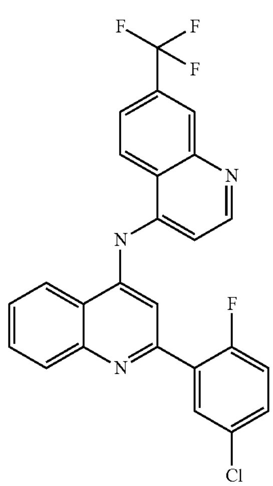 [SMILES: Fc1ccc(Cl)cc1-c1cc(Nc2ccnc3cc(C(F)(F)F)ccc23)c2ccccc2n1] |
| 075 | |
| 078 | |
| 084 | |

TABLE 2-continued
Highly preferred compounds of formulae (I), (II), (III)
| # | Structure |
|---|---|
| 090 | 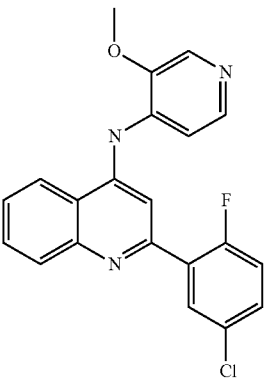 [SMILES: COc1cnccc1Nc1cc(-c2cc(Cl)ccc2F)nc2ccccc12] |
| 093 | 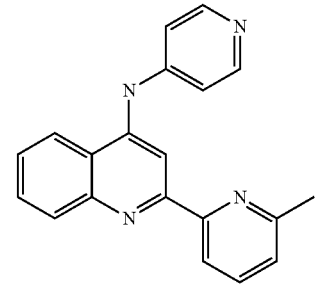 [SMILES: Cc1cccc(-c2cc(Nc3ccncc3)c3ccccc3n2)n1] |
| 105 | 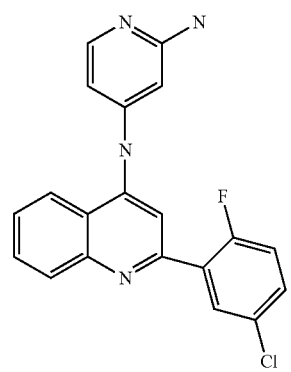 |
| 107 | 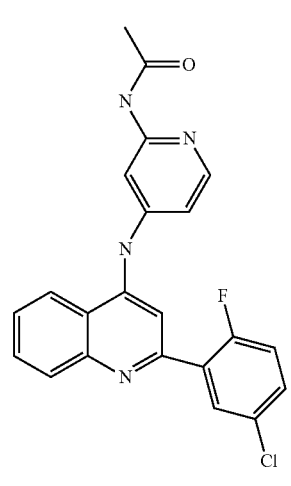 [SMILES: CC(=O)Nc1cc(Nc2cc(-c3cc(Cl)ccc3F)nc3ccccc23)ccn1] |
| 113 | 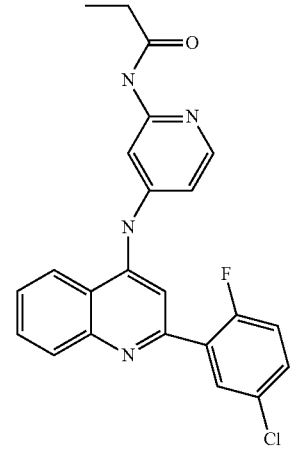 [SMILES: CCC(=O)Nc1cc(Nc2cc(-c3cc(Cl)ccc3F)nc3ccccc23)ccn1] |
| 118 | 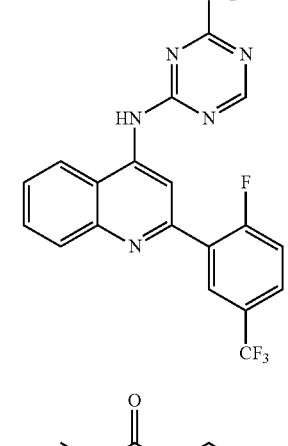 |
| 119 | 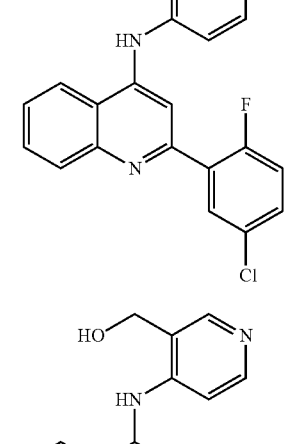 |
| 120 | 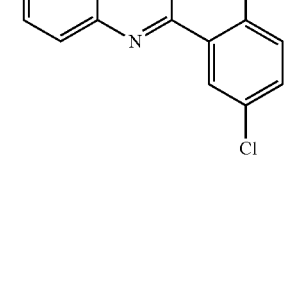 |

TABLE 2-continued

Highly preferred compounds of formulae (I), (II), (III)

| # | Structure |
|---|---|
| 121 | 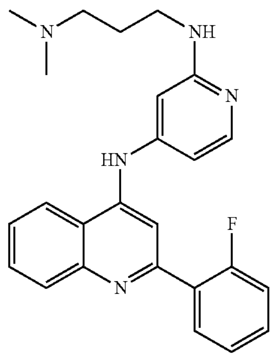 [SMILES: CN(C)CCCNc1cc(Nc2cc(-c3ccccc3F)nc3ccccc23)ccn1] |
| 122 | 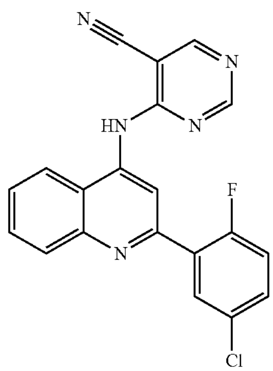 [SMILES: N#Cc1cncnc1Nc1cc(-c2cc(Cl)ccc2F)nc2ccccc12] |
| 123 | 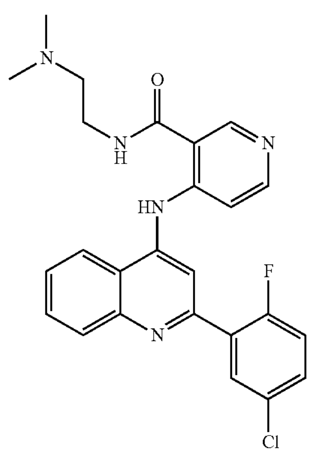 [SMILES: CN(C)CCNC(=O)c1cnccc1Nc1cc(-c2cc(Cl)ccc2F)nc2ccccc12] |
| 125 | |

In another aspect of the invention, the compounds [2-(5-Chloro-2-fluoro-phenyl)-quinazolin-4-yl]-(pyridin-4-yl)-amine and [2-(5-Chloro-2-fluoro-phenyl)-quinolin-4-yl]-(pyridin-4-yl)-amine are disclaimed from one or more subject-matters (including compounds of any formulae hereunder and/or medicaments, compositions and/or uses thereof), which are sought in any embodiment of the present invention.

The quinoline derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions. Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia) and several organic bases (piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to water, THF, tert. butanol, tert. amylalcohol, NMP, triethylamine and/or dioxane.

Depending on the conditions used, the reaction time is between a few minutes and 14 days, the reaction temperature is between about −30° C. and 140° C., normally between -10° C. and 130° C., particularly preferably between 30° C. and 125° C.

The present invention also relates to a process for manufacturing compounds of formula (I) comprising the steps of:

(a) reacting a compound of formula (IV)

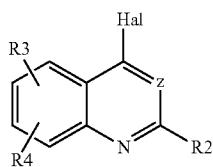
(IV)

wherein Z, R2, R3, R4 and Hal have the meaning as defined above, with a compound of formula (V)

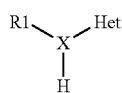
(V)

wherein X, R1 and Het have the meaning as defined above under the proviso that R1, R5 together are excluded, to yield a compound of formula (I)

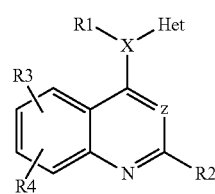
(I)

wherein X, Z, R1, R2, R3, R4 and Het have the meaning as defined above under the proviso that R1, R5 together are excluded, and optionally (b) converting a base or an acid of the compound of formula (I) into a salt thereof.

The quinoline derivatives of formula (I) are accessible via the route above. The starting materials, including the compounds of formulae (IV) and (V), are usually known to the skilled artisan, or they can be easily prepared by known methods.

Particularly, the compounds of formula (IV) are accessible via two different routes. In a first embodiment of the synthesis routes, the compounds of formula (IV) can be prepared by a process (A) comprising the steps of:

(a) reacting a compound of formula (VI)

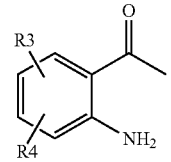
(VI)

wherein R3 and R4 have the meaning as defined above, with a compound of formula (VII)

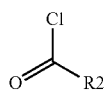
(VII)

wherein R2 has the meaning as defined above, to yield a compound of formula (VIII)

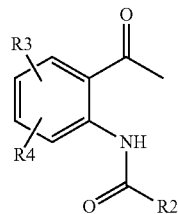
(VIII)

wherein R2, R3 and R4 have the meaning, as defined above, (b) reacting the compound of formula (VIII) in an alkaline milieu to yield a compound of formula (IX)

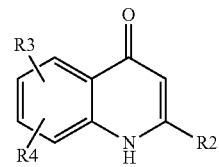
(IX)

wherein R2, R3 and R4 have the meaning as defined above, (c) reacting the compound of formula (IX) with a halogenating agent to yield a compound of formula (IV)

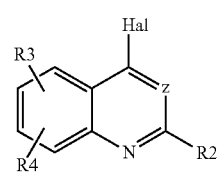
(IV)

wherein Z is CH and R2, R3, R4 and Hal have the meaning as defined above, and optionally
(d) converting a base or an acid of the compound of formula (I) into a salt thereof.

In more detail, amino acetophenone of formula (VI) is acylated with an acid derivative of formula (VII), such as a benzoic acid derivative, to give an amide of formula (VIII), which is treated with a strong base, preferably KOBut, to be condensed, yielding quinolinone of formula (IX). Halogenation with POHal$_3$ or PHal$_5$, wherein Hal has the meaning as defined above, gives a halogen derivative of formula (IV).

In a second embodiment of the synthesis routes, the compound of formula (IV) can be prepared by another process (B) comprising the steps of:
(a) reacting a halogenating agent with a compound of formula (X)

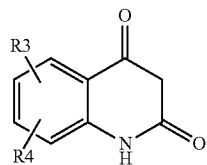

wherein R3 and R4 have the meaning as defined above, to yield a compound of formula (XI)

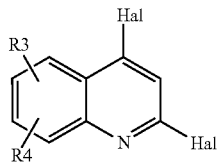

wherein R3, R4 and Hal have the meaning as defined above,
(b) reacting the compound of formula (XI) with a compound selected from the group of boronic acid, boronic ester, tin organics and boron triflates, each of which is substituted by R2 having the meaning as defined above, to yield a compound of

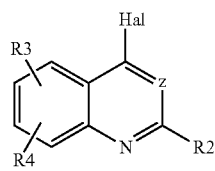

wherein Z is CH and R2, R3, R4 and Hal have the meaning as defined above,
and optionally
(c) converting a base or an acid of the compound of formula (I) into a salt thereof.

In more detail, tetrahydro-quinoline-dione of formula (X) is transferred to 2,4-halo-quinoline of formula (XI) by treatment with one or more halogenating agents, preferably POCl$_3$ or POBr$_3$ and/or the corresponding PHal$_5$, wherein Hal has the meaning as defined above. Treatment of quinoline of formula (X) under Pd0 catalysis with a boronic acid or boronic ester type (i), or similar chemistries with tin organics type (ii) or boron triflates type (iii) yields a 2-R2-4-Hal-quinoline of formula (IV), wherein R2 and Hal have the meaning as defined above.

The starting materials of process (B), including the compound of formula (X), are usually known to the skilled artisan, or they can be easily prepared by known methods. In particular, the compounds of formula (X) are accessible via different routes. In a first embodiment of the synthesis routes, the compounds of formula (X) can be prepared by a process (C) comprising the steps of:
(a) reacting an acetylating agent with a compound of formula (XII)

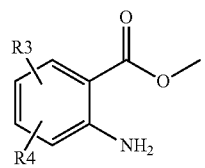

wherein R3 and R4 have the meaning as defined above, to yield a compound of formula (XIII)

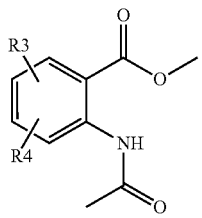

wherein R3 and R4 have the meaning as defined above,
(b) reacting the compound of formula (XIII) under basic conditions to yield a compound

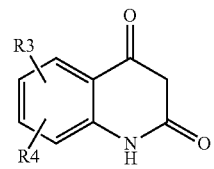

wherein R3 and R4 have the meaning as defined above,
and optionally
(c) converting a base or an acid of the compound of formula (I) into a salt thereof.

In more detail, starting from anthranilic esters of formula (XII) by reaction with acetylating agents, preferably AcCl, Ac$_2$O, Ac-imidazole, acetyl morpholine, Ac—CN or acetic acid, under coupling (dehydrating) conditions, acetamido benzoic ester derivatives of formula (XIII) are obtained, which can be cyclized under basic conditions, e.g. by use of KN(SiMe$_3$)$_2$ in a solvent like THF and/or toluene, to yield tetrahydro-quinoline-diones of formula (X) to be processed further like in process (B). The ester of formula (XII) can be produced via alcoholysis of a benzoxazine dione of formula (XXIII), which can be generated from anthranilic acids by phosgenation techniques.

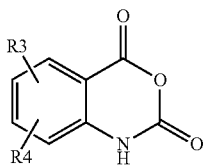

(XXIII)

In a second embodiment of the synthesis routes, the compounds of formula (X) can be prepared by a process (D) comprising the steps of:

(a) reacting a compound of formula (XII)

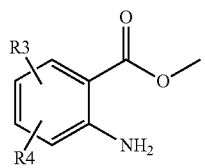

(XII)

wherein R3 and R4 have the meaning as defined above, with a compound of formula (XIV)

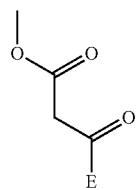

(XIV)

wherein E denotes OY or NYY; and Y has the meaning as defined above, to yield a compound of formula (XV)

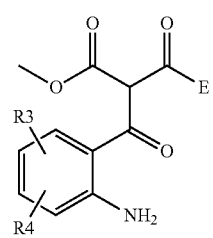

(XV)

wherein E denotes OY or NYY; and
Y, R3 and R4 have the meaning as defined above, (b) reacting the compound of formula (XV) in a solvent and under alkaline condition to yield a compound of formula (XVI)

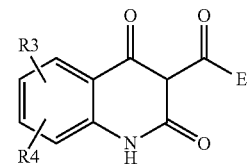

(XVI)

wherein E denotes OY or NYY; and
Y, R3 and R4 have the meaning as defined above, (c) reacting the compound of formula (XVI) under acidic or alkaline conditions to yield the compound of formula (X)

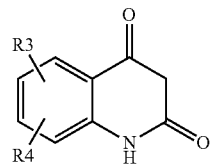

(X)

wherein R3 and R4 have the meaning as defined above, and optionally (c) converting a base or an acid of the compound of formula (I) into a salt thereof.

In more detail, starting from anthranilic acid ester of formula (XII) and reaction by malonic acid derivatives of formula (XIV) in the presence of a solvent and a base, acyl malonic acid derivatives of formula (XV) are formed, which can be cyclized with bases in a solvent to form tetrahydroquinolinones of formula (XVI). After acidic or alkaline hydrolysis/saponification and decarboxylation, tetrahydroquinoline-diones of formula (X) are formed, which can be further processed like in process (B).

Alternatively, the quinoline dione of formula (X) can be obtained from reaction of a corresponding aniline with malonic acid ester chloride (i.e. MeOCOCH$_2$COCl) or diethyl malonate (i.e. CH$_2$(COOEt)$_2$), followed by saponification, e.g. with NaOH, and cyclization mediated by polyphosphoric acid (PPA).

In another aspect of manufacturing the quinoline derivative of formula (I), the compounds of formula (V) are accessible via the following route. In a first embodiment of the synthesis route, 2-substituted 4-amino pyridines under formula (V) can be prepared by a process (E) comprising the steps of:

(a) reacting 2-bromo-4-nitro-pyridine-N-oxide with a compound of formula H—R6, wherein R6 has the meaning as defined above, to yield a compound of formula (XVII)

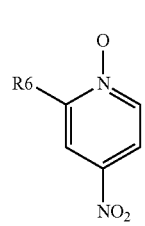

(XVII)

wherein R6 has the meaning as defined above, (b) reacting the compound of formula (XVII) under reducing conditions to yield a compound under formula (V)

wherein R6 has the meaning as defined above,
and optionally
(c) converting a base or an acid of the compound of formula (I) into a salt thereof.

In more detail, synthesis of 2-substituted 4-amino pyridines starts, for example, from commercial 2-bromo-4-nitro-pyridine-N-oxide, which is reacted with an alcohol, phenol, amine or aniline under basic conditions to give the compound of formula (XVII), which can be reduced to the corresponding 4-amino pyridine derivatives.

In a second embodiment of the synthesis route, the 3-substituted 4-amino-pyridines under formula (V) can be prepared by a process (F) comprising the steps of:
(a) reacting 3-fluoro-4-nitro-pyridine-N-oxide with a compound of formula H—R5, wherein R5 has the meaning as defined above, to yield a compound of formula (XVII)

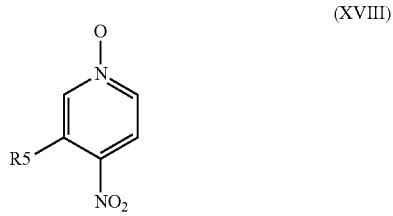

(XVIII)

wherein R5 has the meaning as defined above,
(b) reacting the compound of formula (XVIII) under reducing conditions to yield a compound under formula (V)

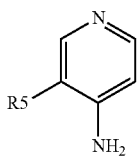

wherein R5 has the meaning as defined above,
and optionally
(c) converting a base or an acid of the compound of formula (I) into a salt thereof.

In more detail, synthesis of 3-substituted 4-amino pyridines starts, for example, from commercial 3-fluoro 4-nitro-pyridine-N-oxide, which is reacted with an alcohol, phenol, amine or aniline under basic conditions to give the intermediate of formula (XVIII), which can be reduced to the corresponding 4-amino pyridine derivatives.

Accordingly, any compound of formulae (IV) to (XVIII) can be purified, provided as intermediate product and used as starting material for the preparation of compounds of formula (I). It is preferred, however, that the compounds of formulae (IV), (V), (IX), (X) and/or (XI) are provided as intermediate product and used as starting material for the preparation of compounds of formula (I), more preferably the compounds of formulae (IV), (V), (IX) and/or (XI), most preferably the compounds of formulae (IV) and/or (V), highly preferably the compounds of formulae (IV) and (V). The reaction of the compound of formula (IV) with the compound of formula (V) results in the addition to the compound of formula (I). In more detail, the compound of formula (IV) can be reacted with a compound of formula (V) using Pd0 chemistry, like in a Buchwald-Hartwig reaction, to produce a compound of formula (I). Preferably, aniline under formula (V) is reacted to produce final parent compound of 2-R2-4-Het-amino-quinoline, wherein R2 and Het have the meaning as defined above, such as 2-(2-fluoro-5-chloro-phenyl)-4-(3-methoxy-pyridyl-4-amino)-quinoline.

Alternative procedures via 2-aryl/hetaryl-4-amino and 4-tertButoxy-quinolines can be taken from Moore et al. THL 20, 1277 (1963); Strekowski et al. Heterocycles 29, 539 (1989); Strekowski et al. JMC 34, 1739 (1991); Strekowski et al. J. Med. Chem. 46, 1242 (2003); Strekowski et al. J. Org. Chem. 62, 4193 (1997) or Paliakov et al. THL 45, 4093 (2004). Moreover, quinazolin-4-yl thiazol-2-yl amines are described by Pierce et al. J. Med. Chem. 48, 1278 (2005). In another aspect of synthesis, route via 4-F-quinolines can be used according to Kiselyov et al. THL 35, 7597 (1994) or a Pd mediated multi component reaction to form substituted quinolines as described by Abbiatti et al. J. Org. Chem. 70 (16), 6454 (2005).

The compounds of formula (I) can be modified, like hydrogenated or metal-reduced, to remove the chlorine, or put into a substitution reaction, and/or to be transformed with a strong acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or an carboxylic acid or an sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or caesium. Organic bases, like $Et_3N$, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd $(PPh_3)_4$, or $Pd(OAc)_2$, $PdCl_2$ type precursors of Pd0 catalysts have advanced to more complex ones with more efficient ligands. In C—C arylations instead of boronic acids and esters (Stille coupling), aryl-trifluoroborate potassium salts (Suzuki-Miyaura coupling), organo silanes (Hiyama coupling), Grignard reagents (Kumada), zink organyles (Negishi coupling) and tin organyles (Stille coupling) are useful. This experience can be transferred to N- and O-arylations, Numerous papers and methods are available and useful for the one skilled in the art in respect of N-arylation and even of electron deficient anilines (Biscoe et al. JAGS 130, 6686 (2008)), and with aryl chlorides and anilines (Fors et al. JACS 130, 13552 (2008)) as well as for O-arylation by using Cu catalysis and Pd catalysis.

In a synthetic approach to 3-substituted 4-X—N-heteroaryl quinolines, wherein X has the meaning as defined above, the modified compounds under formula (I) can be prepared by a process (G) comprising the steps of:
(a) reacting a compound of formula (XIX)

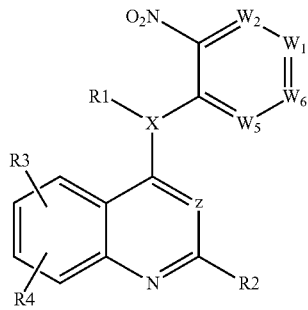
(XIX)

wherein X, Z, W1, W2, W5, W6, R1, R2, R3 and R4 have the meaning as defined above,
under reducing conditions to yield a compound of formula (XX)

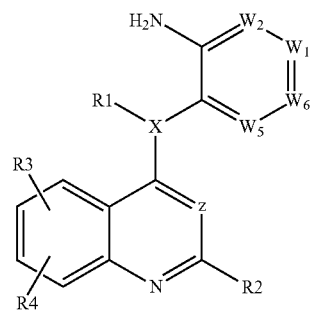
(XX)

wherein X, Z, W1, W2, W5, W6, R1, R2, R3 and R4 have the meaning as defined above,
(b) reacting the compound of formula (XX) under acylating conditions to yield a compound of formula (XXI)

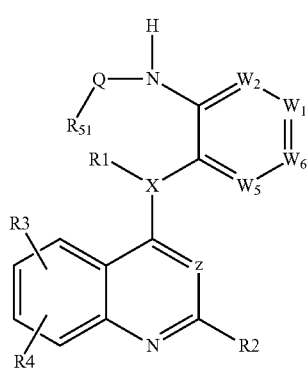
(XXI)

wherein Q denotes —CO—, —SO$_2$—, —NY—CO—, —CO—NY—, —COO—, NY—SO$_2$ or a bond;
R51 denotes Y, -Alk-NYY, -Alk-OY, Het$^3$, —CO—R2 or —CO-Het$^2$; and
X, Z, W1, W2, W5, W6, R1, R2, R3, R4, Y, Alk, Het$^2$ and Het$^3$ have the meaning as defined above, (c) reacting the compound of formula (XXI) under acylating conditions, followed by acidic conditions, to yield a compound of formula (XXII)

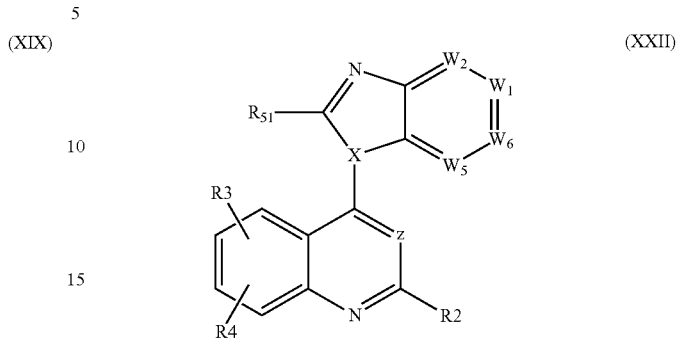
(XXII)

wherein R51 denotes Y, -Alk-NYY, -Alk-OY, Het$^3$, —CO—R2 or —CO-Het$^2$; and
X, Z, W1, W2, W5, W6, R2, R3, R4, Y, Alk, Het$^2$ and Het$^3$ have the meaning as defined above,
and optionally
(d) converting a base or an acid of the compound of formula (I) into a salt thereof.

In more detail, 3-nitro-4-amino pyridine can be used to synthesize 2-R2-4-(3-nitro-pyridyl-4-amino)-quinolines of formula (XXI) from an appropriate intermediate of formula (IV). After reduction of the 3-nitro function, the freed aniline can be alkylated, acylated, carbaminated, sulfamidated, sulfamoylated, or acylated and consecutively benzimidazoylated utilising both 3- and 4-amino groups. In step (b), the compound of formula (XX) is reacted under acylating conditions with an activated carboxylic acid derivative, particularly a chloride, anhydride, active ester, an activated sulfonic acid derivative, a carbonate or an isocyanate. In step (c), the resulting compound of formula (XXI) is reacted under acylating conditions with an activated carboxylic acid derivative, followed by acid treatment to cyclise the initially formed amide to the corresponding imidazole.

In the final step of the processes above, a salt of the compound according to formulae (I) to (XXII), preferably formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal. hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hem isuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, mangariese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexyl-amine, diethanolamine, diethylamine, 2-diethylaminoethanol, 2-dimethylaminoethanol, ethanolamine, ethylenediamine, N-ethylmorpholine, N-ethylpiperidine, glucamine, glucoseamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternized using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for inhibiting ATP consuming proteins, particularly kinases. The term "inhibition" denotes any reduction in kinase activity, which is based on the action of the specific inventive compounds capable to interact with the target kinase in such a manner that makes recognition, binding and blocking possible. The compounds are characterized by such a high affinity to at least one kinase, which ensures a reliable binding and preferably a complete blocking of kinase activity. More preferably, the substances are mono-specific in order to guarantee an exclusive and directed recognition with the chosen single kinase target. In the context of the present invention, the term "recognition"—without being limited thereto—relates to any type of interaction between the specific substances and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In an embodiment of the present invention, the kinases either belong to the group of tyrosine kinases and serine/threonine kinases. In a preferred embodiment of the invention, the kinases are selected form the group of TGF-beta, PDK1, Met, PKD1, MINK1, SAPK2-alpha, SAPK2-beta, MKK1, GCK, HER4, ALK1, ALK2, ALK4, ALK5 and TbR type II. It is more preferred to inhibit serine/threonine kinases. Most preferred kinases to be inhibited are TGF-beta receptor kinase and/or ALK5, highly preferably TGF-beta receptor kinase.

The kinase are especially half inhibited if the concentration of the compounds amounts to less than 1.000 nM, preferably less than 500 nM, more preferably less than 300 nM, most preferably less than 100 nM. Such concentration is also referred to as IC50.

The use according to the previous paragraphs of the specification may be either performed in-vitro or in-vivo models. The inhibition can be monitored by the techniques described in the course of the present specification. The in-vitro use is preferably applied to samples of humans suffering from cancer, tumor growth, metastatic growth, fibrosis, restenosis, HIV infection, neurodegenartive disorders, e.g. Alzheimer's disease, atherosclerosis, inflammation and disorders of wound healing, angiogenesis, cardiovascular system, bone, CNS and/or PNS. Testing of several specific compounds and/or derivatives thereof makes the selection of that active ingredient possible that is best suited for the treatment of the human subject. The in-vivo dose rate of the chosen derivative is advantageously pre-adjusted to the kinase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of kinase activity if expedient.

The invention furthermore relates comprising at least one compound according to the invention and/or pharmaceutically usable derivatives, salts, solvates and stereoisomers thereof, including mixtures thereof in all ratios, and optionally excipients and/or adjuvants.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Consequently, the invention also relates to a pharmaceutical composition comprising as active ingredient an effective amount of at least one compound according to formula (I) and/or physiologically acceptable salts thereof together with pharmaceutically tolerable adjuvants.

A "medicament", "pharmaceutical composition" or "pharmaceutical formulation" in the meaning of the invention is any agent in the field of medicine, which comprises one or more compounds of formula (I) or preparations thereof and can be used in prophylaxis, therapy, follow-up or aftercare of patients who suffer from diseases, which are associated with kinase activity, in such a way that a pathogenic modification of their overall condition or of the condition of particular regions of the organism could establish at least temporarily.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The present compounds are suitable for combination with known anticancer agents. These known anticancer agents include the following: (1) estrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors. The present compounds are particularly suitable for administration at the same time as radiotherapy. The synergistic effects of inhibiting VEGF in combination with radiotherapy have been described in the art (see WO 00/61186).

"Estrogen receptor modulators" refers to compounds which interfere with or inhibit the binding of estrogen to the receptor, regardless of mechanism. Examples of estrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cisretinoic acid, 9-cisretinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumor necrosis factors, intercalators, microtubulin inhibitors and topoisomerase inhibitors. Examples of cytotoxic agents include, but are not limited to, tirapazimine, sertenef, cachectin, ifosfamide, tasonermin, lonidamine, carboplatin, altretamine, prednimustine, dibromoodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans) bismu-(hexane-1,6-diamine)-mu-[diamineplatinum(II)]bis-[diamine(chloro)platinum(II)] tetrachloride, diarizidinyl-spermine, arsenic trioxide, 1-(11-dodecylamino-10-hydroxyundecyl)-3,7-dimethylxanthine, zorubicin, idarubicin, daunorubicin, bisantrene; mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Further examples of cytotoxic agents being microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoroo-N-(3-fluoro-4-methoxyphenyl)benzenesulfonamide, anhydrovinblastine, N,N-dimethyl-L-valyl-L-valyl-N-methyl-L-valyl-L-prolyl-L-prolinet-butylamide, TDX258 and BMS188797.

Further examples of cytotoxic agents being topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoroo-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',': 6,7)naphtho(2,3-d)-1,3-dioxol-6-one, 2,3-(methylenedioxy)-5-methyl-7-hydroxy-8-methoxybenzo[c]phen-anthridinium, 6,9-bis[(2-aminoethyl)amino]benzo[g]isoquinoline-5,10-dione, 5-(3-amino-propylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]-amino]-3-hydroxy-7H-indeno[2,1-c]quinolin-7-one and dimesna.

"Antiproliferative agents" include antisense RNA and DNA oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2',deoxycytidine, N-[5-(2,3-dihydrobenzofuryl) sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thie-noyl-L-glutamic acid, aminopterin, 5-fluoroouracil, alanosine, 11-acetyl-8-(carbamoyloxy-methyl)-4-formyl-6-methoxy-14-oxa-1,11-diazatetracyclo(7.4.1.0.0) tetradeca-2,4,6-trien-9-ylacetic acid ester, swainsonine, lometrexol, dexrazoxane, methioninase, 2'-cyanoo-2'-deoxy-N4-palmitoyl-1-B-D-arabinofuranosyl cytosine and 3-aminopyridine-2-carbox-aldehyde thiosemicarbazone. "Antipro-liferative agents" also include monoclonal antibodies to growth factors other than those listed under "angiogenesis inhibitors", such as trastuzumab, and tumor suppressor genes, such as p53, which can be delivered via recombinant virus-mediated gene transfer (see U.S. Pat. No. 6,069,134; for example).

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient (s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, such as lactose or starch, magnesium stearate, talc, and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavor, preservative, dispersant and dye may likewise be present.

Capsules are produced by preparing a powder mixture as described above and filling shaped gelatin shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatin, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatin or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavor, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavor additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The active ingredient according to the invention can also be fused or complexed with another molecule that promotes the directed transport to the destination, the incorporation and/or distribution within the target cells.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylam ido-phenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eyedrops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurized dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is orally or parenterally administered, more preferably orally. In particular, the active ingredient is provided in a water-soluble form, such as a pharmaceutically acceptable salt, which is meant to include both acid and base addition salts. Furthermore, the compounds of formula (I) and salts thereof, may be lyophilized and the resulting lyophilizates used, for example, to produce preparations for injection. The preparations indicated may be sterilized and/or may comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, cancer and/or fibrotic diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by kinase activity. It is particularly preferred that the diseases are selected from the group of cancer, tumor growth, metastatic growth, fibrosis, restenosis, HIV infection, neurodegenerative disorders, atherosclerosis, inflammation and disorders of wound healing, angiogenesis, cardiovascular system, bone, CNS and/or PNS. It shall be understood that the host of the compound is included in the present scope of protection according to the present invention.

Particular preference is given to the treatment and/or monitoring of a tumor and/or cancer disease. The tumor is preferably selected from the group of tumors of the squamous epithelium, bladder, stomach, kidneys, head, neck, esophagus, cervix, thyroid, intestine, liver, brain, prostate, urogenital tract, lymphatic system, larynx and/or lung.

The tumor is furthermore preferably selected from the group of lung adenocarcinoma, small-cell lung carcinomas, pancreatic cancer, glioblastomas, colon carcinoma and breast carcinoma. In addition, preference is given to the treatment and/or monitoring of a tumor of the blood and immune system, more preferably for the treatment and/or monitoring of a tumor selected from the group of acute myeloid leukemia, chronic myeloid leukemia, acute lymphatic leukemia and/or chronic lymphatic leukemia. Such tumors can also be designated as cancers in the meaning of the invention.

In a more preferred embodiment of the invention, the aforementioned tumors are solid tumors.

In another preferred embodiment of the invention, the compounds of formula (I) are applied for the prophylactic or therapeutic treatment and/or monitoring of retroviral diseases or for the manufacture of a medicament for the prophylactic or therapeutic treatment and/or monitoring of retroviral diseases, respectively, preferably of retroviral immune diseases, more preferably an HIV infection. The agent can be either administered to reducing the likelihood of infection or to prevent the infection of a mammal with a retrovirus and the onset of the disease in advance, or to treat the disease caused by the infectious agent. Particularly, later stages of virus internalization can be reduced and/or prevented. It is the intention of a prophylactic inoculation to reduce the likelihood of infection or to prevent the infection with a retrovirus after the infiltration of single viral representatives, e.g. into a wound, such that the subsequent propagation of the virus is strictly diminished, or it is even completely inactivated. If an infection of the patient is already given, a therapeutic administration is performed in order to inactivate the retrovirus being present in the body or to stop its propagation. Numerous retroviral diseases can be successfully combated by applying the inventive compounds, particularly AIDS caused by HIV.

The quinoline compounds according to the present invention are also useful against diseases selected from the group of cardiovascular diseases, preferably congestive heart failure, dilated cardiomyopathy, myocarditis or vascular stenosis associated with atherosclerosis, angioplasty treatment or surgical incisions or mechanical trauma; kidney diseases associated with fibrosis and/or sclerosis including glomerulonephritis of all etiologies, diabetic nephropathy and all causes of renal interstitial fibrosis including hypertension, complications of drug exposure, HIV-associated nephropathy, transplant nephropathy, chronic ureteral obstruction; hepatic diseases associated with excessive scarring and progressive sclerosis including cirrhosis due to all etiologies, disorders of the biliary tree and hepatic dysfunction attributable to infections such as hepatitis virus or parasites; syndromes associated with pulmonary fibrosis with consequential loss of gas exchange or ability to efficiently move air into and out of the lungs including adult respiratory distress syndrome, idiopathic pulmonary fibrosis or pulmonary fibrosis due to infectious or toxic agents or autoimmune disease; collagen vascular disorders of a chronic or persistent nature including progressive systemic sclerosis, polymyositis, scleroderma, dermatomyositis, fascists or Raynaud's syndrome or arthritic conditions, preferably rheumatoid arthritis; eye diseases associated with fibroproliferative states including proliferative vitreoretinopathy of any etiology or fibrosis associated with ocular surgery such as retinal reattachment, cataract extraction or drainage procedures of any kind; excessive or hypertrophic scar formation in the dermis occurring during wound healing resulting from trauma or surgical wounds; disorders of the gastrointestinal tract associated with chronic inflammation, preferably Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis or surgical wounds; neurological conditions characterized by TGF-β production or enhanced sensitivity to TGF-β including states post-traumatic or hypoxic injury, Alzheimer's disease and Parkinson's disease; and diseases of the joints involving scarring sufficient to impede mobility or produce pain including states post-mechanical or surgical trauma, osteoarthritis and rheumatoid arthritis.

The quinoline compounds according to the present invention are also useful in the context of diseases that benefit from the improvement of lung function; and wherein the diseases are selected from the group of emphysema, chronic bronchitis, chronic obstructive pulmonary disease, pulmonary edema, cystic fibrosis, occlusive lung disease, acute respiratory deficiency syndrome, asthma, radiation-inducted injury of the lung, lung injuries resulting from infectious causes, inhaled toxins or circulating exogenous toxins, aging and genetic predisposition to impaired lung function.

The quinoline compounds according to the present invention are also useful if the diseases are selected from a proinflammation response, fibroproliferative response or both. Preferably, said proinflammation response is multiple sclerosis, IBD, rheumatoid arthritis, rheumatoid spondylitis, osteoarthritis, gouty arthritis, other arthritic conditions, sepsis, septic shock, endotoxic shock, Gram-negative sepsis, toxic shock syndrome, asthma, adult respiratory distress syndrome, stroke, reperfusion injury, CNS injury, psoriasis, restenosis, cerebral malaria, chronic pulmonary inflammatory disease, silicosis, pulmonary sarcosis, a bone resorption disease, graft-versus-host reaction, Crohn's Disease, ulcerative colitis or pyresis.

In another preferred aspect, said fibroproliferative response is selected from the group of glomerulonephritis; diabetic nephropathy; renal interstitial fibrosis; renal fibrosis resulting from complications of drug exposure; HIV-associated nephropathy; transplant nephropathy; liver cirrhosis due to all etiologies; disorders of the biliary tree; hepatic dysfunction attributable to infections; pulmonary fibrosis; adult respiratory distress syndrome; chronic obstructive pulmonary disease; idiopathic pulmonary fibrosis; acute lung injury; pulmonary fibrosis due to infectious or toxic agents; congestive heart failure; dilated cardiomyopathy; myocarditis; vascular stenosis; progressive systemic sclerosis; polymyositis; scleroderma; dermatomyositis; fascists; Raynaud's syndrome, rheumatoid arthritis; proliferative vitreoretinopathy; and fibrosis associated with ocular during wound healing resulting from trauma or surgical wounds. Said fibroproliferative response can also be associated with a renal disorder, a vascular disorder, a fibrosis, an autoimmune disorder, an eye disease, excessive scarring, a neurological condition, myelofibrosis, tissue thickening, nasal polyposis, a polyp, liver cirrhosis or osteoporosis. Herein, said renal disorder is particularly glomerulonephritis, diabetic nephropathy, renal interstitial fibrosis, renal fibrosis in transplant patients receiving cyclosporin and HIV-associated nephropathy; and wherein said vascular disorder is progressive systemic sclerosis, polymyositis, scleroderma, dermatomyositis, eosinophilic fascitis, morphea or Raynaud's syndrome; and wherein said fibrosis is associated with adult respiratory distress syndrome, idiopathic pulmonary fibrosis, interstitial pulmonary fibrosis, cardiac fibrosis, keloid formation or hypertrophic scarring; and wherein said autoimmune disorder is systemic lupus erythematosus, scleroderma, or rheumatoid arthritis; and wherein said eye disease is retinal detachment, cataracts, or glaucoma; and wherein said neurological condition is CNS injury, Alzheimer's disease or Parkinson's disease.

The invention also relates to the use of compounds according to formula (I) and/or physiologically acceptable salts thereof for the prophylactic or therapeutic treatment and/or monitoring of diseases that are caused, mediated and/or propagated by kinase activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by kinase activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

In another embodiment of the present invention, the compounds according to formula (I) and/or physiologically acceptable salts thereof are used for the production of a combination preparation for the prophylactic or therapeutic treatment and/or monitoring of solid tumors, wherein the combination preparation comprises an effective amount of an active ingredient selected from the group of (1) oestrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors.

The compounds of formula (I) according to the invention can be administered before or following an onset of disease once or several times acting as therapy. The aforementioned medical products of the inventive use are particularly used for the therapeutic treatment. A therapeutically relevant effect relieves to some extent one or more symptoms of an autoimmune disease, or returns to normality, either partially or completely, one or more physiological or biochemical parameters associated with or causative of the disease or pathological conditions. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disease or even prevent the initiation of diseases associated with increased kinase activity in advance or to treat the arising and continuing symptoms. The diseases as concerned by the invention are preferably cancer and/or fibrotic diseases. In the meaning of the invention, prophylactic treatment is advisable if the subject possesses any preconditions for the aforementioned physiological or pathological conditions, such as a familial disposition, a genetic defect, or a previously passed disease.

The prior teaching of the present specification concerning the pharmaceutical composition is valid and applicable without restrictions to the use of compounds according to formula (I) and their salts for the production of a medicament and/or combination preparation for prophylaxis and therapy of said diseases.

It is another object of the invention to provide a method for treating diseases that are caused, mediated and/or propagated by kinase activity, wherein an effective amount of at least one compound according to formula (I) and/or physiologically acceptable salts thereof is administered to a mammal in need of such treatment. The preferred treatment is an oral or parenteral administration. The treatment of the patients with cancer, tumor growth, metastatic growth, fibrosis, restenosis, HIV infection, neurodegenerative disorders, atherosclerosis, inflammation and disorders of wound healing, angiogenegsis, cardiovascular system, bone, CNS and/or PNS, or people bearing a risk of developing such diseases or disorders on the basis of existing preconditions by means of the compounds of formula (I) improves the whole-body state of health and ameliorates symptoms in these individuals. The inventive method is particularly suitable for treating solid tumors.

The method is particularly performed in such a manner that an effective amount of another active ingredient selected from the group of (1) estrogen receptor modulators, (2) androgen receptor modulators, (3) retinoid receptor modulators, (4) cytotoxic agents, (5) antiproliferative agents, (6) prenyl-protein transferase inhibitors, (7) HMG-CoA reductase inhibitors, (8) HIV protease inhibitors, (9) reverse transcriptase inhibitors and (10) further angiogenesis inhibitors is administered in combination with the effective amount of the compound of formula (I) and/or physiologically acceptable salts thereof.

In a preferred embodiment of the method, the treatment with the present compounds is combined with radiotherapy. It is even more preferred to administer a therapeutically effective amount of a compound according formula (I) in combination with radiotherapy and another compound from the groups (1) to (10) as defined above. The synergistic effects of inhibiting VEGF in combination with radiotherapy have already been described.

The prior teaching of the invention and its embodiments is valid and applicable without restrictions to the method of treatment if expedient.

In the scope of the present invention, novel hetarylaminoquinoline compounds of formula (I) are provided for the first time. The inventive compounds strongly and/or selectively target ATP consuming proteins like kinases, particularly TGF-β receptor kinases. The compounds of formula (I) and derivatives thereof are characterized by a high specificity and stability; low manufacturing costs and convenient handling. These features form the basis for a reproducible action, wherein the lack of cross-reactivity is included, and for a reliable and safe interaction with their matching target structures. The current invention also comprises the use of present hetarylaminoquinoline derivatives in the inhibition, the regulation and/or modulation of the signal cascade of kinases, especially the TGF-β receptor kinases, which can be advantageously applied as research and/or diagnostic tool.

Furthermore, medicaments and pharmaceutical compositions containing said compounds and the use of said compounds to treat kinase-mediated conditions is a promising, novel approach for a broad spectrum of therapies causing a direct and immediate reduction of symptoms in man and animal. The impact is of special benefit to efficiently combat severe diseases, such as cancer, inflammation and/or fibrotic diseases, either alone or in combination with other anti-cancer, anti-inflammatory or anti-fibrotic treatments. In addition to the aforementioned clinical pictures, the compounds of formula (I), their salts, isomers, tautomers, enantiomeric forms, diastereomers, racemates, derivatives, prodrugs and/or metabolites are also useful for the diagnosis and treatment of any illnesses arising from TGF-β kinase signaling, particularly associated with cell proliferation and cell migration to be inhibited. The low molecular weight inhibitors are applied either themselves and/or in combination with physical measurements for diagnostics of effectiveness of any method of treatment, such as surgery, immune-, radio- and/or chemotherapy; the latter means a targeted therapy with any NME (i.e. NCE and/or NBE) as mono- and/or on-target/off-target combination therapy.

Due to their surprisingly strong and/or selective inhibition of enzymes, which regulate cellular processes by transferring phosphate groups from ATP to protein, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

All the references cited herein are incorporated by reference in the disclosure of the invention hereby.

It is to be understood that this invention is not limited to the particular compounds, pharmaceutical compositions, uses and methods described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved.

EXAMPLE 1

Cellular Assay for Testing TGF-Beta Receptor I Kinase Inhibitors

As an example, the ability of the inhibitors to eliminate TGF-beta-mediated growth inhibition was tested. Cells of the lung epithelial cell line Mv1 Lu were sown in a defined cell density in a 96-well microtiter plate and cultivated overnight under standard conditions. Next day, the medium was replaced by medium which comprises 0.5% of FCS and 1 ng/ml of TGF-beta, and the test substances were added in defined concentrations, generally in the form of dilution series with 5 fold steps. The concentration of the solvent DMSO was constant at 0.5%. After a further two days, Crystal Violet staining of the cells was carried out. After extraction of the Crystal Violet from the fixed cells, the absorption was measured spectrophotometrically at 550 nm. It could be used as a quantitative measure of the adherent cells present and thus of the cell proliferation during the culture.

EXAMPLE 2

In-Vitro (Enzyme) Assay for Determination of the Efficacy of Inhibitors of the Inhibition of TGF-Beta-Mediated Effects The kinase assay was carried out as 384-well flashplate assay. 31.2 nM of GST-ALK5, 439 nM of GST-SMAD2 and 3 mM of ATP (with 0.3 µCi of $^{33}$P-ATP/well) were incubated in a total volume of 35 µl (20 mM of HEPES, 10 mM of $MgCl_2$, 5 mM of $MnCl_2$, 1 mM of DTT, 0.1% of BSA, pH 7.4) without or with test substance (5-10 concentrations) at 30° C. for 45 min. The reaction was stopped using 25 µl of 200 mM EDTA solution, filtered with suction at room temperature after 30 min, and the wells were washed with 3 times 100 µl of 0.9% NaCl solution. Radioactivity was measured in the TopCount. The $IC_{50}$ values were calculated using RS1. Above and below, all temperatures were indicated in ° C.

In the following examples, "conventional workup" means: water was added if necessary, the pH was adjusted, if necessary, to a value of between 2 and 10, depending on the constitution of the end product, the mixture was extracted with ethyl acetate or dichloromethane, the phases were separated, the organic phase was dried over sodium sulfate and evaporated, and the product was purified by chromatography on silica gel and/or by crystallization. $R_f$ values were determined on silica gel. The eluent was ethyl acetate/methanol 9:1.
Retention time $R_t$ [min] determination was carried out by LC (System 1):
Column: Chromolith SpeedROD RP18e, 50×4.6 mm$^2$
Gradient: A:B=96:4 to 0:100
Flow rate: 2.4 ml/min
Eluent A: water+0.05% formic acid,
Eluent B: acetonitrile+0.04% formic acid
Wavelength: 220 nm
Alternatively, retention time $R_t$ [min] determination was carried out by LC (System 2):
Column: Chromolith SpeedROD RP18e, 50×4.6 mm$^2$
Gradient: 2.6 min, A:B=95:5 to 0:100
Flow rate: 2.4 ml/min
Eluent A: water+0.1% of TFA (trifluorooacetic acid),
Eluent B: acetonitrile+0.1% of TFA
Wavelength: 220 nm

EXAMPLE 3

Synthesis of N-(2-Acetyl-phenyl)-5-chloro-2-fluoro-benzamide (M 291.71)

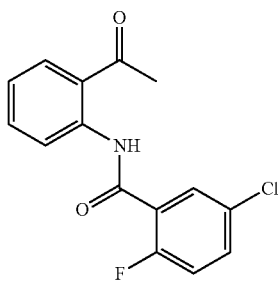 [SMILES: CC(=O)c1ccccc1NC(=O)c1cc(Cl)ccc1F]

70 g 2-amino acetophenone were reacted at ambient temperature in 2.5 l THF in presence of 177 ml N-ethyl diisopropylamine with 100 g 5-cloro-2-fluoro-benzoylchloride while temperature rose from 20 to 34° C. and white precipitate appeared. After one more night the suspension was filtered and the filtrate concentrated. Solution in THF at 80° C. was slowly diluted with water. After a night at ambient temperature precipitate was filtered and washed with water. After drying 149 g product was obtained as pinkish needles with $R_t$~2.49 min and correct M+H+ 292 in LC-MS system 1.

EXAMPLE 4

Synthesis of 2-(5-Chloro-2-fluoro-phenyl)-1H-quinolin-4-one (M 273.70)

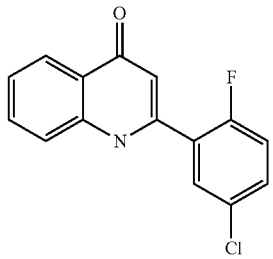 [SMILES: O=c1cc(-c2cc(Cl)ccc2F)[nH]c2ccccc12]

148 g N-(2-Acetyl-phenyl)-5-chloro-2-fluoro-benzamide (cf. Example 3) suspended in 4 l tert.-BuOH were charge in several portions with 171 g KOBut. The red solution was heated for 20 hrs at 75° C. to become brownish. After concentrating to about 1 l the slurry was poured slowly to 5 l water/ice, the pH adjusted with concentrated HCl to 1-2 to produce a yellow slurry. After 30 min the precipitate was filtered and washed with water and 2-PrOH. The moist precipitate was digerated and refluxed with 3 l MTB ether. After filtration 96 g of product were obtained with M+H+ 274 in LC-MS system 1.

EXAMPLE 5

Synthesis of 4-Bromo-2-(5-chloro-2-fluoro-phenyl)-quinoline (M 336.59)

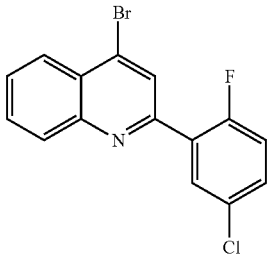 [SMILES: Fc1ccc(Cl)cc1-c1cc(Br)c2ccccc2n1]

105 g POBr$_3$ were added slowly at ambient temperature to 100 g 2-(5-Chloro-2-fluoro-phenyl)-1H-quinolin-4-one (cf. Example 4) dissolved in 3 l NMP. Temperature was kept below 40° C. Solution changed from yellow to red. After 30 min reaction was heated to 95 C for 3 hrs. Solution was green already after 1 hr. Standing over night at ambient temperature the batch was diluted into 5 l water/ice and stirred for 10 more minutes. A turquoise suspension formed and changed colour to olive green after 30 min. After filtration, water-washings and drying 122 g white solid was obtained with $R_t$~2.53 min in LC-MS system 1 and correct mass of M+H+ ~338.

EXAMPLE 6

Synthesis of [2-(5-Chloro-2-fluoro-phenyl)-quinolin-4-yl]-(3-nitro-pyridin-4-yl)-amine (M 394.80)

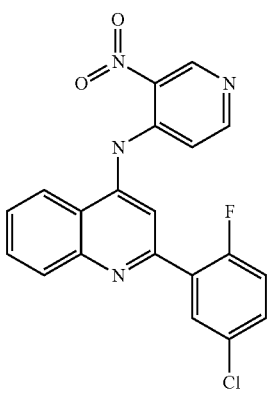 [SMILES: O=[N+]([O-])c1cnccc1Nc1cc(-c2cc(Cl)ccc2F)nc2ccccc12]

10 g 4-Bromo-2-(5-chloro-2-fluoro-phenyl)-quinoline (cf. Example 5; M 336.59), and 4.13 g of 3-nitro-4-amino pyridine in 500 ml tert. amylalcohol were treated under argon with 272 mg Pd$_2$(dba)$_3$ (ABCR) and 0.69 g Xanthphos (ABCR) under basic conditions adjusted with 12.6 g K$_3$PO$_4$ at 117° C. external (100° C. internal temperature) for 6.5 hrs. Work-up with ethyl acetate extract washed with aqueous 5% KHSO$_4$ solution (pH 2) and aqueous 5 NaHCO$_3$ solution yielded after drying with Na$_2$SO$_4$, filtration and washings with methanol 6.6 g yellow powder of correct mass M+H+ 395 and $R_t$~2.67 min and $R_f$~0.44 in TLC on silica in petrolether/EE 2:1.

EXAMPLE 7

Synthesis of N*4*-[2-(5-Chloro-2-fluoro-phenyl)-quinolin-4-yl]-pyridine-3,4

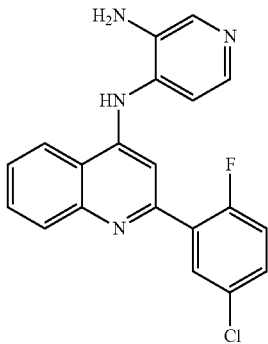 [SMILES: Nc1cnccc1Nc1cc(-c2cc(Cl)ccc2F)nc2ccccc12]

13.4 g [2-(5-Chloro-2-fluoro-phenyl)-quinolin-4-yl]-(3-nitro-pyridin-4-yl)-amine (cf. Example 6) dissolved in 150 ml THF were hydrogenated to give after filtration and evaporation 11.8 g N*4*-[2-(5-Chloro-2-fluoro-phenyl)-quinolin-4-yl]-pyridine-3,4-diamine as a foam, which was digerated with ether and then ether/petrol ether, then filtered and dried to give 9.58 g red-brown solid material with correct mass and 85% HPLC purity. An additional aliquot of 1.47 g from mother liquor containing product was purified by flash chromatography on a Companion machine on 40 g Analogix silica column with a 20 min-gradient of 0-10 MeOH in $CH_2Cl_2$ at 40 ml/min. Monitoring was performed at 254 nm. 566 mg correct addition product were isolated.

EXAMPLE 8

Synthesis of N*4*-[2-(2-fluoro-phenyl)-quinolin-4-yl]-pyridine-3,4-diamine (M 330.37)

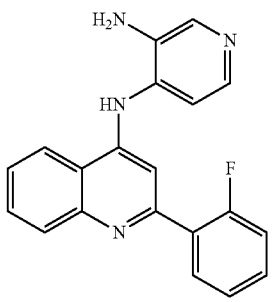 [SMILES: Nc1cnccc1Nc1cc(-c2ccccc2F)nc2ccccc12]

353 mg N*4*-[2-(5-Chloro-2-fluoro-phenyl)-quinolin-4-yl]-pyridine-3,4-diamine (cf. Example 7) dissolved in 60 ml THF and 330 mg triethylamine were hydrogenated over 1.8 g Pd—C (52% water) over night, at normal pressure and ambient room temperature to give after filtration, evaporation and subsequent digeration with ether 238 mg yellow powder product with correct mass $M_+H_+$331 and >90% HPLC purity with a $R_t$~1.23 min in LC-MS system 1. TLC on silica in $CH_2Cl_2$/MeOH 1:1 showed one product at $R_f$~0.21.

EXAMPLE 9

Synthesis of 2-(5-Chloro-2-fluoro-phenyl)-4-(2-methoxymethyl-imidazo[4,5-c]pyridin-1-yl)-quinoline (M 418.86)

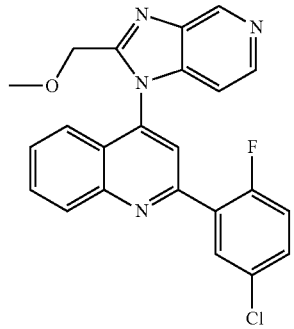 [SMILES: COCc1nc2cnccc2n1-c1cc(-c2cc(Cl)ccc2F)nc2ccccc12]

N*4*-[2-(5-Chloro-2-fluoro-phenyl)-quinolin-4-yl]-pyridine-3,4-diamine (cf. example 7) was acylated with methoxyacetic acid and acid treated like with acetic acid or concentrated HCl. After workup the imidazopyridine was isolated with $R_t$~1.93 min in LC-MS system 1 and correct mass of M+H+ 419 in LC-MS system 1.

EXAMPLE 10

Synthesis of N*4*-[2-(5-Chloro-2-fluoro-phenyl)-quinolin-4-yl]-pyridine-3,4-diamine urea (M 390.8)

N*4*-[2-(5-Chloro-2-fluoro-phenyl)-quinolin-4-yl]-pyridine-3,4-diamine (cf. Example 7) was treated in THF with CDI and DIPEA over night at ambient temperature. After work up the urea derivative was isolated with correct mass M+H+ 391 and $R_t$~1.78 min in LC-MS system 1.

EXAMPLE 11

Synthesis of 1-[2-(2-fluoro-phenyl)-quinolin-4-yl]-1,3-dihydro-imidazo[4,5-c]pyridin-2-one (M 356.36)

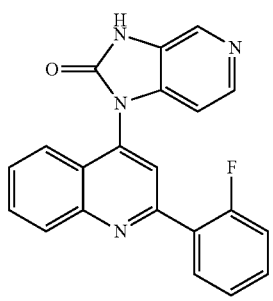 [SMILES: O=c1[nH]c2cnccc2n1-c1cc(-c2ccccc2F)nc2ccccc12]

The urea compound of Example 10 was hydrogenated on Pd/C 5% in methanol to give the des-chloro compound with correct mass M+H+ 357 and $R_t$~1.58 min in LC-MS system 1.

EXAMPLE 12

Synthesis of [2-(5-Chloro-2-fluoro-phenyl)-quinolin-4-yl]-(3-methoxy-pyridin-4-yl)-amine (M 379.82)

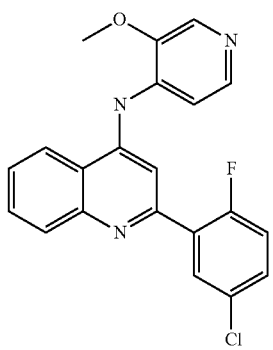 [SMILES: COc1cnccc1Nc1cc(-c2cc(Cl)ccc2F)nc2ccccc12]

250 mg 4-Bromo-2-(5-chloro-2-fluoro-phenyl)-quinoline (cf. Example 5; M 336.59) and 94 mg of 3-methoxy-4-amino pyridine (Tyger Scientific) in 25 ml dioxane were treated under argon with 14 mg Pd$_2$(dba)$_3$ (Aldrich) and 22 mg Xanthphos (ABCR) under basic conditions adjusted with 485 mg Cs$_2$CO$_3$ at 85° C. internal temperature over night. Work-up was conducted by RP HPLC on a Gemini column Axia RP18-100×30 mm/10 µm-110 A. Elution was performed with a 30 min gradient of 1-99% buffer B (=0.3% TFA in CH$_3$CN) in buffer A (=0.3% TFA in water) at 30 ml/min and monitoring at 215 nm. Pooled material after drying yielded 228 mg product of correct mass M+H+ 380 and $R_t$~1.74 min in LC-MS system 2.

EXAMPLE 13

Synthesis of N-[2-(6-Methyl-pyridin-2-yl)-quinolin-4-yl]-pyrimidine-4,6-diamine

Referring to the previous examples, compound N-[2-(6-Methyl-pyridin-2-yl)-quinolin-4-4-yl]-pyrimidine-4,6-diamine was analogously obtained in accordance with the following scheme:

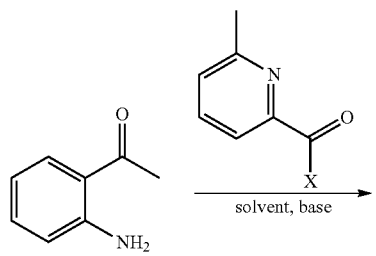

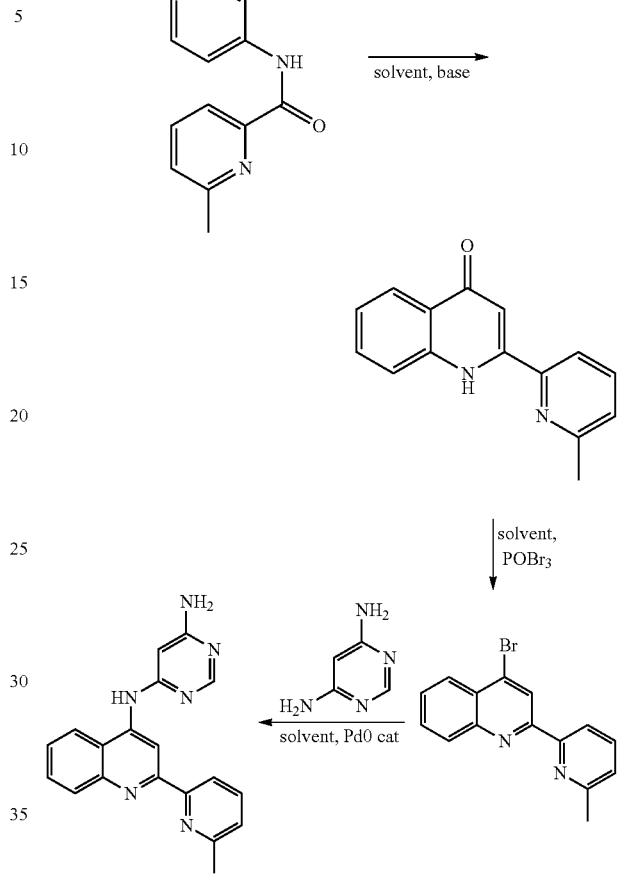

EXAMPLE 14

Pharmaceutical Preparations

Example A

Injection Vials

A solution of 100 g of an active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

Example B

Suppositories

A mixture of 20 g of an active ingredient according to the invention was melted with 100 g of soya lecithin and 1400 g of cocoa butter, poured into moulds and allowed to cool. Each suppository contained 20 mg of active ingredient.

Example C

Solution

A solution was prepared from 1 g of an active ingredient according to the invention, 9.38 g of NaH$_2$PO$_4$.2H2O, 28.48 g of Na$_2$HPO$_4$.12H$_2$O and 0.1 g of benzalkonium chloride in 940 ml of bidistilled water. The pH was adjusted to 6.8, and the solution was made up to 1 l and sterilized by irradiation. This solution could be used in the form of eye drops.

Example D

Ointment 500 mg of an active ingredient according to the invention were mixed with 99.5 g of Vaseline under aseptic conditions.

Example E

Tablets

A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

Example F

Coated Tablets

Tablets were pressed analogously to Example E and subsequently coated in a conventional manner with a coating of sucrose, potato starch, talc, tragacanth and dye.

Example G

Capsules 2 kg of an active ingredient according to the invention were introduced into hard gelatin capsules in a conventional manner in such a way that each capsule contained 20 mg of the active ingredient.

Example H

Ampoules

A solution of 1 kg of an active ingredient according to the invention in 60 l of bidistilled water was sterile filtered, transferred into ampoules, lyophilized under sterile conditions and sealed under sterile conditions. Each ampoule contained 10 mg of active ingredient.

Example I

Inhalation Spray 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:

1. A compound of formula (II)

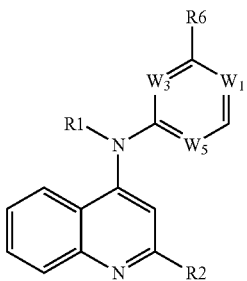

(II)

wherein

W$_1$ denotes N or CR7;

W$_3$ denotes N or CR5;

W$_5$ denotes N or CR9;

wherein at least one of W$_1$, W$_3$ and W$_5$ is N;

R1 denotes H or A;

R5 denotes H, A, OA, CN, -Alk-OY, COOY, —CO—NYY, SA, NYY, —NH—CO-Alk-OY, —NH—CO-Alk-OCOY, —NH—CO-Alk-NYY, —NH—CO—NYY, —NH—CO-Het$^3$, —NH—SO$_2$—NYY, —CO—NH-Alk-NYY or Het$^3$;

or

R1, R5 together denote —CH═CH—, —C(Y)═N—, —C(Alk-OY)═N—, —CO—N(COOY)—, —CO—NH— or —SO$_2$—NH—;

R6 denotes H, A, OA, NYY, —NH-Alk-NYY, —NH—COA or —NH—CO-Alk-NYY;

or

R5, R6 together denote ═CH—CH═C(Y)—CH═ or —N═CH—CH═CH—;

R7, R9 denote H;

R2 denotes phenyl, which is optionally mono- or disubstituted by at least one substituent selected from the group consisting of F, Cl, Br, CH$_3$, CF$_3$, CN, and OCH$_3$;

Y denotes H, A or OA;

A denotes unbranched or branched alkyl having 1-4 C atoms, in which 1-5 H atoms are optionally replaced by F and/or Cl;

Alk denotes alkylene having 1-3 C atoms;

Het$^3$ denotes piperazine, piperidine, morpholine, pyrrolidine, piperidone, morpholinone or pyrrolidone, which is optionally monosubstituted by A, Hal, COOY or NYY;

and

Hal denotes F, Cl or Br;

or a pharmaceutically acceptable salt thereof.

2. A compound according to claim 1, wherein

R1 denotes H; and

R5 denotes H, A, OA, CN, -Alk-OY, —CO—NYY, SA, NYY, —NH—CO-Alk-OY, —NH—CO-Alk-OCOY, —NH—CO-Alk-NYY, —NH—CO—NYY, —NH—CO-Het$^3$, —NH—SO$_2$—NYY, —CO—NH-Alk-NYY or Het$^3$.

3. A compound according to claim 1, wherein

R1, R5 together denote —CH═CH—, —C(Y)═N—, —C(Alk-OY)═N—, —CO—N(COOY)—, —CO—NH— or —SO$_2$—NH—.

4. A compound according to claim 1, wherein R1 denotes A.
5. A compound according to claim 1, wherein Het³ denotes piperazine, piperidine, morpholine, pyrrolidine, piperidone, morpholinone or pyrrolidone.
6. A compound, which is one of the following compounds
003
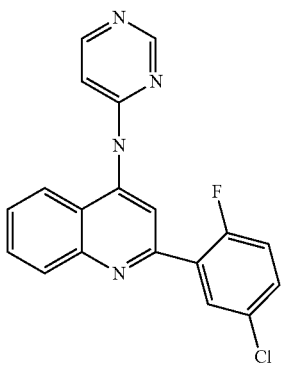
008
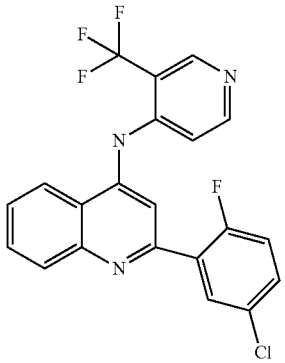
013
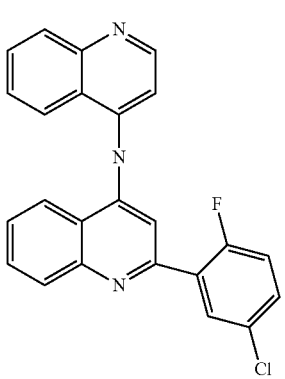
014
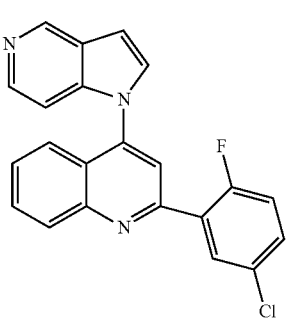
-continued
016
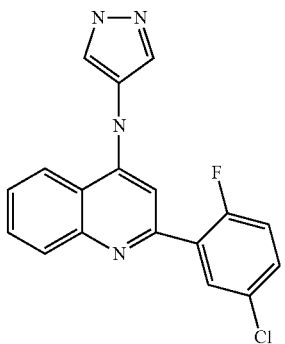
019
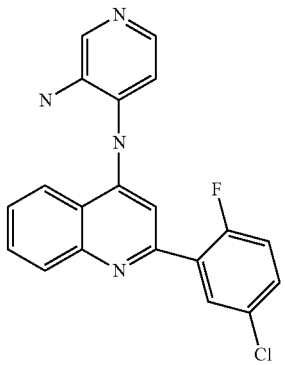
020
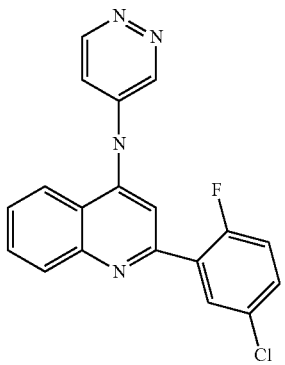
023
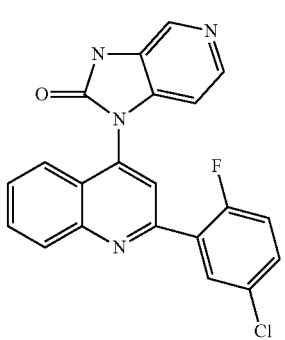

-continued
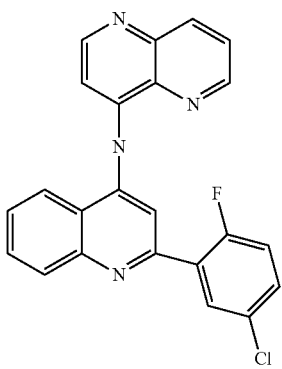
024
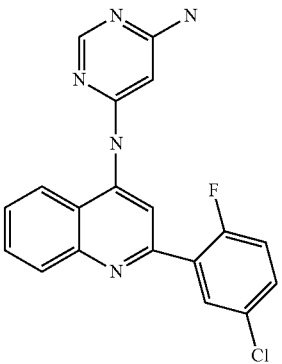
038
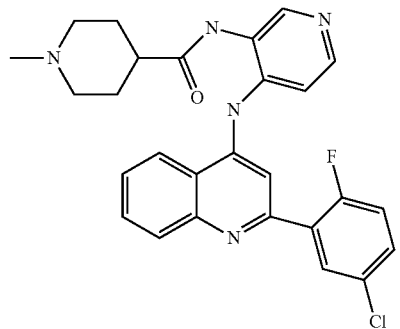
025
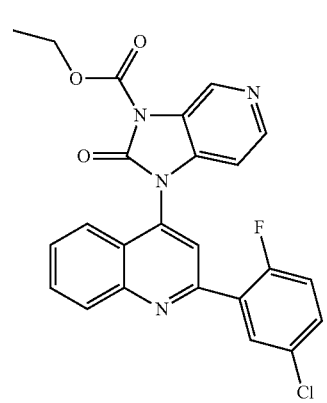
039
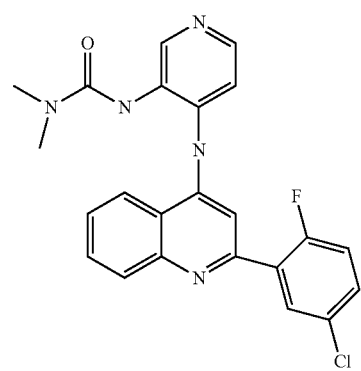
027
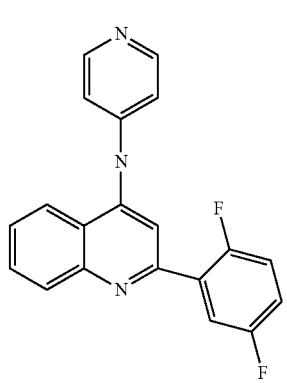
043
031
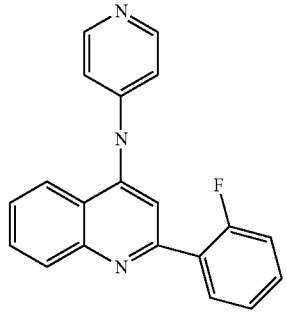
044

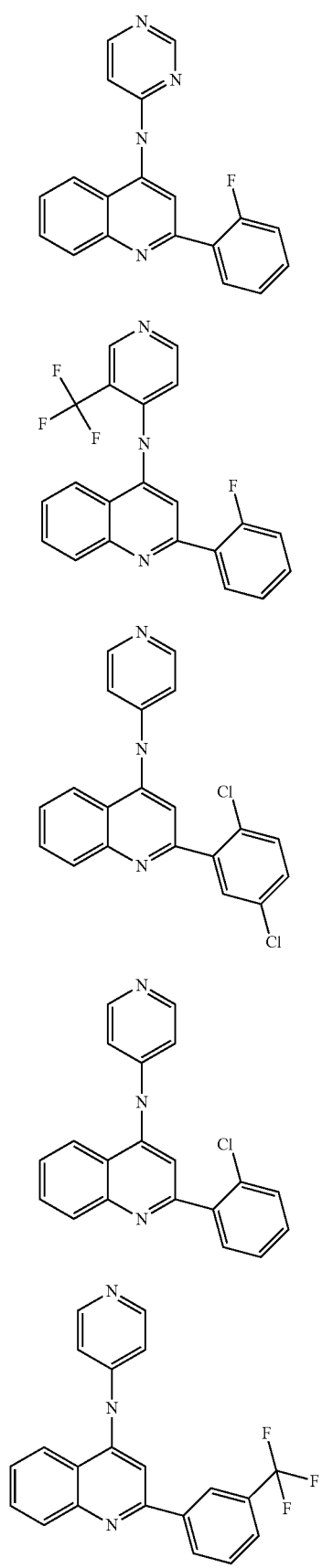

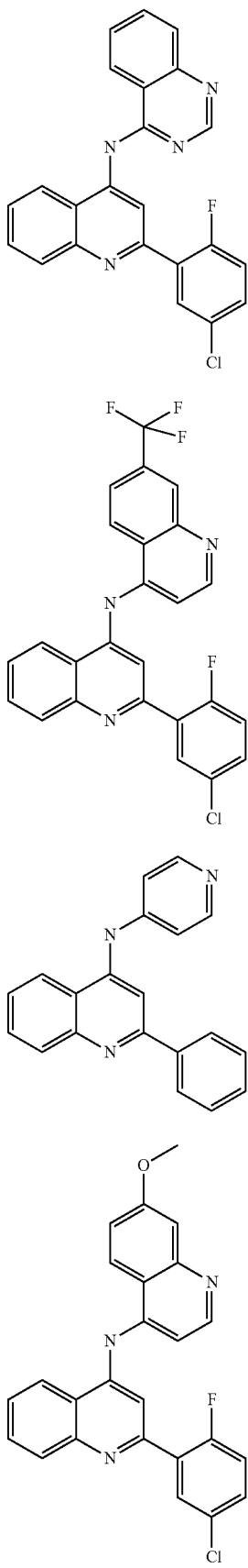
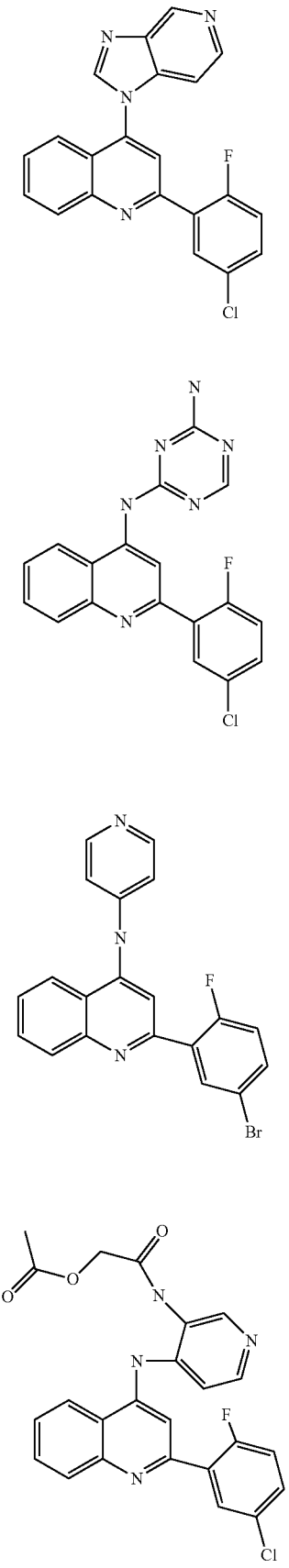

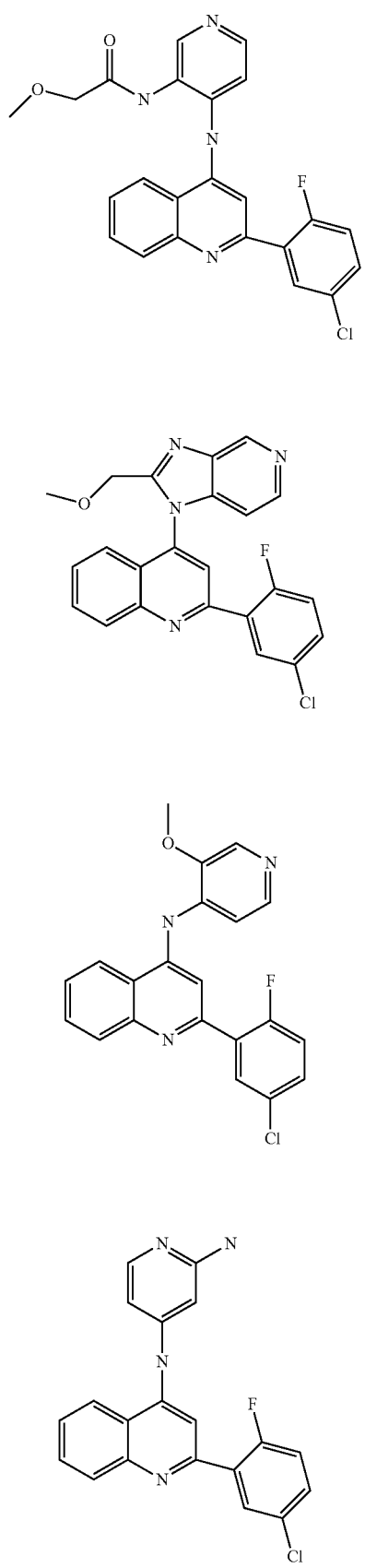
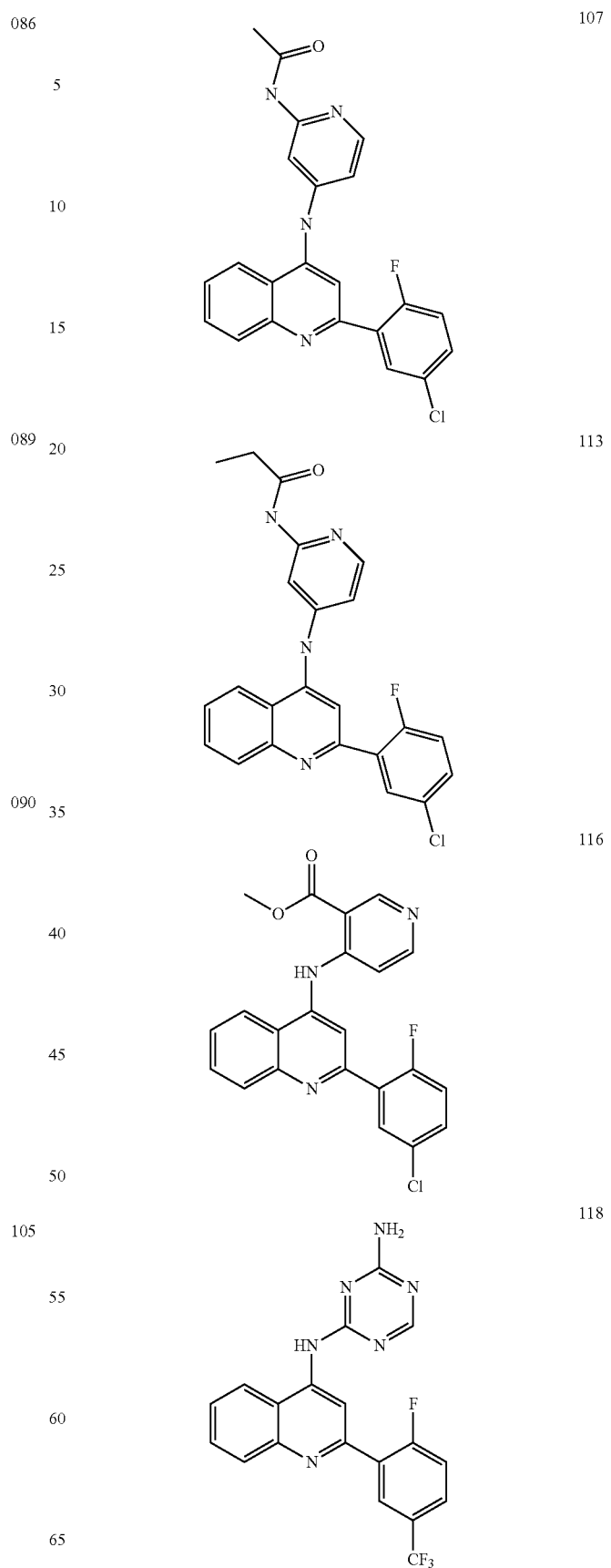

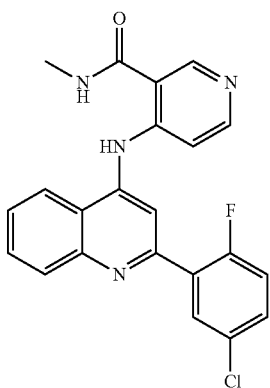
119
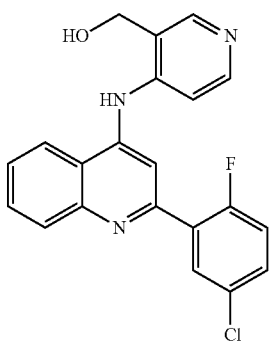
120
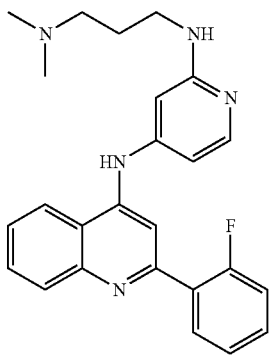
121
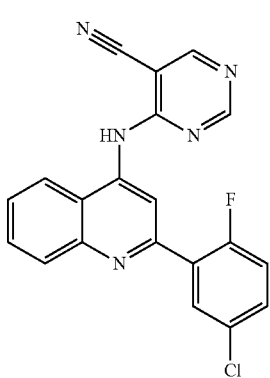
122
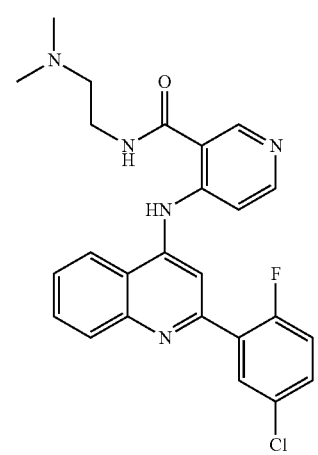
123
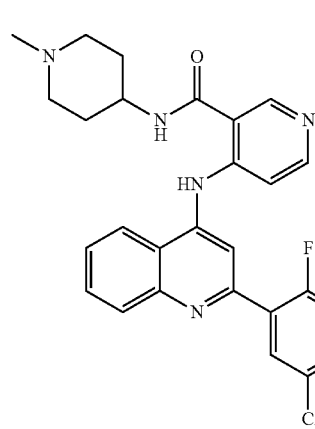
125
or
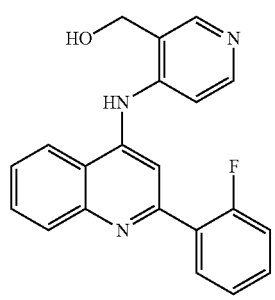
127
or a pharmaceutically acceptable salt thereof.
7. A compound according to claim 6, which is one of the following compounds
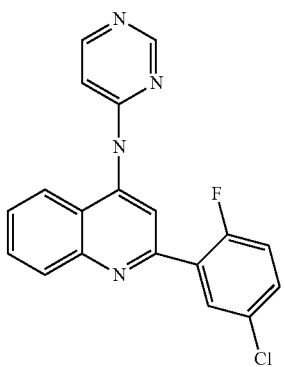
003

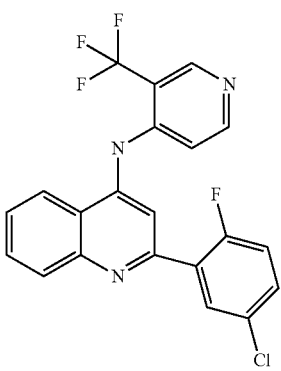
008
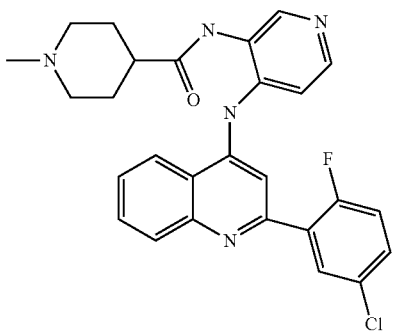
027
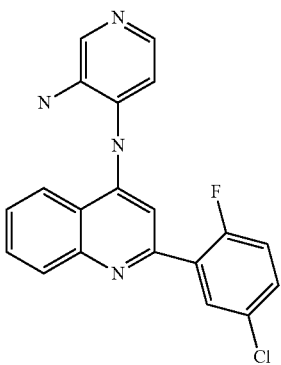
019
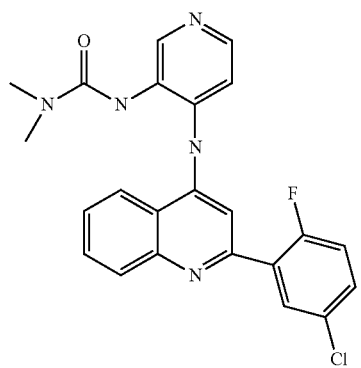
031
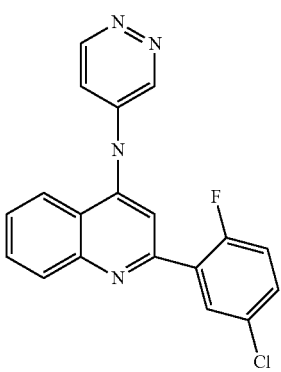
020
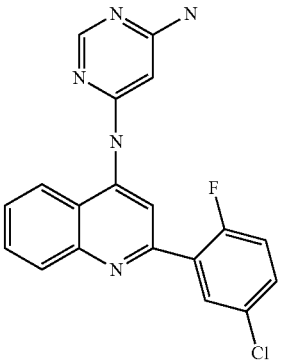
038
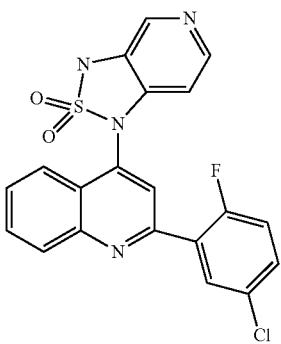
025
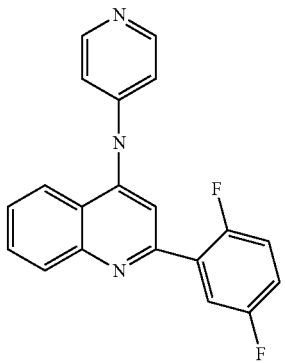
043

044
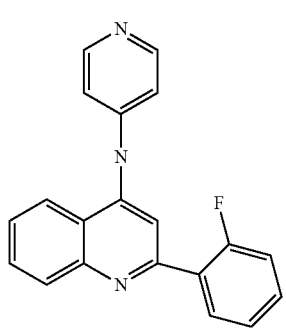
045
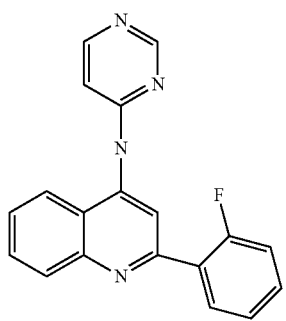
046
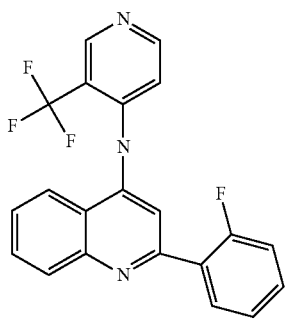
048
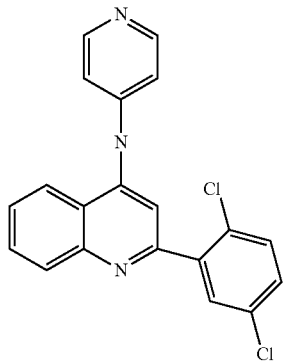
050
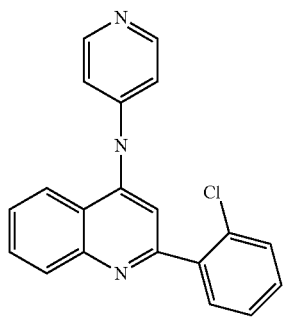
051
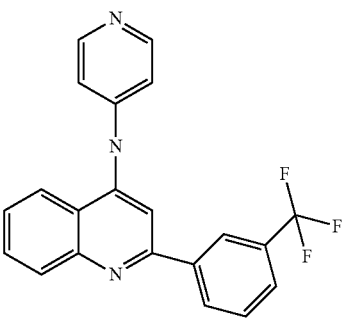
054
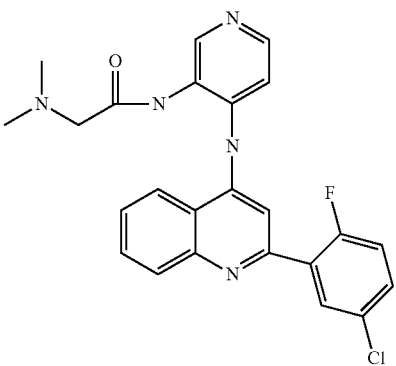
056
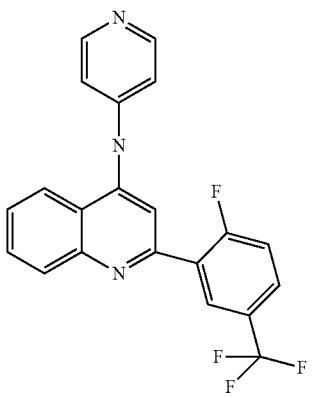
059
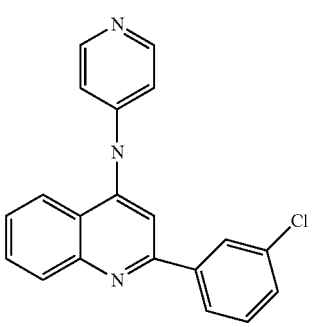

| 157 -continued | 158 -continued |
|---|---|
| 064 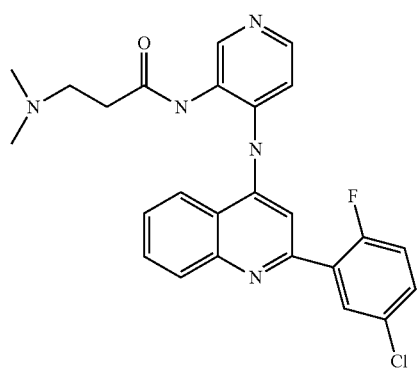 | 085 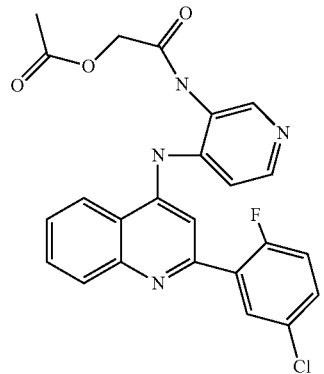 |
| 073 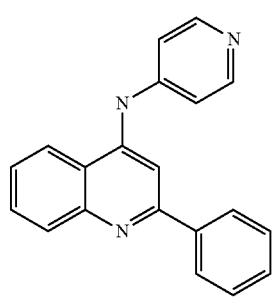 | 086 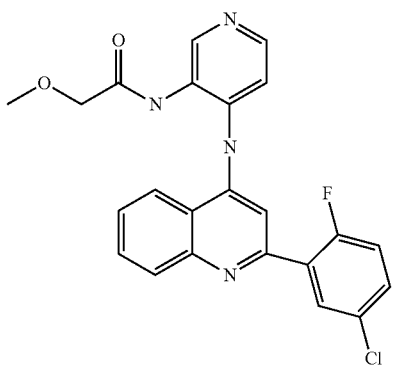 |
| 078 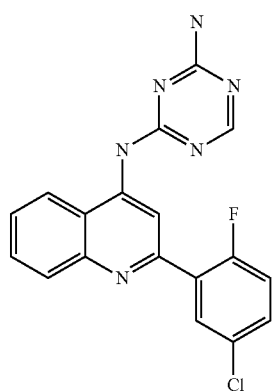 | 090 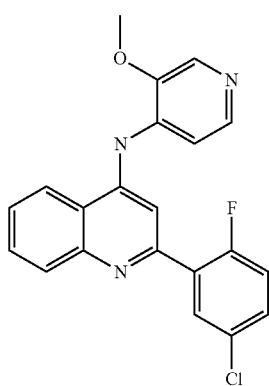 |
| 084 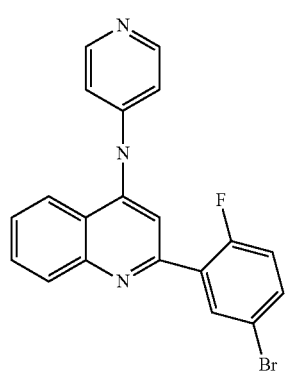 | 105 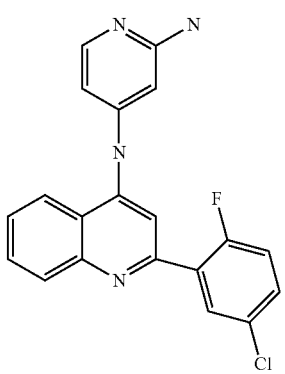 |

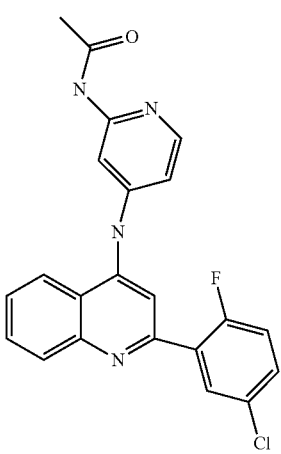
107
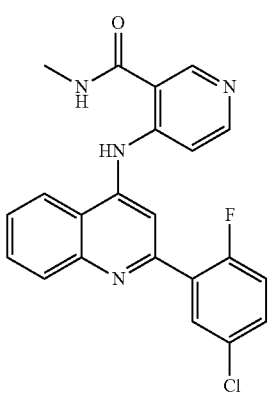
119
113
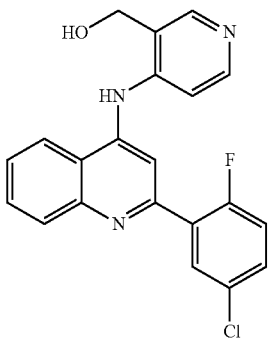
120
116
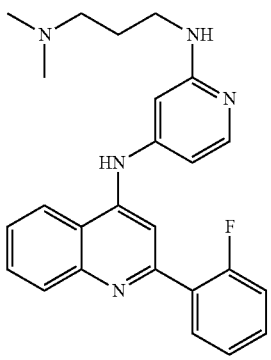
121
118
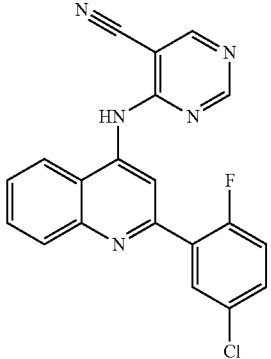
122

-continued
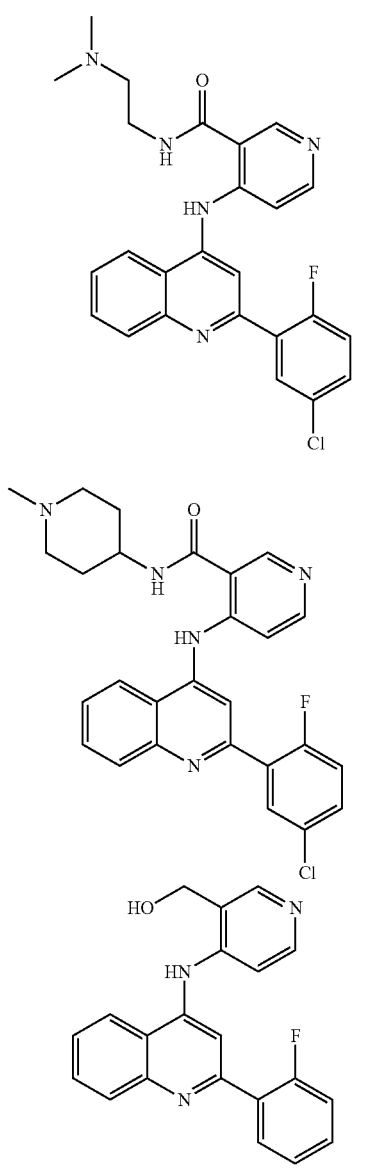
or a pharmaceutically acceptable salt thereof.
8. A compound according to claim 6, which is one of the following compounds
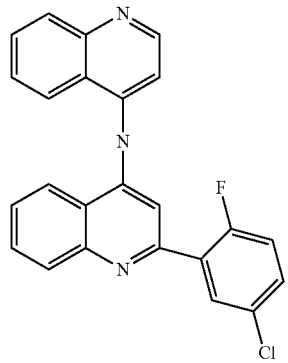
-continued
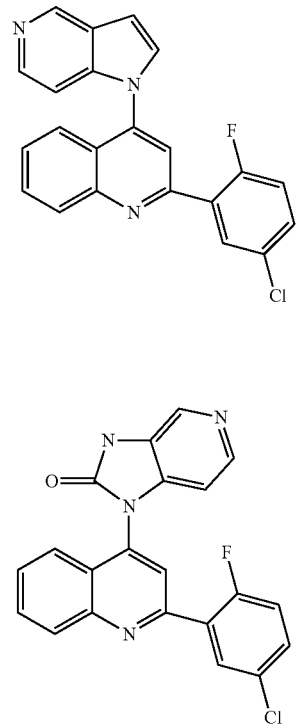
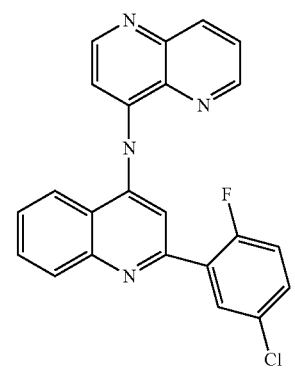
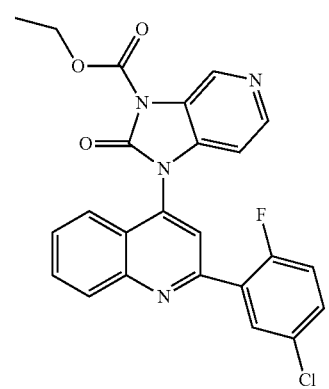

163
-continued

068
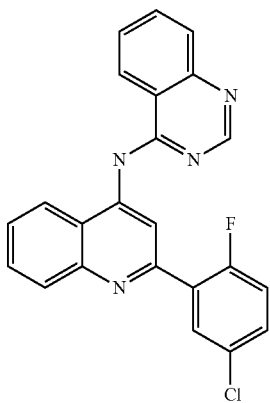

069
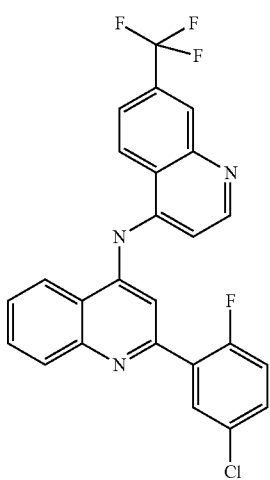

075
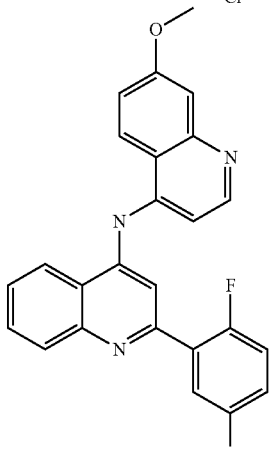

077
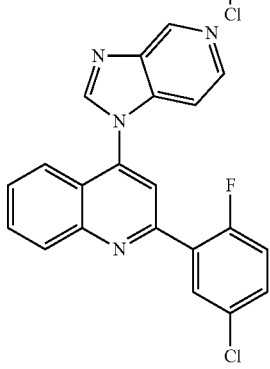

164
-continued

089
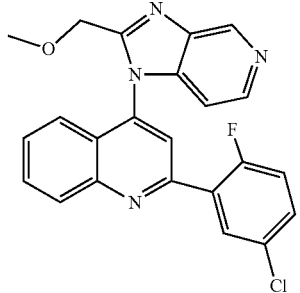

or a pharmaceutically acceptable salt thereof.

9. A pharmaceutical composition, comprising a compound of claim 1 or a pharmaceutically acceptable salt thereof and one or more pharmaceutically acceptable carriers.

10. A pharmaceutical composition, comprising a compound of claim 6 or a pharmaceutically acceptable salt thereof and one or more pharmaceutically acceptable carriers.

11. A process for preparing a compound of formula (II) of claim 1, comprising
(a) reacting a compound of formula (IV)

(IV)
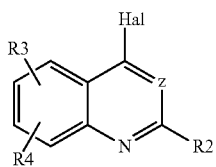

wherein
Z denotes CH,
R2, R3, and R4 denote H, and
Hal has the meaning as for the compound of formula (II), with a compound of formula (V)

(V)
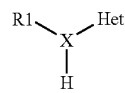

wherein
X denotes N,
R1 has the meaning as for the compound of formula (II), and
Het denotes

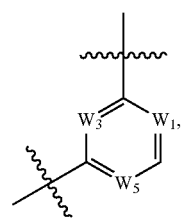

which is defined as for the compound of formula (II) under the proviso that R1, R5 together are excluded, to yield a compound of formula (II)
under the proviso that R1, R5 together are excluded, and optionally
(b) converting a base or an acid of a compound of formula (II) into a salt thereof.

12. A method for inhibiting an ATP consuming protein, comprising bringing together said ATP consuming protein and a compound of claim 1 or a pharmaceutically acceptable salt thereof.

13. A method according to claim 12, wherein the ATP consuming protein is a TGF-beta receptor kinase or ALK5.

14. A method for inhibiting an ATP consuming protein, comprising bringing together said ATP consuming protein and a compound of claim 6 or a pharmaceutically acceptable salt thereof.

15. A method according to claim 14, wherein the ATP consuming protein is a TGF-beta receptor kinase or ALK5.

16. A method for inhibiting an ATP consuming protein, comprising bringing together said ATP consuming protein and a compound of claim 7 or a pharmaceutically acceptable salt thereof.

17. A method according to claim 16, wherein the ATP consuming protein is a TGF-beta receptor kinase or ALK5.

18. A method for inhibiting an ATP consuming protein, comprising bringing together said ATP consuming protein and a compound of claim 8 or a pharmaceutically acceptable salt thereof.

19. A method according to claim 18, wherein the ATP consuming protein is a TGF-beta receptor kinase or ALK5.

* * * * *